US012228576B2

(12) United States Patent
Patel et al.

(10) Patent No.: US 12,228,576 B2
(45) Date of Patent: Feb. 18, 2025

(54) DETECTION AND QUANTIFICATION OF AKT-mTOR PATHWAY PROTEINS

(71) Applicant: Pierce Biotechnology, Inc., Rockford, IL (US)

(72) Inventors: Bhavinkumar Patel, Rockford, IL (US); John Rogers, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 0 days.

(21) Appl. No.: 18/068,047

(22) Filed: Dec. 19, 2022

(65) Prior Publication Data

US 2023/0213529 A1 Jul. 6, 2023

Related U.S. Application Data

(62) Division of application No. 16/081,377, filed as application No. PCT/US2017/022062 on Mar. 13, 2017, now Pat. No. 11,561,226.

(60) Provisional application No. 62/308,051, filed on Mar. 14, 2016.

(51) Int. Cl.
*G01N 33/574* (2006.01)
*C07K 16/18* (2006.01)
*G01N 33/541* (2006.01)
*G01N 33/68* (2006.01)

(52) U.S. Cl.
CPC ....... *G01N 33/57496* (2013.01); *C07K 16/18* (2013.01); *G01N 33/541* (2013.01); *G01N 33/57488* (2013.01); *G01N 33/6848* (2013.01); *G01N 33/6863* (2013.01); *G01N 33/6872* (2013.01); *G01N 2440/14* (2013.01)

(58) Field of Classification Search
CPC ........... G01N 33/57496; G01N 33/541; G01N 33/57488; G01N 33/6848; G01N 33/6872; G01N 2440/14; C07K 16/18
See application file for complete search history.

(56) References Cited

U.S. PATENT DOCUMENTS

| | | |
|---|---|---|
| 9,110,074 B2 | 8/2015 | Jamieson Jr. |
| 9,252,003 B2 | 2/2016 | Hermanson et al. |
| 2009/0215098 A1 | 8/2009 | Cutillas et al. |
| 2009/0238808 A1 | 9/2009 | Drewes et al. |
| 2011/0178273 A1 | 7/2011 | Aabersold et al. |
| 2012/0165340 A1 | 6/2012 | Furnari et al. |
| 2012/0295990 A1* | 11/2012 | Krizman ............ G01N 33/6848 514/789 |
| 2013/0023469 A1 | 1/2013 | Pikarsky et al. |
| 2013/0252950 A1 | 9/2013 | Blenis et al. |
| 2015/0140041 A1 | 5/2015 | Vitiello |
| 2016/0067260 A1 | 3/2016 | Dransfield et al. |
| 2017/0168055 A1 | 6/2017 | Krizman et al. |
| 2017/0370942 A1* | 12/2017 | Picotti .................. G01N 33/58 |
| 2018/0214452 A1 | 8/2018 | Lee et al. |

FOREIGN PATENT DOCUMENTS

| | | |
|---|---|---|
| CN | 1551984 A | 12/2004 |
| CN | 101874037 A | 10/2010 |
| CN | 102510903 A | 6/2012 |
| JP | 2009050183 A | 3/2009 |
| WO | 2011140464 A2 | 11/2011 |

OTHER PUBLICATIONS

Anti-Human NAB1 (antigen zinc finger transcription factors EGR1 and EGR2), CD Creative Diagnostic Catalog, 2015, 2 pages.
B. Patel et al., "Abstract 1837: Quantitative analysis of AKT/mTOR pathway using immunoprecipitation and targeted mass spectrometry 1 Cancer Research", Proceedings of the 1 06th Annual Meeting of the American Association for Cancer Research Apr. 18-22, 2015, Philadelphia PA USA, Cancer Research, val. 75, No. 15 suppl, Aug. 1, 2015 (Aug. 1, 2015), XP055379896, Philadelphia PA USA.
B. Patel et al., "Poster note 64456: Quantitative analysis of IGF1R/ AKT/mTOR pathway using multiplex immunoprecipitation and targeted mass spectrometry" In: Mar. 31, 2012 (Mar. 31, 2012). Thermo Fisher Scientific Rockford IL USA, Annual Meeting of the American-Association-For-Cancer-Research; Chicago, IL, USA; Mar. 31-Apr. 4, 2012. XP055394601. ISSN: 0008-5472 pp. 1-3.
Cell Signalling Technology: "Akt (pan) (4004) Mouse mAb" In: "Akt (pan) (4004) Mouse mAb", Jan. 4, 2016 (Jan. 4, 2016), Cell Signalling Technology, Leiden NL, XP055394572, pp. 1-2.
Francesca Pezzuto et al, "Update on Head and Neck Cancer: Current Knowledge on Epidemiology, Risk Factors, Molecular Features and Novel Therapies", Oncology, val. 89, No. 3, Jan. 1, 2015 (Jan. 1, 2015), pp. 125-136, XP055380363, Basel ISSN: 0030-2414, DOI: 1 0.1159/000381717.
International Search Report and Written Opinion for Application No. PCT/US2017/022062, mailed Aug. 8, 2017, 25 pages.
J. S. Logue and Deborah K. Morrison., "Complexity in the signaling network: insights from the use of targeted inhibitors in cancer therapy", Genes and Development., val. 26, No. 7, Apr. 1, 2012 (Apr. 1, 2012 ), p. 641, XP055380360, Cold Spring Harbour NY USA ISSN: 0890-9369, DOI: 10.1101 /gad. 186965.112.
Patel et al., Abstract 3884: Quantitative Analysis of IGF1R/AKT/ mTOR Pathway Using Multiplex Immunoprecipitation and Targeted Mass Spectrometry, Cancer Research, DOI:10.1158/1538-7445.AM2016-3884 (2016).
Patel et al., Poster Note 64456: Quantitative Analysis of AKT/ mTOR Pathway using Immunoprecipitation and Targeted Mass Spectrometry, Thermo Fisher Scientific, Rockford, IL, USA (2015).
Populo et al., "The mTOR Signalling Pathway in Human Cancer," Int. J. Mol. Sci., 2012, 13: 1886-1918.

(Continued)

*Primary Examiner* — Changhwa J Cheu
(74) *Attorney, Agent, or Firm* — Klarquist Sparkman, LLP

(57) ABSTRACT

This disclosure relates to the field of mass spectrometry analysis. In some embodiments, the disclosure relates to compositions and methods for detecting and quantifying proteins in the AKT-mTOR pathway by immunoprecipitation enrichment followed by mass spectrometry analysis.

18 Claims, 12 Drawing Sheets

Specification includes a Sequence Listing.

(56) References Cited

OTHER PUBLICATIONS

Suzanne Smith et al., "Abstract 1841: Enrichment of IGF1 R-AKT-mTOR pathway proteins using immunoprecipitation and proteomic analysis by mass spectrometry I Cancer Research", Proceedings: American Association for Cancer Research 1 06th Annual Meeting 2015; Apr. 18-22, 2015; Philadelphia, PA, USA. Cancer Research, val. 75, No. 15 Suppl, Aug. 1, 2015 (Aug. 1, 2015 ), XP055379897, Philadelphia PA USA.

Turney et al: "Depletion of the type 1 IGF receptor delays repair of radiation-induced DNA double strand breaks", Radiotherapy and Oncology, vol. 103, No. 3,Mar. 14, 2012 (Mar. 14, 2012), pp. 402-409, XP028517624, ISSN: 0167-8140, DOI: 10.1016/J.RADONC.2012.03.009 [retrieved on Mar. 22, 2012].

* cited by examiner

| IP Antibody | Targets Identified | Neat No. of Unique Peptides | IP Enriched No. of Unique Peptides | | Relevant Phosphopeptide ID |
|---|---|---|---|---|---|
| | | | -IGF | +IGF | |
| Phospho AKT | AKT1 | - | 3 | 20 | +IGF: Ser473 |
| | AKT2 | - | - | 14 | +IGF: Ser474 |
| | AKT3 | - | - | 13 | N/A |
| AKT1 | AKT1 | - | 16 | 12 | N/A |
| | AKT2 | - | 9 | 11 | N/A |
| | AKT3 | - | 5 | 3 | N/A |
| Phospho mTOR | mTOR | 2 | 75 | 82 | +IGF: Thr2446, Ser2448 |
| | RICTOR | - | 0 | 2 | N/A |
| | SIN1 | - | 2 | 3 | N/A |
| | Gβl | - | 4 | 4 | N/A |
| IGF1R | IGF1R | 4 | 13 | 13 | N/A |
| | IR | - | 10 | 6 | N/A |
| Phospho IGF1R | IGF1R | 4 | 0 | 5 | +IGF: Tyr1135/1136 |
| PRAS40 | PRAS40 | - | 8 | 8 | +IGF: Thr246 |
| Phospho PRAS40 | PRAS40 | - | 8 | 6 | +IGF: Thr246 |

FIG. 3

| Target | Peptide No. | Seq. ID No. | LOD (fmol) | LLOQ (fmol) | ULOQ (fmol) | Linearity ($R^2$) |
|---|---|---|---|---|---|---|
| AKT2 | SDGSFIGYK | 6 | 0.08 | 0.23 | 500 | 0.9998 |
| AKT1 | NDGTFIGYK | 1 | 0.08 | 0.69 | 500 | 0.9981 |
| mTOR | GNNLQDTLR | 96 | 0.08 | 0.23 | 500 | 0.9997 |
| | GYTLADEEEDPLIYQHR | 98 | 0.23 | 0.69 | 500 | 0.9999 |
| IGF1R | TTINNEYNYR | 40 | 0.08 | 0.23 | 500 | 0.9999 |
| | YADGTIDIEEVTENPK | 42 | 0.23 | 0.69 | 500 | 0.9997 |
| IR | TVNESASLR | 23 | 0.08 | 0.08 | 500 | 0.9990 |
| | TIDSVTSAQELR | 16 | 0.23 | 0.23 | 500 | 0.9990 |
| PRAS40 | LNTSDFQK | 200 | 0.23 | 0.69 | 500 | 0.9981 |
| p70S6K | DGFYPAPDFR | 157 | 0.08 | 0.23 | 500 | 0.9980 |
| TSC2 | GYTISDSAPSR | 73 | 0.23 | 0.69 | 500 | 0.9981 |
| | YTEFLTGLGR | 80 | 0.23 | 0.69 | 500 | 0.9980 |
| PTEN | NNIDDVVR | 208 | 0.08 | 0.08 | 500 | 0.9990 |
| | AQEALDFYGEVR | 209 | 0.08 | 0.08 | 500 | 0.9990 |
| GSK3α | VTTVVATLGQGPER | 124 | 0.23 | 0.69 | 500 | 0.9980 |
| | SQEVAYTDIK | 120 | 0.08 | 0.23 | 500 | 0.9980 |
| GSK3β | LLEYTPTAR | 133 | 0.08 | 0.08 | 500 | 0.9980 |
| IRS1 | SVSAPQIINPIR | 57 | 0.08 | 0.23 | 500 | 0.9990 |
| | TGIAAEEVSLPR | 59 | 0.08 | 0.23 | 500 | 0.9985 |

FIG. 4

| Target | 10 Plex Phospho Assay | | 11 Plex Total Assay | |
|---|---|---|---|---|
| | -IGF | +IGF | -IGF | +IGF |
| AKT1 | - | 9 | 25 | 30 |
| AKT2 | - | 4 | 24 | 26 |
| mTOR | 48 | 56 | 25 | 28 |
| IGF1R | 1 | 3 | 32 | 35 |
| IR | N/A | N/A | 29 | 26 |
| PRAS40 | 5 | 7 | 9 | 10 |
| p70S6K | 9 | 14 | 11 | 12 |
| TSC2 | 5 | 10 | 42 | 45 |
| PTEN | - | 1 | 5 | 9 |
| GSK3α | 7 | 6 | 19 | 21 |
| GSK3β | 13 | 10 | 23 | 23 |
| IRS1 | 4 | 11 | 45 | 54 |
| PIK3R1 | - | - | - | 22 |
| PIK3CA | - | - | - | 2 |
| PIK3CB | - | - | - | 6 |
| PIK3R2 | - | - | - | 22 |
| GSKIP | - | - | 2 | 2 |
| TSC1 | - | - | 2 | 4 |

FIG. 5

| Target | Cell Line | Detected by Q Exactive HF | | Quantified by SRM/PRM | |
|---|---|---|---|---|---|
| | | Neat | Enriched-IP | Neat | Enriched-IP |
| AKT1 | A549 | − | + | − | + |
| | HCT116 | − | + | − | + |
| AKT2 | A549 | − | + | − | + |
| | HCT116 | − | + | − | + |
| mTOR | A549 | +(2) | +(82) | − | + |
| | HCT116 | +(9) | +(110) | − | + |
| IGF1R | A549 | +(4) | +(22) | − | + |
| | HCT116 | − | + | − | + |
| IR | A549 | − | + | − | + |
| | HCT116 | − | + | − | + |
| PRAS40 | A549 | +(2) | +(8) | − | + |
| | HCT116 | +(2) | +(7) | − | + |
| p70S6K | A549 | − | + | − | + |
| | HCT116 | − | + | − | + |
| TSC2 | A549 | − | + | − | + |
| | HCT116 | − | + | − | + |
| PTEN | A549 | − | + | − | + |
| | HCT116 | − | + | − | + |
| GSK3α | A549 | +(5) | +(23) | − | + |
| | HCT116 | − | +(21) | − | + |
| GSK3β | A549 | +(4) | +(12) | − | + |
| | HCT116 | +(3) | +(10) | − | + |
| IRS1 | A549 | − | + | − | + |
| | HCT116 | +(4) | +(10) | − | + |

FIG. 8

Technology Correlation for Total AKT-mTOR Pathway Targets

| Target | Correlation* | Comment |
|---|---|---|
| AKT1 | 3/4 | Low Western correlation |
| IGF1R | 4/4 | Good correlation in all |
| IR | 2.5/4 | Low Luminex correlation, moderate Western |
| IRS1 | 3.5/4 | Moderate ELISA correlation |
| p70S6K | 4/4 | Good correlation in all |
| mTOR | 2.5/4 | Correlation b/w Western & ELISA, correlation b/w IP-MS & Luminex |
| GSK3a | 2.5/4 | Slight correlation b/w all techniques |
| GSK3b | 2.5/4 | Good correlation b/w Western & ELISA, Moderate b/w Luminex & IP-MS |
| PRAS40 | 2/4 | Correlation b/w Luminex & ELISA |
| PTEN | 3.5/4 | Slight difference in Luminex |
| TSC2 | 2/4 | Low ELISA |

FIG. 9

Technology Correlation for Phospho AKT-mTOR Pathway Targets

| Target | Correlation* | Comment |
|---|---|---|
| AKT1 | 2/4 | Correlation b/w Luminex & ELISA |
| AKT2 | 2/4 | Correlation b/w IP-MS & WB |
| IGF1R | 1.5/4 | Low correlation B/W Luminex & ELISA |
| IR | 0/0 | No Ab/Failed for all assays |
| IRS1 | 2/3 | No ELISA Kit ($3500), correlation b/w Luminex & IP-MS |
| p70S6K | 4/4 | Good correlation in all |
| mTOR | 3.5/4 | Slight difference in ELISA |
| GSK3a | 2/3 | ELISA failed, IP-MS & WB concur |
| GSK3b | 2/3 | ELISA failed, Luminex & WB concur |
| PRAS40 | 1.5/2 | No correlation, Luminex & ELISA Failed |
| PTEN | 2/4 | Correlation b/w WB and ELISA |
| TSC2 | 1.5/4 | No correlation b/w assays |

FIG. 10

IP to WB Validation of AKT-mTOR Pathway Targets

| Target-Phos | Good WB Ab? | # Attempts to Validate ≥ 1 Ab# |
|---|---|---|
| pAKT1 | Y | 6 |
| pIR* | Y | 8 |
| pIGF1R* | Y | 7 |
| pIRS1* | Y | 4 |
| pmTOR* | Y | 5 |
| pP70S6K-b | Y | 1 |
| pGSK3a | Y | 3 |
| pGSK3b | Y | 4 |
| pTSC2* | Y | 10 |
| pRPS6 | Y | 2 |
| pPRAS40 | Y | 2 |
| pPTEN | Y | 2 |

| Target-Total | Good WB Ab? | # Attempts to Validate ≥ 1 Ab# |
|---|---|---|
| AKT1 | Y | 1 |
| IR* | Y | 4 |
| IGF1R* | Y | 3 |
| IRS1* | Y | 3 |
| mTOR* | Y | 3 |
| P70S6K-b | Y | 1 |
| pGSK3a | Y | 1 |
| pGSK3b | Y | 2 |
| TSC2* | Y | 3 |
| RPS6 | Y | 2 |
| PRAS40 | Y | 3 |
| PTEN | Y | 1 |

* Notates optimized protocol for high-molecular weight targets

FIG. 11

SEQUENCE LISTING

```
Sequence total quantity: 424
SEQ ID NO: 1                moltype = AA  length = 9
FEATURE                     Location/Qualifiers
REGION                      1..9
                            note = Description of Artificial Sequence: Synthetic Native
                             peptide sequence
source                      1..9
                            mol_type = protein
                            organism = synthetic construct
SEQUENCE: 1
NDGTFIGYK                                                                       9

SEQ ID NO: 2                moltype = AA  length = 8
FEATURE                     Location/Qualifiers
REGION                      1..8
                            note = Description of Artificial Sequence: Synthetic Native
                             peptide sequence
source                      1..8
                            mol_type = protein
                            organism = synthetic construct
SEQUENCE: 2
SLLSGLLK                                                                        8

SEQ ID NO: 3                moltype = AA  length = 16
FEATURE                     Location/Qualifiers
REGION                      1..16
                            note = Description of Artificial Sequence: Synthetic Native
                             peptide sequence
source                      1..16
                            mol_type = protein
                            organism = synthetic construct
SEQUENCE: 3
EAPLNNFSVA QCQLMK                                                              16

SEQ ID NO: 4                moltype = AA  length = 15
FEATURE                     Location/Qualifiers
REGION                      1..15
                            note = Description of Artificial Sequence: Synthetic Native
                             peptide sequence
MOD_RES                     8
                            note = Phosphorylation
source                      1..15
                            mol_type = protein
                            organism = synthetic construct
SEQUENCE: 4
RPHFPQFSYS ASGTA                                                               15

SEQ ID NO: 5                moltype = AA  length = 15
FEATURE                     Location/Qualifiers
REGION                      1..15
                            note = Description of Artificial Sequence: Synthetic Native
                             peptide sequence
source                      1..15
                            mol_type = protein
                            organism = synthetic construct
SEQUENCE: 5
RPHFPQFSYS ASGTA                                                               15

SEQ ID NO: 6                moltype = AA  length = 9
FEATURE                     Location/Qualifiers
REGION                      1..9
                            note = Description of Artificial Sequence: Synthetic Native
                             peptide sequence
```

```
source                    1..9
                          mol_type = protein
                          organism = synthetic construct
SEQUENCE: 6
SDGSFIGYK                                                                  9

SEQ ID NO: 7              moltype = AA  length = 8
FEATURE                   Location/Qualifiers
REGION                    1..8
                          note = Description of Artificial Sequence: Synthetic Native
                           peptide sequence
source                    1..8
                          mol_type = protein
                          organism = synthetic construct
SEQUENCE: 7
SLLAGLLK                                                                   8

SEQ ID NO: 8              moltype = AA  length = 14
FEATURE                   Location/Qualifiers
REGION                    1..14
                          note = Description of Artificial Sequence: Synthetic Native
                           peptide sequence
MOD_RES                   7
                          note = Phosphorylation
source                    1..14
                          mol_type = protein
                          organism = synthetic construct
SEQUENCE: 8
THFPQFSYSA SIRE                                                           14

SEQ ID NO: 9              moltype = AA  length = 14
FEATURE                   Location/Qualifiers
REGION                    1..14
                          note = Description of Artificial Sequence: Synthetic Native
                           peptide sequence
source                    1..14
                          mol_type = protein
                          organism = synthetic construct
SEQUENCE: 9
THFPQFSYSA SIRE                                                           14

SEQ ID NO: 10             moltype = AA  length = 16
FEATURE                   Location/Qualifiers
REGION                    1..16
                          note = Description of Artificial Sequence: Synthetic Native
                           peptide sequence
source                    1..16
                          mol_type = protein
                          organism = synthetic construct
SEQUENCE: 10
LVPPFKPQVT SETDTR                                                         16

SEQ ID NO: 11             moltype = AA  length = 9
FEATURE                   Location/Qualifiers
REGION                    1..9
                          note = Description of Artificial Sequence: Synthetic Native
                           peptide sequence
source                    1..9
                          mol_type = protein
                          organism = synthetic construct
SEQUENCE: 11
SLLSGLLIK                                                                  9

SEQ ID NO: 12             moltype = AA  length = 10
FEATURE                   Location/Qualifiers
REGION                    1..10
                          note = Description of Artificial Sequence: Synthetic Native
                           peptide sequence
MOD_RES                   1
                          note = Carbamidomethylation
source                    1..10
                          mol_type = protein
                          organism = synthetic construct
SEQUENCE: 12
CSVAAYVSAR                                                                10

SEQ ID NO: 13             moltype = AA  length = 10
FEATURE                   Location/Qualifiers
REGION                    1..10
```

```
                        note = Description of Artificial Sequence: Synthetic Native
                         peptide sequence
source                  1..10
                        mol_type = protein
                        organism = synthetic construct
SEQUENCE: 13
CSVAAYVSAR                                                                          10

SEQ ID NO: 14           moltype = AA   length = 13
FEATURE                 Location/Qualifiers
REGION                  1..13
                        note = Description of Artificial Sequence: Synthetic Native
                         peptide sequence
source                  1..13
                        mol_type = protein
                        organism = synthetic construct
SEQUENCE: 14
GLKPWTQYAI FVK                                                                      13

SEQ ID NO: 15           moltype = AA   length = 14
FEATURE                 Location/Qualifiers
REGION                  1..14
                        note = Description of Artificial Sequence: Synthetic Native
                         peptide sequence
MOD_RES                 6
                        note = Carbamidomethylation
source                  1..14
                        mol_type = protein
                        organism = synthetic construct
SEQUENCE: 15
IELQACNQDT PEER                                                                     14

SEQ ID NO: 16           moltype = AA   length = 12
FEATURE                 Location/Qualifiers
REGION                  1..12
                        note = Description of Artificial Sequence: Synthetic Native
                         peptide sequence
source                  1..12
                        mol_type = protein
                        organism = synthetic construct
SEQUENCE: 16
TIDSVTSAQE LR                                                                       12

SEQ ID NO: 17           moltype = AA   length = 15
FEATURE                 Location/Qualifiers
REGION                  1..15
                        note = Description of Artificial Sequence: Synthetic Native
                         peptide sequence
source                  1..15
                        mol_type = protein
                        organism = synthetic construct
SEQUENCE: 17
TNCPATVING QFVER                                                                    15

SEQ ID NO: 18           moltype = AA   length = 15
FEATURE                 Location/Qualifiers
REGION                  1..15
                        note = Description of Artificial Sequence: Synthetic Native
                         peptide sequence
MOD_RES                 3
                        note = Carbamidomethylation
source                  1..15
                        mol_type = protein
                        organism = synthetic construct
SEQUENCE: 18
TNCPATVING QFVER                                                                    15

SEQ ID NO: 19           moltype = AA   length = 14
FEATURE                 Location/Qualifiers
REGION                  1..14
                        note = Description of Artificial Sequence: Synthetic Native
                         peptide sequence
source                  1..14
                        mol_type = protein
                        organism = synthetic construct
SEQUENCE: 19
TNGDQASCEN ELLK                                                                     14

SEQ ID NO: 20           moltype = AA   length = 14
```

| FEATURE | Location/Qualifiers |
|---|---|
| REGION | 1..14 |
| | note = Description of Artificial Sequence: Synthetic Native peptide sequence |
| MOD_RES | 8 |
| | note = Carbamidomethylation |
| source | 1..14 |
| | mol_type = protein |
| | organism = synthetic construct |

SEQUENCE: 20
TNGDQASCEN ELLK                                                         14

| SEQ ID NO: 21 | moltype = AA   length = 9 |
|---|---|
| FEATURE | Location/Qualifiers |
| REGION | 1..9 |
| | note = Description of Artificial Sequence: Synthetic Native peptide sequence |
| source | 1..9 |
| | mol_type = protein |
| | organism = synthetic construct |

SEQUENCE: 21
VCHLLEGEK                                                                9

| SEQ ID NO: 22 | moltype = AA   length = 9 |
|---|---|
| FEATURE | Location/Qualifiers |
| REGION | 1..9 |
| | note = Description of Artificial Sequence: Synthetic Native peptide sequence |
| MOD_RES | 2 |
| | note = Carbamidomethylation |
| source | 1..9 |
| | mol_type = protein |
| | organism = synthetic construct |

SEQUENCE: 22
VCHLLEGEK                                                                9

| SEQ ID NO: 23 | moltype = AA   length = 9 |
|---|---|
| FEATURE | Location/Qualifiers |
| REGION | 1..9 |
| | note = Description of Artificial Sequence: Synthetic Native peptide sequence |
| source | 1..9 |
| | mol_type = protein |
| | organism = synthetic construct |

SEQUENCE: 23
TVNESASLR                                                                9

| SEQ ID NO: 24 | moltype = AA   length = 10 |
|---|---|
| FEATURE | Location/Qualifiers |
| REGION | 1..10 |
| | note = Description of Artificial Sequence: Synthetic Native peptide sequence |
| source | 1..10 |
| | mol_type = protein |
| | organism = synthetic construct |

SEQUENCE: 24
DIIKGEAETR                                                              10

| SEQ ID NO: 25 | moltype = AA   length = 9 |
|---|---|
| FEATURE | Location/Qualifiers |
| REGION | 1..9 |
| | note = Description of Artificial Sequence: Synthetic Native peptide sequence |
| source | 1..9 |
| | mol_type = protein |
| | organism = synthetic construct |

SEQUENCE: 25
DIYETDYYR                                                                9

| SEQ ID NO: 26 | moltype = AA   length = 10 |
|---|---|
| FEATURE | Location/Qualifiers |
| REGION | 1..10 |
| | note = Description of Artificial Sequence: Synthetic Native peptide sequence |
| source | 1..10 |
| | mol_type = protein |
| | organism = synthetic construct |

SEQUENCE: 26
DIYETDYYRK                                                              10

```
SEQ ID NO: 27           moltype = AA   length = 9
FEATURE                 Location/Qualifiers
REGION                  1..9
                        note = Description of Artificial Sequence: Synthetic Native
                         peptide sequence
MOD_RES                 3
                        note = Phosphorylation
source                  1..9
                        mol_type = protein
                        organism = synthetic construct SEQUENCE: 27
DIYETDYYR                                                                          9

SEQ ID NO: 28           moltype = AA   length = 9
FEATURE                 Location/Qualifiers
REGION                  1..9
                        note = Description of Artificial Sequence: Synthetic Native
                         peptide sequence
MOD_RES                 7
                        note = Phosphorylation
source                  1..9
                        mol_type = protein
                        organism = synthetic construct SEQUENCE: 28
DIYETDYYR                                                                          9

SEQ ID NO: 29           moltype = AA   length = 9
FEATURE                 Location/Qualifiers
REGION                  1..9
                        note = Description of Artificial Sequence: Synthetic Native
                         peptide sequence
MOD_RES                 8
                        note = Phosphorylation
source                  1..9
                        mol_type = protein
                        organism = synthetic construct SEQUENCE: 29
DIYETDYYR                                                                          9

SEQ ID NO: 30           moltype = AA   length = 9
FEATURE                 Location/Qualifiers
REGION                  1..9
                        note = Description of Artificial Sequence: Synthetic Native
                         peptide sequence
MOD_RES                 7..8
                        note = Phosphorylation
source                  1..9
                        mol_type = protein
                        organism = synthetic construct SEQUENCE: 30
DIYETDYYR                                                                          9

SEQ ID NO: 31           moltype = AA   length = 9
FEATURE                 Location/Qualifiers
REGION                  1..9
                        note = Description of Artificial Sequence: Synthetic Native
                         peptide sequence
MOD_RES                 3
                        note = Phosphorylation
MOD_RES                 7
                        note = Phosphorylation
source                  1..9
                        mol_type = protein
                        organism = synthetic construct SEQUENCE: 31
DIYETDYYR                                                                          9

SEQ ID NO: 32           moltype = AA   length = 9
FEATURE                 Location/Qualifiers
REGION                  1..9
                        note = Description of Artificial Sequence: Synthetic Native
                         peptide sequence
MOD_RES                 3
                        note = Phosphorylation
MOD_RES                 8
                        note = Phosphorylation
source                  1..9
                        mol_type = protein
```

```
                        organism = synthetic construct
SEQUENCE: 32
DIYETDYYR                                                                 9

SEQ ID NO: 33           moltype = AA  length = 9
FEATURE                 Location/Qualifiers
REGION                  1..9
                        note = Description of Artificial Sequence: Synthetic Native
                         peptide sequence
MOD_RES                 3
                        note = Phosphorylation
MOD_RES                 7..8
                        note = Phosphorylation
source                  1..9
                        mol_type = protein
                        organism = synthetic construct
SEQUENCE: 33
DIYETDYYR                                                                 9

SEQ ID NO: 34           moltype = AA  length = 13
FEATURE                 Location/Qualifiers
REGION                  1..13
                        note = Description of Artificial Sequence: Synthetic Native
                         peptide sequence
source                  1..13
                        mol_type = protein
                        organism = synthetic construct
SEQUENCE: 34
AENGPGPGVL VLR                                                           13

SEQ ID NO: 35           moltype = AA  length = 18
FEATURE                 Location/Qualifiers
REGION                  1..18
                        note = Description of Artificial Sequence: Synthetic Native
                         peptide sequence
MOD_RES                 8
                        note = Carbamidomethylation
MOD_RES                 12
                        note = Carbamidomethylation
source                  1..18
                        mol_type = protein
                        organism = synthetic construct
SEQUENCE: 35
HYYYAGVCVP ACPPNTYR                                                      18

SEQ ID NO: 36           moltype = AA  length = 18
FEATURE                 Location/Qualifiers
REGION                  1..18
                        note = Description of Artificial Sequence: Synthetic Native
                         peptide sequence
source                  1..18
                        mol_type = protein
                        organism = synthetic construct
SEQUENCE: 36
HYYYAGVCVP ACPPNTYR                                                      18

SEQ ID NO: 37           moltype = AA  length = 12
FEATURE                 Location/Qualifiers
REGION                  1..12
                        note = Description of Artificial Sequence: Synthetic Native
                         peptide sequence
MOD_RES                 3
                        note = Carbamidomethylation
source                  1..12
                        mol_type = protein
                        organism = synthetic construct
SEQUENCE: 37
LGCSASNFVF AR                                                            12

SEQ ID NO: 38           moltype = AA  length = 12
FEATURE                 Location/Qualifiers
REGION                  1..12
                        note = Description of Artificial Sequence: Synthetic Native
                         peptide sequence
source                  1..12
                        mol_type = protein
                        organism = synthetic construct
SEQUENCE: 38
LGCSASNFVF AR                                                            12
```

```
SEQ ID NO: 39            moltype = AA   length = 19
FEATURE                  Location/Qualifiers
REGION                   1..19
                         note = Description of Artificial Sequence: Synthetic Native
                          peptide sequence
source                   1..19
                         mol_type = protein
                         organism = synthetic construct
SEQUENCE: 39
SLRPEMENNP VLAPPSLSK                                                       19

SEQ ID NO: 40            moltype = AA   length = 10
FEATURE                  Location/Qualifiers
REGION                   1..10
                         note = Description of Artificial Sequence: Synthetic Native
                          peptide sequence
source                   1..10
                         mol_type = protein
                         organism = synthetic construct
SEQUENCE: 40
TTINNEYNYR                                                                 10

SEQ ID NO: 41            moltype = AA   length = 18
FEATURE                  Location/Qualifiers
REGION                   1..18
                         note = Description of Artificial Sequence: Synthetic Native
                          peptide sequence
source                   1..18
                         mol_type = protein
                         organism = synthetic construct
SEQUENCE: 41
VAGLESLGDL FPNLTVIR                                                        18

SEQ ID NO: 42            moltype = AA   length = 16
FEATURE                  Location/Qualifiers
REGION                   1..16
                         note = Description of Artificial Sequence: Synthetic Native
                          peptide sequence
source                   1..16
                         mol_type = protein
                         organism = synthetic construct
SEQUENCE: 42
YADGTIDIEE VTENPK                                                          16

SEQ ID NO: 43            moltype = AA   length = 14
FEATURE                  Location/Qualifiers
REGION                   1..14
                         note = Description of Artificial Sequence: Synthetic Native
                          peptide sequence
MOD_RES                  11
                         note = Carbamidomethylation
source                   1..14
                         mol_type = protein
                         organism = synthetic construct
SEQUENCE: 43
YGSQVEDQRE CVSR                                                            14

SEQ ID NO: 44            moltype = AA   length = 14
FEATURE                  Location/Qualifiers
REGION                   1..14
                         note = Description of Artificial Sequence: Synthetic Native
                          peptide sequence
source                   1..14
                         mol_type = protein
                         organism = synthetic construct
SEQUENCE: 44
YGSQVEDQRE CVSR                                                            14

SEQ ID NO: 45            moltype = AA   length = 12
FEATURE                  Location/Qualifiers
REGION                   1..12
                         note = Description of Artificial Sequence: Synthetic Native
                          peptide sequence
source                   1..12
                         mol_type = protein
                         organism = synthetic construct
SEQUENCE: 45
IDIHSCNHEA EK                                                              12
```

```
SEQ ID NO: 46           moltype = AA  length = 10
FEATURE                 Location/Qualifiers
REGION                  1..10
                        note = Description of Artificial Sequence: Synthetic Native
                         peptide sequence
source                  1..10
                        mol_type = protein
                        organism = synthetic construct
SEQUENCE: 46
GVVKDEPETR                                                                  10

SEQ ID NO: 47           moltype = AA  length = 26
FEATURE                 Location/Qualifiers
REGION                  1..26
                        note = Description of Artificial Sequence: Synthetic Native
                         peptide sequence
source                  1..26
                        mol_type = protein
                        organism = synthetic construct
SEQUENCE: 47
ASSDGEGTMS RPASVDGSPV SPSTNR                                                26

SEQ ID NO: 48           moltype = AA  length = 14
FEATURE                 Location/Qualifiers
REGION                  1..14
                        note = Description of Artificial Sequence: Synthetic Native
                         peptide sequence
MOD_RES                 1
                        note = Carbamidomethylation
source                  1..14
                        mol_type = protein
                        organism = synthetic construct
SEQUENCE: 48
CGHSENFFFI EVGR                                                             14

SEQ ID NO: 49           moltype = AA  length = 14
FEATURE                 Location/Qualifiers
REGION                  1..14
                        note = Description of Artificial Sequence: Synthetic Native
                         peptide sequence
source                  1..14
                        mol_type = protein
                        organism = synthetic construct
SEQUENCE: 49
CGHSENFFFI EVGR                                                             14

SEQ ID NO: 50           moltype = AA  length = 27
FEATURE                 Location/Qualifiers
REGION                  1..27
                        note = Description of Artificial Sequence: Synthetic Native
                         peptide sequence
MOD_RES                 1
                        note = Carbamidomethylation
source                  1..27
                        mol_type = protein
                        organism = synthetic construct
SEQUENCE: 50
CTPGTGLGTS PALAGDEAAS AADLDNR                                               27

SEQ ID NO: 51           moltype = AA  length = 27
FEATURE                 Location/Qualifiers
REGION                  1..27
                        note = Description of Artificial Sequence: Synthetic Native
                         peptide sequence
source                  1..27
                        mol_type = protein
                        organism = synthetic construct
SEQUENCE: 51
CTPGTGLGTS PALAGDEAAS AADLDNR                                               27

SEQ ID NO: 52           moltype = AA  length = 15
FEATURE                 Location/Qualifiers
REGION                  1..15
                        note = Description of Artificial Sequence: Synthetic Native
                         peptide sequence
source                  1..15
                        mol_type = protein
                        organism = synthetic construct
```

```
SEQUENCE: 52
HHLNNPPPSQ VGLTR                                                           15

SEQ ID NO: 53            moltype = AA  length = 14
FEATURE                  Location/Qualifiers
REGION                   1..14
                         note = Description of Artificial Sequence: Synthetic Native
                          peptide sequence
source                   1..14
                         mol_type = protein
                         organism = synthetic construct
SEQUENCE: 53
HSSETFSSTP SATR                                                            14

SEQ ID NO: 54            moltype = AA  length = 12
FEATURE                  Location/Qualifiers
REGION                   1..12
                         note = Description of Artificial Sequence: Synthetic Native
                          peptide sequence
source                   1..12
                         mol_type = protein
                         organism = synthetic construct
SEQUENCE: 54
KGSGDYMPMS PK                                                              12

SEQ ID NO: 55            moltype = AA  length = 21
FEATURE                  Location/Qualifiers
REGION                   1..21
                         note = Description of Artificial Sequence: Synthetic Native
                          peptide sequence
MOD_RES                  2
                         note = Carbamidomethylation
source                   1..21
                         mol_type = protein
                         organism = synthetic construct
SEQUENCE: 55
LCGAAGGLEN GLNYIDLDLV K                                                    21

SEQ ID NO: 56            moltype = AA  length = 21
FEATURE                  Location/Qualifiers
REGION                   1..21
                         note = Description of Artificial Sequence: Synthetic Native
                          peptide sequence
source                   1..21
                         mol_type = protein
                         organism = synthetic construct
SEQUENCE: 56
LCGAAGGLEN GLNYIDLDLV K                                                    21

SEQ ID NO: 57            moltype = AA  length = 13
FEATURE                  Location/Qualifiers
REGION                   1..13
                         note = Description of Artificial Sequence: Synthetic Native
                          peptide sequence
source                   1..13
                         mol_type = protein
                         organism = synthetic construct
SEQUENCE: 57
SVSAPQQIIN PIR                                                             13

SEQ ID NO: 58            moltype = AA  length = 21
FEATURE                  Location/Qualifiers
REGION                   1..21
                         note = Description of Artificial Sequence: Synthetic Native
                          peptide sequence
source                   1..21
                         mol_type = protein
                         organism = synthetic construct
SEQUENCE: 58
TESITATSPA SMVGGKPGSF R                                                    21

SEQ ID NO: 59            moltype = AA  length = 12
FEATURE                  Location/Qualifiers
REGION                   1..12
                         note = Description of Artificial Sequence: Synthetic Native
                          peptide sequence
source                   1..12
                         mol_type = protein
                         organism = synthetic construct
```

```
SEQUENCE: 59
TGIAAEEVSL PR                                                                                12

SEQ ID NO: 60           moltype = AA   length = 14
FEATURE                 Location/Qualifiers
REGION                  1..14
                        note = Description of Artificial Sequence: Synthetic Native
                         peptide sequence
source                  1..14
                        mol_type = protein
                        organism = synthetic construct
SEQUENCE: 60
SYPEEGLEMH PLER                                                                              14

SEQ ID NO: 61           moltype = AA   length = 14
FEATURE                 Location/Qualifiers
REGION                  1..14
                        note = Description of Artificial Sequence: Synthetic Native
                         peptide sequence
source                  1..14
                        mol_type = protein
                        organism = synthetic construct
SEQUENCE: 61
THSAGTSPTI THQK                                                                              14

SEQ ID NO: 62           moltype = AA   length = 26
FEATURE                 Location/Qualifiers
REGION                  1..26
                        note = Description of Artificial Sequence: Synthetic Native
                         peptide sequence
MOD_RES                 3
                        note = Phosphorylation
source                  1..26
                        mol_type = protein
                        organism = synthetic construct
SEQUENCE: 62
ASSDGEGTMS RPASVDGSPV SPSTNR                                                                 26

SEQ ID NO: 63           moltype = AA   length = 14
FEATURE                 Location/Qualifiers
REGION                  1..14
                        note = Description of Artificial Sequence: Synthetic Native
                         peptide sequence
MOD_RES                 3
                        note = Phosphorylation
source                  1..14
                        mol_type = protein
                        organism = synthetic construct
SEQUENCE: 63
HSSETFSSTP SATR                                                                              14

SEQ ID NO: 64           moltype = AA   length = 12
FEATURE                 Location/Qualifiers
REGION                  1..12
                        note = Description of Artificial Sequence: Synthetic Native
                         peptide sequence
MOD_RES                 10
                        note = Phosphorylation
source                  1..12
                        mol_type = protein
                        organism = synthetic construct
SEQUENCE: 64
KGSGDYMPMS PK                                                                                12

SEQ ID NO: 65           moltype = AA   length = 12
FEATURE                 Location/Qualifiers
REGION                  1..12
                        note = Description of Artificial Sequence: Synthetic Native
                         peptide sequence
MOD_RES                 7
                        note = Methionine sulfoxide
MOD_RES                 9
                        note = Methionine sulfoxide
MOD_RES                 10
                        note = Phosphorylation
source                  1..12
                        mol_type = protein
                        organism = synthetic construct
SEQUENCE: 65
```

```
KGSGDYMPMS PK                                                                  12

SEQ ID NO: 66           moltype = AA  length = 21
FEATURE                 Location/Qualifiers
REGION                  1..21
                        note = Description of Artificial Sequence: Synthetic Native
                         peptide sequence
MOD_RES                 2
                        note = Carbamidomethylation
MOD_RES                 14
                        note = Phosphorylation
source                  1..21
                        mol_type = protein
                        organism = synthetic construct
SEQUENCE: 66
LCGAAGGLEN GLNYIDLDLV K                                                        21

SEQ ID NO: 67           moltype = AA  length = 21
FEATURE                 Location/Qualifiers
REGION                  1..21
                        note = Description of Artificial Sequence: Synthetic Native
                         peptide sequence
MOD_RES                 14
                        note = Phosphorylation
source                  1..21
                        mol_type = protein
                        organism = synthetic construct
SEQUENCE: 67
LCGAAGGLEN GLNYIDLDLV K                                                        21

SEQ ID NO: 68           moltype = AA  length = 21
FEATURE                 Location/Qualifiers
REGION                  1..21
                        note = Description of Artificial Sequence: Synthetic Native
                         peptide sequence
MOD_RES                 8
                        note = Phosphorylation
source                  1..21
                        mol_type = protein
                        organism = synthetic construct
SEQUENCE: 68
TESITATSPA SMVGGKPGSF R                                                        21

SEQ ID NO: 69           moltype = AA  length = 21
FEATURE                 Location/Qualifiers
REGION                  1..21
                        note = Description of Artificial Sequence: Synthetic Native
                         peptide sequence
MOD_RES                 8
                        note = Phosphorylation
MOD_RES                 12
                        note = Methionine sulfoxide
source                  1..21
                        mol_type = protein
                        organism = synthetic construct
SEQUENCE: 69
TESITATSPA SMVGGKPGSF R                                                        21

SEQ ID NO: 70           moltype = AA  length = 18
FEATURE                 Location/Qualifiers
REGION                  1..18
                        note = Description of Artificial Sequence: Synthetic Native
                         peptide sequence
source                  1..18
                        mol_type = protein
                        organism = synthetic construct
SEQUENCE: 70
APAQTPAEPT PGYEVGQR                                                            18

SEQ ID NO: 71           moltype = AA  length = 15
FEATURE                 Location/Qualifiers
REGION                  1..15
                        note = Description of Artificial Sequence: Synthetic Native
                         peptide sequence
source                  1..15
                        mol_type = protein
                        organism = synthetic construct
SEQUENCE: 71
DSFRARSTSL NERPK                                                               15
```

```
SEQ ID NO: 72              moltype = AA   length = 16
FEATURE                    Location/Qualifiers
REGION                     1..16
                           note = Description of Artificial Sequence: Synthetic Native
                            peptide sequence
source                     1..16
                           mol_type = protein
                           organism = synthetic construct
SEQUENCE: 72
EAPAKLESQA GQQVSR                                                          16

SEQ ID NO: 73              moltype = AA   length = 11
FEATURE                    Location/Qualifiers
REGION                     1..11
                           note = Description of Artificial Sequence: Synthetic Native
                            peptide sequence
source                     1..11
                           mol_type = protein
                           organism = synthetic construct
SEQUENCE: 73
GYTISDSAPS R                                                               11

SEQ ID NO: 74              moltype = AA   length = 12
FEATURE                    Location/Qualifiers
REGION                     1..12
                           note = Description of Artificial Sequence: Synthetic Native
                            peptide sequence
source                     1..12
                           mol_type = protein
                           organism = synthetic construct
SEQUENCE: 74
LISSVEDFTE FV                                                              12

SEQ ID NO: 75              moltype = AA   length = 13
FEATURE                    Location/Qualifiers
REGION                     1..13
                           note = Description of Artificial Sequence: Synthetic Native
                            peptide sequence
source                     1..13
                           mol_type = protein
                           organism = synthetic construct
SEQUENCE: 75
LVTVTTSVGT GTR                                                             13

SEQ ID NO: 76              moltype = AA   length = 21
FEATURE                    Location/Qualifiers
REGION                     1..21
                           note = Description of Artificial Sequence: Synthetic Native
                            peptide sequence
source                     1..21
                           mol_type = protein
                           organism = synthetic construct
SEQUENCE: 76
SQSGTLDGES AAWSASGEDS R                                                    21

SEQ ID NO: 77              moltype = AA   length = 15
FEATURE                    Location/Qualifiers
REGION                     1..15
                           note = Description of Artificial Sequence: Synthetic Native
                            peptide sequence
source                     1..15
                           mol_type = protein
                           organism = synthetic construct
SEQUENCE: 77
SVQLLDQIPS YDTHK                                                           15

SEQ ID NO: 78              moltype = AA   length = 21
FEATURE                    Location/Qualifiers
REGION                     1..21
                           note = Description of Artificial Sequence: Synthetic Native
                            peptide sequence
source                     1..21
                           mol_type = protein
                           organism = synthetic construct
SEQUENCE: 78
VGALDVPASQ FLGSATSPGP R                                                    21

SEQ ID NO: 79              moltype = AA   length = 23
```

```
FEATURE                 Location/Qualifiers
REGION                  1..23
                        note = Description of Artificial Sequence: Synthetic Native
                         peptide sequence
source                  1..23
                        mol_type = protein
                        organism = synthetic construct
SEQUENCE: 79
VVSSEGGRPS VDLSFQPSQP LSK                                                  23

SEQ ID NO: 80           moltype = AA  length = 10
FEATURE                 Location/Qualifiers
REGION                  1..10
                        note = Description of Artificial Sequence: Synthetic Native
                         peptide sequence
source                  1..10
                        mol_type = protein
                        organism = synthetic construct
SEQUENCE: 80
YTEFLTGLGR                                                                 10

SEQ ID NO: 81           moltype = AA  length = 11
FEATURE                 Location/Qualifiers
REGION                  1..11
                        note = Description of Artificial Sequence: Synthetic Native
                         peptide sequence
source                  1..11
                        mol_type = protein
                        organism = synthetic construct
SEQUENCE: 81
YVFSNFTAVP K                                                               11

SEQ ID NO: 82           moltype = AA  length = 10
FEATURE                 Location/Qualifiers
REGION                  1..10
                        note = Description of Artificial Sequence: Synthetic Native
                         peptide sequence
source                  1..10
                        mol_type = protein
                        organism = synthetic construct
SEQUENCE: 82
SNPTDIYPSK                                                                 10

SEQ ID NO: 83           moltype = AA  length = 12
FEATURE                 Location/Qualifiers
REGION                  1..12
                        note = Description of Artificial Sequence: Synthetic Native
                         peptide sequence
source                  1..12
                        mol_type = protein
                        organism = synthetic construct
SEQUENCE: 83
FNSCYLDEYI AR                                                              12

SEQ ID NO: 84           moltype = AA  length = 13
FEATURE                 Location/Qualifiers
REGION                  1..13
                        note = Description of Artificial Sequence: Synthetic Native
                         peptide sequence
source                  1..13
                        mol_type = protein
                        organism = synthetic construct
SEQUENCE: 84
GQPEGPLPSS SPR                                                             13

SEQ ID NO: 85           moltype = AA  length = 25
FEATURE                 Location/Qualifiers
REGION                  1..25
                        note = Description of Artificial Sequence: Synthetic Native
                         peptide sequence
source                  1..25
                        mol_type = protein
                        organism = synthetic construct
SEQUENCE: 85
SLLGLDSGEL QSGPESSSSP GVHVR                                                25

SEQ ID NO: 86           moltype = AA  length = 15
FEATURE                 Location/Qualifiers
REGION                  1..15
```

```
                        note = Description of Artificial Sequence: Synthetic Native
                         peptide sequence
MOD_RES                 9
                        note = Phosphorylation
source                  1..15
                        mol_type = protein
                        organism = synthetic construct
SEQUENCE: 86
DSFRARSTSL NERPK                                                            15

SEQ ID NO: 87           moltype = AA   length = 11
FEATURE                 Location/Qualifiers
REGION                  1..11
                        note = Description of Artificial Sequence: Synthetic Native
                         peptide sequence
MOD_RES                 3
                        note = Phosphorylation
source                  1..11
                        mol_type = protein
                        organism = synthetic construct
SEQUENCE: 87
GYTISDSAPS R                                                                11

SEQ ID NO: 88           moltype = AA   length = 12
FEATURE                 Location/Qualifiers
REGION                  1..12
                        note = Description of Artificial Sequence: Synthetic Native
                         peptide sequence
MOD_RES                 3
                        note = Phosphorylation
source                  1..12
                        mol_type = protein
                        organism = synthetic construct
SEQUENCE: 88
LISSVEDFTE FV                                                               12

SEQ ID NO: 89           moltype = AA   length = 12
FEATURE                 Location/Qualifiers
REGION                  1..12
                        note = Description of Artificial Sequence: Synthetic Native
                         peptide sequence
MOD_RES                 4
                        note = Phosphorylation
source                  1..12
                        mol_type = protein
                        organism = synthetic construct
SEQUENCE: 89
LISSVEDFTE FV                                                               12

SEQ ID NO: 90           moltype = AA   length = 12
FEATURE                 Location/Qualifiers
REGION                  1..12
                        note = Description of Artificial Sequence: Synthetic Native
                         peptide sequence
MOD_RES                 3..4
                        note = Phosphorylation
source                  1..12
                        mol_type = protein
                        organism = synthetic construct
SEQUENCE: 90
LISSVEDFTE FV                                                               12

SEQ ID NO: 91           moltype = AA   length = 9
FEATURE                 Location/Qualifiers
REGION                  1..9
                        note = Description of Artificial Sequence: Synthetic Native
                         peptide sequence
MOD_RES                 3
                        note = Phosphorylation
source                  1..9
                        mol_type = protein
                        organism = synthetic construct
SEQUENCE: 91
STSLNERPK                                                                    9

SEQ ID NO: 92           moltype = AA   length = 9
FEATURE                 Location/Qualifiers
REGION                  1..9
                        note = Description of Artificial Sequence: Synthetic Native
```

```
                                peptide sequence
source                          1..9
                                mol_type = protein
                                organism = synthetic construct
SEQUENCE: 92
STSLNERPK                                                                         9

SEQ ID NO: 93                   moltype = AA   length = 19
FEATURE                         Location/Qualifiers
REGION                          1..19
                                note = Description of Artificial Sequence: Synthetic Native
                                peptide sequence
MOD_RES                         16
                                note = Carbamidomethylation
source                          1..19
                                mol_type = protein
                                organism = synthetic construct
SEQUENCE: 93
AVLALHQDLF SLAQQCIDK                                                              19

SEQ ID NO: 94                   moltype = AA   length = 19
FEATURE                         Location/Qualifiers
REGION                          1..19
                                note = Description of Artificial Sequence: Synthetic Native
                                peptide sequence
source                          1..19
                                mol_type = protein
                                organism = synthetic construct
SEQUENCE: 94
AVLALHQDLF SLAQQCIDK                                                              19

SEQ ID NO: 95                   moltype = AA   length = 18
FEATURE                         Location/Qualifiers
REGION                          1..18
                                note = Description of Artificial Sequence: Synthetic Native
                                peptide sequence
source                          1..18
                                mol_type = protein
                                organism = synthetic construct
SEQUENCE: 95
DLELAVPGTY DPNQPIIR                                                               18

SEQ ID NO: 96                   moltype = AA   length = 9
FEATURE                         Location/Qualifiers
REGION                          1..9
                                note = Description of Artificial Sequence: Synthetic Native
                                peptide sequence
source                          1..9
                                mol_type = protein
                                organism = synthetic construct
SEQUENCE: 96
GNNLQDTLR                                                                         9

SEQ ID NO: 97                   moltype = AA   length = 16
FEATURE                         Location/Qualifiers
REGION                          1..16
                                note = Description of Artificial Sequence: Synthetic Native
                                peptide sequence
source                          1..16
                                mol_type = protein
                                organism = synthetic construct
SEQUENCE: 97
GPTPAILESL ISINNK                                                                 16

SEQ ID NO: 98                   moltype = AA   length = 17
FEATURE                         Location/Qualifiers
REGION                          1..17
                                note = Description of Artificial Sequence: Synthetic Native
                                peptide sequence
source                          1..17
                                mol_type = protein
                                organism = synthetic construct
SEQUENCE: 98
GYTLADEEED PLIYQHR                                                                17

SEQ ID NO: 99                   moltype = AA   length = 13
FEATURE                         Location/Qualifiers
REGION                          1..13
                                note = Description of Artificial Sequence: Synthetic Native
```

```
                            peptide sequence
source                      1..13
                            mol_type = protein
                            organism = synthetic construct
SEQUENCE: 99
IHGALLILNE LVR                                                              13

SEQ ID NO: 100              moltype = AA  length = 14
FEATURE                     Location/Qualifiers
REGION                      1..14
                            note = Description of Artificial Sequence: Synthetic Native
                            peptide sequence
source                      1..14
                            mol_type = protein
                            organism = synthetic construct
SEQUENCE: 100
IQSIAPSLQV ITSK                                                             14

SEQ ID NO: 101              moltype = AA  length = 12
FEATURE                     Location/Qualifiers
REGION                      1..12
                            note = Description of Artificial Sequence: Synthetic Native
                            peptide sequence
source                      1..12
                            mol_type = protein
                            organism = synthetic construct
SEQUENCE: 101
LFDAPEAPLP SR                                                               12

SEQ ID NO: 102              moltype = AA  length = 18
FEATURE                     Location/Qualifiers
REGION                      1..18
                            note = Description of Artificial Sequence: Synthetic Native
                            peptide sequence
source                      1..18
                            mol_type = protein
                            organism = synthetic construct
SEQUENCE: 102
LGEWQLNLQG INESTIPK                                                         18

SEQ ID NO: 103              moltype = AA  length = 11
FEATURE                     Location/Qualifiers
REGION                      1..11
                            note = Description of Artificial Sequence: Synthetic Native
                            peptide sequence
source                      1..11
                            mol_type = protein
                            organism = synthetic construct
SEQUENCE: 103
LIHQLLTDIG R                                                                11

SEQ ID NO: 104              moltype = AA  length = 10
FEATURE                     Location/Qualifiers
REGION                      1..10
                            note = Description of Artificial Sequence: Synthetic Native
                            peptide sequence
source                      1..10
                            mol_type = protein
                            organism = synthetic construct
SEQUENCE: 104
SPSSEVWFDR                                                                  10

SEQ ID NO: 105              moltype = AA  length = 24
FEATURE                     Location/Qualifiers
REGION                      1..24
                            note = Description of Artificial Sequence: Synthetic Native
                            peptide sequence
source                      1..24
                            mol_type = protein
                            organism = synthetic construct
SEQUENCE: 105
TDSYSAGQSV EILDGVELGE PAHK                                                  24

SEQ ID NO: 106              moltype = AA  length = 12
FEATURE                     Location/Qualifiers
REGION                      1..12
                            note = Description of Artificial Sequence: Synthetic Native
                            peptide sequence
source                      1..12
```

```
SEQUENCE: 106
TLVLLLGVDP SR                                                      12

SEQ ID NO: 107         moltype = AA   length = 18
FEATURE                Location/Qualifiers
REGION                 1..18
                       note = Description of Artificial Sequence: Synthetic Native
                        peptide sequence
source                 1..18
                       mol_type = protein
                       organism = synthetic construct
SEQUENCE: 107
VEVFEHAVNN TAGDDLAK                                                18

SEQ ID NO: 108         moltype = AA   length = 12
FEATURE                Location/Qualifiers
REGION                 1..12
                       note = Description of Artificial Sequence: Synthetic Native
                        peptide sequence
source                 1..12
                       mol_type = protein
                       organism = synthetic construct
SEQUENCE: 108
VLGLLGALDP YK                                                      12

SEQ ID NO: 109         moltype = AA   length = 11
FEATURE                Location/Qualifiers
REGION                 1..11
                       note = Description of Artificial Sequence: Synthetic Native
                        peptide sequence
source                 1..11
                       mol_type = protein
                       organism = synthetic construct
SEQUENCE: 109
WTLVNDETQA K                                                       11

SEQ ID NO: 110         moltype = AA   length = 10
FEATURE                Location/Qualifiers
REGION                 1..10
                       note = Description of Artificial Sequence: Synthetic Native
                        peptide sequence
source                 1..10
                       mol_type = protein
                       organism = synthetic construct
SEQUENCE: 110
ETSFNQAYGR                                                         10

SEQ ID NO: 111         moltype = AA   length = 9
FEATURE                Location/Qualifiers
REGION                 1..9
                       note = Description of Artificial Sequence: Synthetic Native
                        peptide sequence
source                 1..9
                       mol_type = protein
                       organism = synthetic construct
SEQUENCE: 111
TLDQSPELR                                                          9

SEQ ID NO: 112         moltype = AA   length = 24
FEATURE                Location/Qualifiers
REGION                 1..24
                       note = Description of Artificial Sequence: Synthetic Native
                        peptide sequence
MOD_RES                3
                       note = Phosphorylation
source                 1..24
                       mol_type = protein
                       organism = synthetic construct
SEQUENCE: 112
TDSYSAGQSV EILDGVELGE PAHK                                         24

SEQ ID NO: 113         moltype = AA   length = 24
FEATURE                Location/Qualifiers
REGION                 1..24
                       note = Description of Artificial Sequence: Synthetic Native
                        peptide sequence
MOD_RES                1
```

```
                              note = Phosphorylation
source                        1..24
                              mol_type = protein
                              organism = synthetic construct
SEQUENCE: 113
TDSYSAGQSV EILDGVELGE PAHK                                                24

SEQ ID NO: 114                moltype = AA  length = 24
FEATURE                       Location/Qualifiers
REGION                        1..24
                              note = Description of Artificial Sequence: Synthetic Native
                               peptide sequence
MOD_RES                       1
                              note = Phosphorylation
MOD_RES                       3
                              note = Phosphorylation
source                        1..24
                              mol_type = protein
                              organism = synthetic construct
SEQUENCE: 114
TDSYSAGQSV EILDGVELGE PAHK                                                24

SEQ ID NO: 115                moltype = AA  length = 17
FEATURE                       Location/Qualifiers
REGION                        1..17
                              note = Description of Artificial Sequence: Synthetic Native
                               peptide sequence
source                        1..17
                              mol_type = protein
                              organism = synthetic construct
SEQUENCE: 115
DIKPQNLLVD PDTAVLK                                                        17

SEQ ID NO: 116                moltype = AA  length = 16
FEATURE                       Location/Qualifiers
REGION                        1..16
                              note = Description of Artificial Sequence: Synthetic Native
                               peptide sequence
MOD_RES                       7
                              note = Carbamidomethylation
source                        1..16
                              mol_type = protein
                              organism = synthetic construct
SEQUENCE: 116
LSPLEACAHS FFDELR                                                         16

SEQ ID NO: 117                moltype = AA  length = 16
FEATURE                       Location/Qualifiers
REGION                        1..16
                              note = Description of Artificial Sequence: Synthetic Native
                               peptide sequence
source                        1..16
                              mol_type = protein
                              organism = synthetic construct
SEQUENCE: 117
LSPLEACAHS FFDELR                                                         16

SEQ ID NO: 118                moltype = AA  length = 13
FEATURE                       Location/Qualifiers
REGION                        1..13
                              note = Description of Artificial Sequence: Synthetic Native
                               peptide sequence
MOD_RES                       11
                              note = Carbamidomethylation
source                        1..13
                              mol_type = protein
                              organism = synthetic construct
SEQUENCE: 118
SLAYIHSQGV CHR                                                            13

SEQ ID NO: 119                moltype = AA  length = 13
FEATURE                       Location/Qualifiers
REGION                        1..13
                              note = Description of Artificial Sequence: Synthetic Native
                               peptide sequence
source                        1..13
                              mol_type = protein
                              organism = synthetic construct
SEQUENCE: 119
```

SLAYIHSQGV CHR                                                            13

SEQ ID NO: 120         moltype = AA  length = 10
FEATURE                Location/Qualifiers
REGION                 1..10
                       note = Description of Artificial Sequence: Synthetic Native
                        peptide sequence
source                 1..10
                       mol_type = protein
                       organism = synthetic construct
SEQUENCE: 120
SQEVAYTDIK                                                                10

SEQ ID NO: 121         moltype = AA  length = 20
FEATURE                Location/Qualifiers
REGION                 1..20
                       note = Description of Artificial Sequence: Synthetic Native
                        peptide sequence
MOD_RES                9
                       note = Carbamidomethylation
source                 1..20
                       mol_type = protein
                       organism = synthetic construct
SEQUENCE: 121
TPPEAIALCS SLLEYTPSSR                                                     20

SEQ ID NO: 122         moltype = AA  length = 20
FEATURE                Location/Qualifiers
REGION                 1..20
                       note = Description of Artificial Sequence: Synthetic Native
                        peptide sequence
source                 1..20
                       mol_type = protein
                       organism = synthetic construct
SEQUENCE: 122
TPPEAIALCS SLLEYTPSSR                                                     20

SEQ ID NO: 123         moltype = AA  length = 32
FEATURE                Location/Qualifiers
REGION                 1..32
                       note = Description of Artificial Sequence: Synthetic Native
                        peptide sequence
source                 1..32
                       mol_type = protein
                       organism = synthetic construct
SEQUENCE: 123
TSSFAEPGGG GGGGGGPGG SASGPGGTGG GK                                        32

SEQ ID NO: 124         moltype = AA  length = 14
FEATURE                Location/Qualifiers
REGION                 1..14
                       note = Description of Artificial Sequence: Synthetic Native
                        peptide sequence
source                 1..14
                       mol_type = protein
                       organism = synthetic construct
SEQUENCE: 124
VTTVVATLGQ GPER                                                           14

SEQ ID NO: 125         moltype = AA  length = 18
FEATURE                Location/Qualifiers
REGION                 1..18
                       note = Description of Artificial Sequence: Synthetic Native
                        peptide sequence
source                 1..18
                       mol_type = protein
                       organism = synthetic construct
SEQUENCE: 125
DSGKVTTVVA TLGQGPER                                                       18

SEQ ID NO: 126         moltype = AA  length = 9
FEATURE                Location/Qualifiers
REGION                 1..9
                       note = Description of Artificial Sequence: Synthetic Native
                        peptide sequence
source                 1..9
                       mol_type = protein
                       organism = synthetic construct
SEQUENCE: 126

```
YFFYSSGEK                                                             9

SEQ ID NO: 127          moltype = AA  length = 32
FEATURE                 Location/Qualifiers
REGION                  1..32
                        note = Description of Artificial Sequence: Synthetic Native
                         peptide sequence
MOD_RES                 3
                        note = Phosphorylation
source                  1..32
                        mol_type = protein
                        organism = synthetic construct
SEQUENCE: 127
TSSFAEPGGG GGGGGGGPGG SASGPGGTGG GK                                   32

SEQ ID NO: 128          moltype = AA  length = 18
FEATURE                 Location/Qualifiers
REGION                  1..18
                        note = Description of Artificial Sequence: Synthetic Native
                         peptide sequence
source                  1..18
                        mol_type = protein
                        organism = synthetic construct
SEQUENCE: 128
DEVYLNLVLD YVPETVYR                                                   18

SEQ ID NO: 129          moltype = AA  length = 17
FEATURE                 Location/Qualifiers
REGION                  1..17
                        note = Description of Artificial Sequence: Synthetic Native
                         peptide sequence
source                  1..17
                        mol_type = protein
                        organism = synthetic construct
SEQUENCE: 129
DIKPQNLLLD PDTAVLK                                                    17

SEQ ID NO: 130          moltype = AA  length = 29
FEATURE                 Location/Qualifiers
REGION                  1..29
                        note = Description of Artificial Sequence: Synthetic Native
                         peptide sequence
source                  1..29
                        mol_type = protein
                        organism = synthetic construct
SEQUENCE: 130
DTPALFNFTT QELSSNPPLA TILIPPHAR                                       29

SEQ ID NO: 131          moltype = AA  length = 11
FEATURE                 Location/Qualifiers
REGION                  1..11
                        note = Description of Artificial Sequence: Synthetic Native
                         peptide sequence
MOD_RES                 2
                        note = Carbamidomethylation
source                  1..11
                        mol_type = protein
                        organism = synthetic construct
SEQUENCE: 131
LCDSGELVAI K                                                          11

SEQ ID NO: 132          moltype = AA  length = 11
FEATURE                 Location/Qualifiers
REGION                  1..11
                        note = Description of Artificial Sequence: Synthetic Native
                         peptide sequence
source                  1..11
                        mol_type = protein
                        organism = synthetic construct
SEQUENCE: 132
LCDSGELVAI K                                                          11

SEQ ID NO: 133          moltype = AA  length = 9
FEATURE                 Location/Qualifiers
REGION                  1..9
                        note = Description of Artificial Sequence: Synthetic Native
                         peptide sequence
source                  1..9
                        mol_type = protein
```

-continued

```
                              organism = synthetic construct
SEQUENCE: 133
LLEYTPTAR                                                                          9

SEQ ID NO: 134         moltype = AA   length = 13
FEATURE                Location/Qualifiers
REGION                 1..13
                       note = Description of Artificial Sequence: Synthetic Native
                        peptide sequence
MOD_RES                11
                       note = Carbamidomethylation
source                 1..13
                       mol_type = protein
                       organism = synthetic construct
SEQUENCE: 134
SLAYIHSFGI CHR                                                                    13

SEQ ID NO: 135         moltype = AA   length = 13
FEATURE                Location/Qualifiers
REGION                 1..13
                       note = Description of Artificial Sequence: Synthetic Native
                        peptide sequence
source                 1..13
                       mol_type = protein
                       organism = synthetic construct
SEQUENCE: 135
SLAYIHSFGI CHR                                                                    13

SEQ ID NO: 136         moltype = AA   length = 21
FEATURE                Location/Qualifiers
REGION                 1..21
                       note = Description of Artificial Sequence: Synthetic Native
                        peptide sequence
MOD_RES                8
                       note = Carbamidomethylation
source                 1..21
                       mol_type = protein
                       organism = synthetic construct
SEQUENCE: 136
TTSFAESCKP VQQPSAFGSM K                                                           21

SEQ ID NO: 137         moltype = AA   length = 21
FEATURE                Location/Qualifiers
REGION                 1..21
                       note = Description of Artificial Sequence: Synthetic Native
                        peptide sequence
source                 1..21
                       mol_type = protein
                       organism = synthetic construct
SEQUENCE: 137
TTSFAESCKP VQQPSAFGSM K                                                           21

SEQ ID NO: 138         moltype = AA   length = 21
FEATURE                Location/Qualifiers
REGION                 1..21
                       note = Description of Artificial Sequence: Synthetic Native
                        peptide sequence
MOD_RES                8
                       note = Carbamidomethylation
MOD_RES                20
                       note = Methionine sulfoxide
source                 1..21
                       mol_type = protein
                       organism = synthetic construct
SEQUENCE: 138
TTSFAESCKP VQQPSAFGSM K                                                           21

SEQ ID NO: 139         moltype = AA   length = 21
FEATURE                Location/Qualifiers
REGION                 1..21
                       note = Description of Artificial Sequence: Synthetic Native
                        peptide sequence
MOD_RES                20
                       note = Methionine sulfoxide
source                 1..21
                       mol_type = protein
                       organism = synthetic construct
SEQUENCE: 139
TTSFAESCKP VQQPSAFGSM K                                                           21
```

```
SEQ ID NO: 140           moltype = AA   length = 24
FEATURE                  Location/Qualifiers
REGION                   1..24
                         note = Description of Artificial Sequence: Synthetic Native
                          peptide sequence
source                   1..24
                         mol_type = protein
                         organism = synthetic construct
SEQUENCE: 140
VTTVVATPGQ GPDRPQEVSY TDTK                                              24

SEQ ID NO: 141           moltype = AA   length = 9
FEATURE                  Location/Qualifiers
REGION                   1..9
                         note = Description of Artificial Sequence: Synthetic Native
                          peptide sequence
source                   1..9
                         mol_type = protein
                         organism = synthetic construct
SEQUENCE: 141
KLDHCNIVR                                                                9

SEQ ID NO: 142           moltype = AA   length = 13
FEATURE                  Location/Qualifiers
REGION                   1..13
                         note = Description of Artificial Sequence: Synthetic Native
                          peptide sequence
source                   1..13
                         mol_type = protein
                         organism = synthetic construct
SEQUENCE: 142
DSSGTGHFTS GVR                                                          13

SEQ ID NO: 143           moltype = AA   length = 21
FEATURE                  Location/Qualifiers
REGION                   1..21
                         note = Description of Artificial Sequence: Synthetic Native
                          peptide sequence
MOD_RES                  3
                         note = Phosphorylation
MOD_RES                  8
                         note = Carbamidomethylation
MOD_RES                  20
                         note = Methionine sulfoxide
source                   1..21
                         mol_type = protein
                         organism = synthetic construct
SEQUENCE: 143
TTSFAESCKP VQQPSAFGSM K                                                 21

SEQ ID NO: 144           moltype = AA   length = 21
FEATURE                  Location/Qualifiers
REGION                   1..21
                         note = Description of Artificial Sequence: Synthetic Native
                          peptide sequence
MOD_RES                  3
                         note = Phosphorylation
MOD_RES                  20
                         note = Methionine sulfoxide
source                   1..21
                         mol_type = protein
                         organism = synthetic construct
SEQUENCE: 144
TTSFAESCKP VQQPSAFGSM K                                                 21

SEQ ID NO: 145           moltype = AA   length = 21
FEATURE                  Location/Qualifiers
REGION                   1..21
                         note = Description of Artificial Sequence: Synthetic Native
                          peptide sequence
MOD_RES                  3
                         note = Phosphorylation
MOD_RES                  8
                         note = Carbamidomethylation
source                   1..21
                         mol_type = protein
                         organism = synthetic construct
SEQUENCE: 145
```

```
TTSFAESCKP VQQPSAFGSM K                                                21

SEQ ID NO: 146           moltype = AA   length = 21
FEATURE                  Location/Qualifiers
REGION                   1..21
                         note = Description of Artificial Sequence: Synthetic Native
                          peptide sequence
MOD_RES                  3
                         note = Phosphorylation
source                   1..21
                         mol_type = protein
                         organism = synthetic construct
SEQUENCE: 146
TTSFAESCKP VQQPSAFGSM K                                                21

SEQ ID NO: 147           moltype = AA   length = 11
FEATURE                  Location/Qualifiers
REGION                   1..11
                         note = Description of Artificial Sequence: Synthetic Native
                          peptide sequence
MOD_RES                  9
                         note = Carbamidomethylation
source                   1..11
                         mol_type = protein
                         organism = synthetic construct
SEQUENCE: 147
GEPNVSYICS R                                                           11

SEQ ID NO: 148           moltype = AA   length = 11
FEATURE                  Location/Qualifiers
REGION                   1..11
                         note = Description of Artificial Sequence: Synthetic Native
                          peptide sequence
source                   1..11
                         mol_type = protein
                         organism = synthetic construct
SEQUENCE: 148
GEPNVSYICS R                                                           11

SEQ ID NO: 149           moltype = AA   length = 11
FEATURE                  Location/Qualifiers
REGION                   1..11
                         note = Description of Artificial Sequence: Synthetic Native
                          peptide sequence
MOD_RES                  7
                         note = Phosphorylation
MOD_RES                  9
                         note = Carbamidomethylation
source                   1..11
                         mol_type = protein
                         organism = synthetic construct
SEQUENCE: 149
GEPNVSYICS R                                                           11

SEQ ID NO: 150           moltype = AA   length = 11
FEATURE                  Location/Qualifiers
REGION                   1..11
                         note = Description of Artificial Sequence: Synthetic Native
                          peptide sequence
MOD_RES                  7
                         note = Phosphorylation
source                   1..11
                         mol_type = protein
                         organism = synthetic construct
SEQUENCE: 150
GEPNVSYICS R                                                           11

SEQ ID NO: 151           moltype = AA   length = 11
FEATURE                  Location/Qualifiers
REGION                   1..11
                         note = Description of Artificial Sequence: Synthetic Native
                          peptide sequence
MOD_RES                  6
                         note = Phosphorylation
MOD_RES                  9
                         note = Carbamidomethylation
source                   1..11
                         mol_type = protein
                         organism = synthetic construct
```

```
SEQUENCE: 151
GEPNVSYICS R                                                                       11

SEQ ID NO: 152            moltype = AA   length = 11
FEATURE                   Location/Qualifiers
REGION                    1..11
                          note = Description of Artificial Sequence: Synthetic Native
                           peptide sequence
MOD_RES                   6
                          note = Phosphorylation
source                    1..11
                          mol_type = protein
                          organism = synthetic construct
SEQUENCE: 152
GEPNVSYICS R                                                                       11

SEQ ID NO: 153            moltype = AA   length = 11
FEATURE                   Location/Qualifiers
REGION                    1..11
                          note = Description of Artificial Sequence: Synthetic Native
                           peptide sequence
MOD_RES                   6..7
                          note = Phosphorylation
MOD_RES                   9
                          note = Carbamidomethylation
source                    1..11
                          mol_type = protein
                          organism = synthetic construct
SEQUENCE: 153
GEPNVSYICS R                                                                       11

SEQ ID NO: 154            moltype = AA   length = 11
FEATURE                   Location/Qualifiers
REGION                    1..11
                          note = Description of Artificial Sequence: Synthetic Native
                           peptide sequence
MOD_RES                   6..7
                          note = Phosphorylation
source                    1..11
                          mol_type = protein
                          organism = synthetic construct
SEQUENCE: 154
GEPNVSYICS R                                                                       11

SEQ ID NO: 155            moltype = AA   length = 11
FEATURE                   Location/Qualifiers
REGION                    1..11
                          note = Description of Artificial Sequence: Synthetic Native
                           peptide sequence
source                    1..11
                          mol_type = protein
                          organism = synthetic construct
SEQUENCE: 155
TPPEAIALCS R                                                                       11

SEQ ID NO: 156            moltype = AA   length = 11
FEATURE                   Location/Qualifiers
REGION                    1..11
                          note = Description of Artificial Sequence: Synthetic Native
                           peptide sequence
MOD_RES                   9
                          note = Carbamidomethylation
source                    1..11
                          mol_type = protein
                          organism = synthetic construct
SEQUENCE: 156
TPPEAIALCS R                                                                       11

SEQ ID NO: 157            moltype = AA   length = 10
FEATURE                   Location/Qualifiers
REGION                    1..10
                          note = Description of Artificial Sequence: Synthetic Native
                           peptide sequence
source                    1..10
                          mol_type = protein
                          organism = synthetic construct
SEQUENCE: 157
DGFYPAPDFR                                                                         10
```

```
SEQ ID NO: 158           moltype = AA  length = 16
FEATURE                  Location/Qualifiers
REGION                   1..16
                         note = Description of Artificial Sequence: Synthetic Native
                           peptide sequence
source                   1..16
                         mol_type = protein
                         organism = synthetic construct
SEQUENCE: 158
DLKPENIMLN HQGHVK                                                             16

SEQ ID NO: 159           moltype = AA  length = 10
FEATURE                  Location/Qualifiers
REGION                   1..10
                         note = Description of Artificial Sequence: Synthetic Native
                           peptide sequence
source                   1..10
                         mol_type = protein
                         organism = synthetic construct
SEQUENCE: 159
FEISETSVNR                                                                    10

SEQ ID NO: 160           moltype = AA  length = 9
FEATURE                  Location/Qualifiers
REGION                   1..9
                         note = Description of Artificial Sequence: Synthetic Native
                           peptide sequence
source                   1..9
                         mol_type = protein
                         organism = synthetic construct
SEQUENCE: 160
FSPGDFWGR                                                                     9

SEQ ID NO: 161           moltype = AA  length = 10
FEATURE                  Location/Qualifiers
REGION                   1..10
                         note = Description of Artificial Sequence: Synthetic Native
                           peptide sequence
source                   1..10
                         mol_type = protein
                         organism = synthetic construct
SEQUENCE: 161
HINWEELLAR                                                                    10

SEQ ID NO: 162           moltype = AA  length = 16
FEATURE                  Location/Qualifiers
REGION                   1..16
                         note = Description of Artificial Sequence: Synthetic Native
                           peptide sequence
source                   1..16
                         mol_type = protein
                         organism = synthetic construct
SEQUENCE: 162
HPFIVDLIYA FQTGGK                                                             16

SEQ ID NO: 163           moltype = AA  length = 10
FEATURE                  Location/Qualifiers
REGION                   1..10
                         note = Description of Artificial Sequence: Synthetic Native
                           peptide sequence
MOD_RES                  5
                         note = Carbamidomethylation
source                   1..10
                         mol_type = protein
                         organism = synthetic construct
SEQUENCE: 163
IRPECFELLR                                                                    10

SEQ ID NO: 164           moltype = AA  length = 10
FEATURE                  Location/Qualifiers
REGION                   1..10
                         note = Description of Artificial Sequence: Synthetic Native
                           peptide sequence
source                   1..10
                         mol_type = protein
                         organism = synthetic construct
SEQUENCE: 164
IRPECFELLR                                                                    10
```

```
SEQ ID NO: 165          moltype = AA  length = 18
FEATURE                 Location/Qualifiers
REGION                  1..18
                        note = Description of Artificial Sequence: Synthetic Native
                         peptide sequence
source                  1..18
                        mol_type = protein
                        organism = synthetic construct
SEQUENCE: 165
LGAGPGDAGE VQAHPFFR                                                        18

SEQ ID NO: 166          moltype = AA  length = 12
FEATURE                 Location/Qualifiers
REGION                  1..12
                        note = Description of Artificial Sequence: Synthetic Native
                         peptide sequence
source                  1..12
                        mol_type = protein
                        organism = synthetic construct
SEQUENCE: 166
LNLPPYLTQE AR                                                              12

SEQ ID NO: 167          moltype = AA  length = 8
FEATURE                 Location/Qualifiers
REGION                  1..8
                        note = Description of Artificial Sequence: Synthetic Native
                         peptide sequence
MOD_RES                 7
                        note = Carbamidomethylation
source                  1..8
                        mol_type = protein
                        organism = synthetic construct
SEQUENCE: 167
LTDFGLCK                                                                    8

SEQ ID NO: 168          moltype = AA  length = 8
FEATURE                 Location/Qualifiers
REGION                  1..8
                        note = Description of Artificial Sequence: Synthetic Native
                         peptide sequence
source                  1..8
                        mol_type = protein
                        organism = synthetic construct
SEQUENCE: 168
LTDFGLCK                                                                    8

SEQ ID NO: 169          moltype = AA  length = 35
FEATURE                 Location/Qualifiers
REGION                  1..35
                        note = Description of Artificial Sequence: Synthetic Native
                         peptide sequence
source                  1..35
                        mol_type = protein
                        organism = synthetic construct
SEQUENCE: 169
QTPVDSPDDS TLSESANQVF LGFTYVAPSV LESVK                                     35

SEQ ID NO: 170          moltype = AA  length = 7
FEATURE                 Location/Qualifiers
REGION                  1..7
                        note = Description of Artificial Sequence: Synthetic Native
                         peptide sequence
source                  1..7
                        mol_type = protein
                        organism = synthetic construct
SEQUENCE: 170
TPVSPVK                                                                     7

SEQ ID NO: 171          moltype = AA  length = 16
FEATURE                 Location/Qualifiers
REGION                  1..16
                        note = Description of Artificial Sequence: Synthetic Native
                         peptide sequence
source                  1..16
                        mol_type = protein
                        organism = synthetic construct
SEQUENCE: 171
TPVSPVKFSP GDFWGR                                                          16
```

```
SEQ ID NO: 172          moltype = AA  length = 35
FEATURE                 Location/Qualifiers
REGION                  1..35
                        note = Description of Artificial Sequence: Synthetic Native
                         peptide sequence
MOD_RES                 24
                        note = Phosphorylation
source                  1..35
                        mol_type = protein
                        organism = synthetic construct
SEQUENCE: 172
QTPVDSPDDS TLSESANQVF LGFTYVAPSV LESVK                                          35

SEQ ID NO: 173          moltype = AA  length = 35
FEATURE                 Location/Qualifiers
REGION                  1..35
                        note = Description of Artificial Sequence: Synthetic Native
                         peptide sequence
MOD_RES                 6
                        note = Phosphorylation
source                  1..35
                        mol_type = protein
                        organism = synthetic construct
SEQUENCE: 173
QTPVDSPDDS TLSESANQVF LGFTYVAPSV LESVK                                          35

SEQ ID NO: 174          moltype = AA  length = 35
FEATURE                 Location/Qualifiers
REGION                  1..35
                        note = Description of Artificial Sequence: Synthetic Native
                         peptide sequence
MOD_RES                 6
                        note = Phosphorylation
MOD_RES                 24
                        note = Phosphorylation
source                  1..35
                        mol_type = protein
                        organism = synthetic construct
SEQUENCE: 174
QTPVDSPDDS TLSESANQVF LGFTYVAPSV LESVK                                          35

SEQ ID NO: 175          moltype = AA  length = 7
FEATURE                 Location/Qualifiers
REGION                  1..7
                        note = Description of Artificial Sequence: Synthetic Native
                         peptide sequence
MOD_RES                 1
                        note = Phosphorylation
source                  1..7
                        mol_type = protein
                        organism = synthetic construct
SEQUENCE: 175
TPVSPVK                                                                          7

SEQ ID NO: 176          moltype = AA  length = 7
FEATURE                 Location/Qualifiers
REGION                  1..7
                        note = Description of Artificial Sequence: Synthetic Native
                         peptide sequence
MOD_RES                 4
                        note = Phosphorylation
source                  1..7
                        mol_type = protein
                        organism = synthetic construct
SEQUENCE: 176
TPVSPVK                                                                          7

SEQ ID NO: 177          moltype = AA  length = 7
FEATURE                 Location/Qualifiers
REGION                  1..7
                        note = Description of Artificial Sequence: Synthetic Native
                         peptide sequence
MOD_RES                 1
                        note = Phosphorylation
MOD_RES                 4
                        note = Phosphorylation
source                  1..7
                        mol_type = protein
                        organism = synthetic construct
```

```
SEQUENCE: 177
TPVSPVK                                                                         7

SEQ ID NO: 178         moltype = AA  length = 16
FEATURE                Location/Qualifiers
REGION                 1..16
                       note = Description of Artificial Sequence: Synthetic Native
                        peptide sequence
MOD_RES                4
                       note = Phosphorylation
source                 1..16
                       mol_type = protein
                       organism = synthetic construct
SEQUENCE: 178
TPVSPVKFSP GDFWGR                                                              16

SEQ ID NO: 179         moltype = AA  length = 16
FEATURE                Location/Qualifiers
REGION                 1..16
                       note = Description of Artificial Sequence: Synthetic Native
                        peptide sequence
MOD_RES                1
                       note = Phosphorylation
MOD_RES                4
                       note = Phosphorylation
source                 1..16
                       mol_type = protein
                       organism = synthetic construct
SEQUENCE: 179
TPVSPVKFSP GDFWGR                                                              16

SEQ ID NO: 180         moltype = AA  length = 16
FEATURE                Location/Qualifiers
REGION                 1..16
                       note = Description of Artificial Sequence: Synthetic Native
                        peptide sequence
MOD_RES                1
                       note = Phosphorylation
source                 1..16
                       mol_type = protein
                       organism = synthetic construct
SEQUENCE: 180
TPVSPVKFSP GDFWGR                                                              16

SEQ ID NO: 181         moltype = AA  length = 12
FEATURE                Location/Qualifiers
REGION                 1..12
                       note = Description of Artificial Sequence: Synthetic Native
                        peptide sequence
source                 1..12
                       mol_type = protein
                       organism = synthetic construct
SEQUENCE: 181
DIPGLTDTTV PR                                                                  12

SEQ ID NO: 182         moltype = AA  length = 8
FEATURE                Location/Qualifiers
REGION                 1..8
                       note = Description of Artificial Sequence: Synthetic Native
                        peptide sequence
MOD_RES                4
                       note = Carbamidomethylation
source                 1..8
                       mol_type = protein
                       organism = synthetic construct
SEQUENCE: 182
GHSCYRPR                                                                        8

SEQ ID NO: 183         moltype = AA  length = 8
FEATURE                Location/Qualifiers
REGION                 1..8
                       note = Description of Artificial Sequence: Synthetic Native
                        peptide sequence
source                 1..8
                       mol_type = protein
                       organism = synthetic construct
SEQUENCE: 183
GHSCYRPR                                                                        8
```

| | | |
|---|---|---|
| SEQ ID NO: 184<br>FEATURE<br>REGION | moltype = AA   length = 12<br>Location/Qualifiers<br>1..12<br>note = Description of Artificial Sequence: Synthetic Native<br> peptide sequence | |
| MOD_RES | 10<br>note = Carbamidomethylation | |
| source | 1..12<br>mol_type = protein<br>organism = synthetic construct | |
| SEQUENCE: 184<br>LNISFPATGC QK | | 12 |
| SEQ ID NO: 185<br>FEATURE<br>REGION | moltype = AA   length = 12<br>Location/Qualifiers<br>1..12<br>note = Description of Artificial Sequence: Synthetic Native<br> peptide sequence | |
| source | 1..12<br>mol_type = protein<br>organism = synthetic construct | |
| SEQUENCE: 185<br>LNISFPATGC QK | | 12 |
| SEQ ID NO: 186<br>FEATURE<br>REGION | moltype = AA   length = 15<br>Location/Qualifiers<br>1..15<br>note = Description of Artificial Sequence: Synthetic Native<br> peptide sequence | |
| source | 1..15<br>mol_type = protein<br>organism = synthetic construct | |
| SEQUENCE: 186<br>MATEVAADAL GEEWK | | 15 |
| SEQ ID NO: 187<br>FEATURE<br>REGION | moltype = AA   length = 13<br>Location/Qualifiers<br>1..13<br>note = Description of Artificial Sequence: Synthetic Native<br> peptide sequence | |
| source | 1..13<br>mol_type = protein<br>organism = synthetic construct | |
| SEQUENCE: 187<br>RRRLSSLRAS TSK | | 13 |
| SEQ ID NO: 188<br>FEATURE<br>REGION | moltype = AA   length = 13<br>Location/Qualifiers<br>1..13<br>note = Description of Artificial Sequence: Synthetic Native<br> peptide sequence | |
| MOD_RES | 5<br>note = Phosphorylation | |
| source | 1..13<br>mol_type = protein<br>organism = synthetic construct | |
| SEQUENCE: 188<br>RRRLSSLRAS TSK | | 13 |
| SEQ ID NO: 189<br>FEATURE<br>REGION | moltype = AA   length = 13<br>Location/Qualifiers<br>1..13<br>note = Description of Artificial Sequence: Synthetic Native<br> peptide sequence | |
| MOD_RES | 6<br>note = Phosphorylation | |
| source | 1..13<br>mol_type = protein<br>organism = synthetic construct | |
| SEQUENCE: 189<br>RRRLSSLRAS TSK | | 13 |
| SEQ ID NO: 190<br>FEATURE<br>REGION | moltype = AA   length = 13<br>Location/Qualifiers<br>1..13<br>note = Description of Artificial Sequence: Synthetic Native<br> peptide sequence | |
| MOD_RES | 5..6<br>note = Phosphorylation | |

| | | |
|---|---|---|
| source | 1..13<br>mol_type = protein<br>organism = synthetic construct | |
| SEQUENCE: 190<br>RRRLSSLRAS TSK | | 13 |
| SEQ ID NO: 191<br>FEATURE<br>REGION | moltype = AA  length = 30<br>Location/Qualifiers<br>1..30<br>note = Description of Artificial Sequence: Synthetic Native<br> peptide sequence | |
| source | 1..30<br>mol_type = protein<br>organism = synthetic construct | |
| SEQUENCE: 191<br>AATAARPPAP PPAPQPPSPT PSPPRPTLAR | | 30 |
| SEQ ID NO: 192<br>FEATURE<br>REGION | moltype = AA  length = 10<br>Location/Qualifiers<br>1..10<br>note = Description of Artificial Sequence: Synthetic Native<br> peptide sequence | |
| MOD_RES | 1<br>note = Carbamidomethylation | |
| source | 1..10<br>mol_type = protein<br>organism = synthetic construct | |
| SEQUENCE: 192<br>CLHDIALAHR | | 10 |
| SEQ ID NO: 193<br>FEATURE<br>REGION | moltype = AA  length = 10<br>Location/Qualifiers<br>1..10<br>note = Description of Artificial Sequence: Synthetic Native<br> peptide sequence | |
| source | 1..10<br>mol_type = protein<br>organism = synthetic construct | |
| SEQUENCE: 193<br>CLHDIALAHR | | 10 |
| SEQ ID NO: 194<br>FEATURE<br>REGION | moltype = AA  length = 15<br>Location/Qualifiers<br>1..15<br>note = Description of Artificial Sequence: Synthetic Native<br> peptide sequence | |
| source | 1..15<br>mol_type = protein<br>organism = synthetic construct | |
| SEQUENCE: 194<br>EAEDTQVFGD LPRPR | | 15 |
| SEQ ID NO: 195<br>FEATURE<br>REGION | moltype = AA  length = 12<br>Location/Qualifiers<br>1..12<br>note = Description of Artificial Sequence: Synthetic Native<br> peptide sequence | |
| source | 1..12<br>mol_type = protein<br>organism = synthetic construct | |
| SEQUENCE: 195<br>SLPVSVPVWG FK | | 12 |
| SEQ ID NO: 196<br>FEATURE<br>REGION | moltype = AA  length = 16<br>Location/Qualifiers<br>1..16<br>note = Description of Artificial Sequence: Synthetic Native<br> peptide sequence | |
| source | 1..16<br>mol_type = protein<br>organism = synthetic construct | |
| SEQUENCE: 196<br>SSDEENGPPS SPDLDR | | 16 |
| SEQ ID NO: 197<br>FEATURE<br>REGION | moltype = AA  length = 20<br>Location/Qualifiers<br>1..20<br>note = Description of Artificial Sequence: Synthetic Native<br> peptide sequence | |

```
source                  1..20
                        mol_type = protein
                        organism = synthetic construct
SEQUENCE: 197
TEARSSDEEN GPPSSPDLDR                                                      20

SEQ ID NO: 198          moltype = AA  length = 28
FEATURE                 Location/Qualifiers
REGION                  1..28
                        note = Description of Artificial Sequence: Synthetic Native
                         peptide sequence
MOD_RES                 21
                        note = Carbamidomethylation
source                  1..28
                        mol_type = protein
                        organism = synthetic construct
SEQUENCE: 198
TGTELVLLTA APPPPPRPGP CAYAAHGR                                             28

SEQ ID NO: 199          moltype = AA  length = 28
FEATURE                 Location/Qualifiers
REGION                  1..28
                        note = Description of Artificial Sequence: Synthetic Native
                         peptide sequence
source                  1..28
                        mol_type = protein
                        organism = synthetic construct
SEQUENCE: 199
TGTELVLLTA APPPPPRPGP CAYAAHGR                                             28

SEQ ID NO: 200          moltype = AA  length = 8
FEATURE                 Location/Qualifiers
REGION                  1..8
                        note = Description of Artificial Sequence: Synthetic Native
                         peptide sequence
source                  1..8
                        mol_type = protein
                        organism = synthetic construct
SEQUENCE: 200
LNTSDFQK                                                                    8

SEQ ID NO: 201          moltype = AA  length = 23
FEATURE                 Location/Qualifiers
REGION                  1..23
                        note = Description of Artificial Sequence: Synthetic Native
                         peptide sequence
source                  1..23
                        mol_type = protein
                        organism = synthetic construct
SEQUENCE: 201
EAEDTQVFGD LPRPRLNTSD FQK                                                  23

SEQ ID NO: 202          moltype = AA  length = 8
FEATURE                 Location/Qualifiers
REGION                  1..8
                        note = Description of Artificial Sequence: Synthetic Native
                         peptide sequence
source                  1..8
                        mol_type = protein
                        organism = synthetic construct
SEQUENCE: 202
GALAEAAR                                                                    8

SEQ ID NO: 203          moltype = AA  length = 18
FEATURE                 Location/Qualifiers
REGION                  1..18
                        note = Description of Artificial Sequence: Synthetic Native
                         peptide sequence
source                  1..18
                        mol_type = protein
                        organism = synthetic construct
SEQUENCE: 203
ASGRPEELWE AVVGAAER                                                        18

SEQ ID NO: 204          moltype = AA  length = 8
FEATURE                 Location/Qualifiers
REGION                  1..8
                        note = Description of Artificial Sequence: Synthetic Native
                         peptide sequence
```

```
MOD_RES              3
                     note = Phosphorylation
source               1..8
                     mol_type = protein
                     organism = synthetic construct
SEQUENCE: 204
LNTSDFQK                                                                    8

SEQ ID NO: 205       moltype = AA   length = 23
FEATURE              Location/Qualifiers
REGION               1..23
                     note = Description of Artificial Sequence: Synthetic Native
                      peptide sequence
MOD_RES              18
                     note = Phosphorylation
source               1..23
                     mol_type = protein
                     organism = synthetic construct
SEQUENCE: 205
EAEDTQVFGD LPRPRLNTSD FQK                                                  23

SEQ ID NO: 206       moltype = AA   length = 24
FEATURE              Location/Qualifiers
REGION               1..24
                     note = Description of Artificial Sequence: Synthetic Native
                      peptide sequence
source               1..24
                     mol_type = protein
                     organism = synthetic construct
SEQUENCE: 206
YSDTTDSDPE NEPFDEDQHT QITK                                                 24

SEQ ID NO: 207       moltype = AA   length = 25
FEATURE              Location/Qualifiers
REGION               1..25
                     note = Description of Artificial Sequence: Synthetic Native
                      peptide sequence
source               1..25
                     mol_type = protein
                     organism = synthetic construct
SEQUENCE: 207
YSDTTDSDPE NEPFDEDQHT QITKV                                                25

SEQ ID NO: 208       moltype = AA   length = 8
FEATURE              Location/Qualifiers
REGION               1..8
                     note = Description of Artificial Sequence: Synthetic Native
                      peptide sequence
source               1..8
                     mol_type = protein
                     organism = synthetic construct
SEQUENCE: 208
NNIDDVVR                                                                    8

SEQ ID NO: 209       moltype = AA   length = 12
FEATURE              Location/Qualifiers
REGION               1..12
                     note = Description of Artificial Sequence: Synthetic Native
                      peptide sequence
source               1..12
                     mol_type = protein
                     organism = synthetic construct
SEQUENCE: 209
AQEALDFYGE VR                                                              12

SEQ ID NO: 210       moltype = AA   length = 10
FEATURE              Location/Qualifiers
REGION               1..10
                     note = Description of Artificial Sequence: Synthetic Native
                      peptide sequence
source               1..10
                     mol_type = protein
                     organism = synthetic construct
SEQUENCE: 210
IYSSNSGPTR                                                                 10

SEQ ID NO: 211       moltype = AA   length = 24
FEATURE              Location/Qualifiers
REGION               1..24
```

```
                        note = Description of Artificial Sequence: Synthetic Native
                         peptide sequence
MOD_RES                 2
                        note = Phosphorylation
source                  1..24
                        mol_type = protein
                        organism = synthetic construct
SEQUENCE: 211
YSDTTDSDPE NEPFDEDQHT QITK                                                        24

SEQ ID NO: 212          moltype = AA  length = 25
FEATURE                 Location/Qualifiers
REGION                  1..25
                        note = Description of Artificial Sequence: Synthetic Native
                         peptide sequence
MOD_RES                 2
                        note = Phosphorylation
source                  1..25
                        mol_type = protein
                        organism = synthetic construct
SEQUENCE: 212
YSDTTDSDPE NEPFDEDQHT QITKV                                                       25

SEQ ID NO: 213          moltype = AA  length = 9
FEATURE                 Location/Qualifiers
REGION                  1..9
                        note = Description of Artificial Sequence: Synthetic
                         Internal standard peptide sequence
MOD_RES                 9
                        note = K(13C6; 15N2)
source                  1..9
                        mol_type = protein
                        organism = synthetic construct
SEQUENCE: 213
NDGTFIGYK                                                                          9

SEQ ID NO: 214          moltype = AA  length = 8
FEATURE                 Location/Qualifiers
REGION                  1..8
                        note = Description of Artificial Sequence: Synthetic
                         Internal standard peptide sequence
MOD_RES                 8
                        note = K(13C6; 15N2)
source                  1..8
                        mol_type = protein
                        organism = synthetic construct
SEQUENCE: 214
SLLSGLLK                                                                           8

SEQ ID NO: 215          moltype = AA  length = 16
FEATURE                 Location/Qualifiers
REGION                  1..16
                        note = Description of Artificial Sequence: Synthetic
                         Internal standard peptide sequence
MOD_RES                 16
                        note = K(13C6; 15N2)
source                  1..16
                        mol_type = protein
                        organism = synthetic construct
SEQUENCE: 215
EAPLNNFSVA QCQLMK                                                                 16

SEQ ID NO: 216          moltype = AA  length = 15
FEATURE                 Location/Qualifiers
REGION                  1..15
                        note = Description of Artificial Sequence: Synthetic
                         Internal standard peptide sequence
MOD_RES                 8
                        note = Phosphorylation
MOD_RES                 15
                        note = A(13C3; 15N)
source                  1..15
                        mol_type = protein
                        organism = synthetic construct
SEQUENCE: 216
RPHFPQFSYS ASGTA                                                                  15

SEQ ID NO: 217          moltype = AA  length = 16
FEATURE                 Location/Qualifiers
```

```
REGION                      1..16
                            note = Description of Artificial Sequence: Synthetic
                             Internal standard peptide sequence
MOD_RES                     16
                            note = A(13C3; 15N)
source                      1..16
                            mol_type = protein
                            organism = synthetic construct
SEQUENCE: 217
RPHFPQFSYS ASGTAA                                                           16

SEQ ID NO: 218              moltype = AA  length = 9
FEATURE                     Location/Qualifiers
REGION                      1..9
                            note = Description of Artificial Sequence: Synthetic
                             Internal standard peptide sequence
MOD_RES                     9
                            note = K(13C6; 15N2)
source                      1..9
                            mol_type = protein
                            organism = synthetic construct
SEQUENCE: 218
SDGSFIGYK                                                                    9

SEQ ID NO: 219              moltype = AA  length = 8
FEATURE                     Location/Qualifiers
REGION                      1..8
                            note = Description of Artificial Sequence: Synthetic
                             Internal standard peptide sequence
MOD_RES                     8
                            note = K(13C6; 15N2)
source                      1..8
                            mol_type = protein
                            organism = synthetic construct
SEQUENCE: 219
SLLAGLLK                                                                     8

SEQ ID NO: 220              moltype = AA  length = 14
FEATURE                     Location/Qualifiers
REGION                      1..14
                            note = Description of Artificial Sequence: Synthetic
                             Internal standard peptide sequence
MOD_RES                     7
                            note = Phosphorylation
MOD_RES                     13
                            note = R(13C6; 15N4)
source                      1..14
                            mol_type = protein
                            organism = synthetic construct
SEQUENCE: 220
THFPQFSYSA SIRE                                                             14

SEQ ID NO: 221              moltype = AA  length = 14
FEATURE                     Location/Qualifiers
REGION                      1..14
                            note = Description of Artificial Sequence: Synthetic
                             Internal standard peptide sequence
MOD_RES                     13
                            note = R(13C6; 15N4)
source                      1..14
                            mol_type = protein
                            organism = synthetic construct
SEQUENCE: 221
THFPQFSYSA SIRE                                                             14

SEQ ID NO: 222              moltype = AA  length = 16
FEATURE                     Location/Qualifiers
REGION                      1..16
                            note = Description of Artificial Sequence: Synthetic
                             Internal standard peptide sequence
MOD_RES                     16
                            note = R(13C6; 15N4)
source                      1..16
                            mol_type = protein
                            organism = synthetic construct
SEQUENCE: 222
LVPPFKPQVT SETDTR                                                           16

SEQ ID NO: 223              moltype = AA  length = 9
```

| | | |
|---|---|---|
| FEATURE | Location/Qualifiers | |
| REGION | 1..9<br>note = Description of Artificial Sequence: Synthetic<br>Internal standard peptide sequence | |
| MOD_RES | 9<br>note = K(13C6; 15N2) | |
| source | 1..9<br>mol_type = protein<br>organism = synthetic construct | |
| SEQUENCE: 223<br>SLLSGLLIK | | 9 |
| SEQ ID NO: 224<br>FEATURE<br>REGION | moltype = AA  length = 10<br>Location/Qualifiers<br>1..10<br>note = Description of Artificial Sequence: Synthetic<br>Internal standard peptide sequence | |
| MOD_RES | 1<br>note = Carbamidomethylation | |
| MOD_RES | 10<br>note = R(13C6; 15N4) | |
| source | 1..10<br>mol_type = protein<br>organism = synthetic construct | |
| SEQUENCE: 224<br>CSVAAYVSAR | | 10 |
| SEQ ID NO: 225<br>FEATURE<br>REGION | moltype = AA  length = 10<br>Location/Qualifiers<br>1..10<br>note = Description of Artificial Sequence: Synthetic<br>Internal standard peptide sequence | |
| MOD_RES | 10<br>note = R(13C6; 15N4) | |
| source | 1..10<br>mol_type = protein<br>organism = synthetic construct | |
| SEQUENCE: 225<br>CSVAAYVSAR | | 10 |
| SEQ ID NO: 226<br>FEATURE<br>REGION | moltype = AA  length = 13<br>Location/Qualifiers<br>1..13<br>note = Description of Artificial Sequence: Synthetic<br>Internal standard peptide sequence | |
| MOD_RES | 13<br>note = K(13C6; 15N2) | |
| source | 1..13<br>mol_type = protein<br>organism = synthetic construct | |
| SEQUENCE: 226<br>GLKPWTQYAI FVK | | 13 |
| SEQ ID NO: 227<br>FEATURE<br>REGION | moltype = AA  length = 14<br>Location/Qualifiers<br>1..14<br>note = Description of Artificial Sequence: Synthetic<br>Internal standard peptide sequence | |
| MOD_RES | 6<br>note = Carbamidomethylation | |
| MOD_RES | 14<br>note = R(13C6; 15N4) | |
| source | 1..14<br>mol_type = protein<br>organism = synthetic construct | |
| SEQUENCE: 227<br>IELQACNQDT PEER | | 14 |
| SEQ ID NO: 228<br>FEATURE<br>REGION | moltype = AA  length = 12<br>Location/Qualifiers<br>1..12<br>note = Description of Artificial Sequence: Synthetic<br>Internal standard peptide sequence | |
| MOD_RES | 12<br>note = R(13C6; 15N4) | |
| source | 1..12<br>mol_type = protein<br>organism = synthetic construct | |
| SEQUENCE: 228 | | |

TIDSVTSAQE LR                                                                    12

SEQ ID NO: 229           moltype = AA   length = 15
FEATURE                  Location/Qualifiers
REGION                   1..15
                         note = Description of Artificial Sequence: Synthetic
                          Internal standard peptide sequence
MOD_RES                  15
                         note = R(13C6; 15N4)
source                   1..15
                         mol_type = protein
                         organism = synthetic construct
SEQUENCE: 229
TNCPATVING QFVER                                                                 15

SEQ ID NO: 230           moltype = AA   length = 15
FEATURE                  Location/Qualifiers
REGION                   1..15
                         note = Description of Artificial Sequence: Synthetic
                          Internal standard peptide sequence
MOD_RES                  3
                         note = Carbamidomethylation
MOD_RES                  15
                         note = R(13C6; 15N4)
source                   1..15
                         mol_type = protein
                         organism = synthetic construct
SEQUENCE: 230
TNCPATVING QFVER                                                                 15

SEQ ID NO: 231           moltype = AA   length = 14
FEATURE                  Location/Qualifiers
REGION                   1..14
                         note = Description of Artificial Sequence: Synthetic
                          Internal standard peptide sequence
MOD_RES                  14
                         note = K(13C6; 15N2)
source                   1..14
                         mol_type = protein
                         organism = synthetic construct
SEQUENCE: 231
TNGDQASCEN ELLK                                                                  14

SEQ ID NO: 232           moltype = AA   length = 14
FEATURE                  Location/Qualifiers
REGION                   1..14
                         note = Description of Artificial Sequence: Synthetic
                          Internal standard peptide sequence
MOD_RES                  8
                         note = Carbamidomethylation
MOD_RES                  14
                         note = K(13C6; 15N2)
source                   1..14
                         mol_type = protein
                         organism = synthetic construct
SEQUENCE: 232
TNGDQASCEN ELLK                                                                  14

SEQ ID NO: 233           moltype = AA   length = 9
FEATURE                  Location/Qualifiers
REGION                   1..9
                         note = Description of Artificial Sequence: Synthetic
                          Internal standard peptide sequence
MOD_RES                  9
                         note = K(13C6; 15N2)
source                   1..9
                         mol_type = protein
                         organism = synthetic construct
SEQUENCE: 233
VCHLLEGEK                                                                         9

SEQ ID NO: 234           moltype = AA   length = 9
FEATURE                  Location/Qualifiers
REGION                   1..9
                         note = Description of Artificial Sequence: Synthetic
                          Internal standard peptide sequence
MOD_RES                  2
                         note = Carbamidomethylation
MOD_RES                  9

```
                        note = K(13C6; 15N2)
source                  1..9
                        mol_type = protein
                        organism = synthetic construct
SEQUENCE: 234
VCHLLEGEK                                                                        9

SEQ ID NO: 235          moltype = AA   length = 9
FEATURE                 Location/Qualifiers
REGION                  1..9
                        note = Description of Artificial Sequence: Synthetic
                         Internal standard peptide sequence
MOD_RES                 9
                        note = R(13C6; 15N4)
source                  1..9
                        mol_type = protein
                        organism = synthetic construct
SEQUENCE: 235
TVNESASLR                                                                        9

SEQ ID NO: 236          moltype = AA   length = 10
FEATURE                 Location/Qualifiers
REGION                  1..10
                        note = Description of Artificial Sequence: Synthetic
                         Internal standard peptide sequence
MOD_RES                 10
                        note = R(13C6; 15N4)
source                  1..10
                        mol_type = protein
                        organism = synthetic construct
SEQUENCE: 236
DIIKGEAETR                                                                      10

SEQ ID NO: 237          moltype = AA   length = 9
FEATURE                 Location/Qualifiers
REGION                  1..9
                        note = Description of Artificial Sequence: Synthetic
                         Internal standard peptide sequence
MOD_RES                 9
                        note = R(13C6; 15N4)
source                  1..9
                        mol_type = protein
                        organism = synthetic construct
SEQUENCE: 237
DIYETDYYR                                                                        9

SEQ ID NO: 238          moltype = AA   length = 10
FEATURE                 Location/Qualifiers
REGION                  1..10
                        note = Description of Artificial Sequence: Synthetic
                         Internal standard peptide sequence
MOD_RES                 10
                        note = K(13C6; 15N2)
source                  1..10
                        mol_type = protein
                        organism = synthetic construct
SEQUENCE: 238
DIYETDYYRK                                                                      10

SEQ ID NO: 239          moltype = AA   length = 9
FEATURE                 Location/Qualifiers
REGION                  1..9
                        note = Description of Artificial Sequence: Synthetic
                         Internal standard peptide sequence
MOD_RES                 3
                        note = Phosphorylation
MOD_RES                 9
                        note = R(13C6; 15N4)
source                  1..9
                        mol_type = protein
                        organism = synthetic construct
SEQUENCE: 239
DIYETDYYR                                                                        9

SEQ ID NO: 240          moltype = AA   length = 9
FEATURE                 Location/Qualifiers
REGION                  1..9
                        note = Description of Artificial Sequence: Synthetic
                         Internal standard peptide sequence
```

```
MOD_RES              7
                     note = Phosphorylation
MOD_RES              9
                     note = R(13C6; 15N4)
source               1..9
                     mol_type = protein
                     organism = synthetic construct
SEQUENCE: 240
DIYETDYYR                                                                        9

SEQ ID NO: 241       moltype = AA  length = 9
FEATURE              Location/Qualifiers
REGION               1..9
                     note = Description of Artificial Sequence: Synthetic
                      Internal standard peptide sequence
MOD_RES              8
                     note = Phosphorylation
MOD_RES              9
                     note = R(13C6; 15N4)
source               1..9
                     mol_type = protein
                     organism = synthetic construct
SEQUENCE: 241
DIYETDYYR                                                                        9

SEQ ID NO: 242       moltype = AA  length = 9
FEATURE              Location/Qualifiers
REGION               1..9
                     note = Description of Artificial Sequence: Synthetic
                      Internal standard peptide sequence
MOD_RES              7..8
                     note = Phosphorylation
MOD_RES              9
                     note = R(13C6; 15N4)
source               1..9
                     mol_type = protein
                     organism = synthetic construct
SEQUENCE: 242
DIYETDYYR                                                                        9

SEQ ID NO: 243       moltype = AA  length = 9
FEATURE              Location/Qualifiers
REGION               1..9
                     note = Description of Artificial Sequence: Synthetic
                      Internal standard peptide sequence
MOD_RES              3
                     note = Phosphorylation
MOD_RES              7
                     note = Phosphorylation
MOD_RES              9
                     note = R(13C6; 15N4)
source               1..9
                     mol_type = protein
                     organism = synthetic construct
SEQUENCE: 243
DIYETDYYR                                                                        9

SEQ ID NO: 244       moltype = AA  length = 9
FEATURE              Location/Qualifiers
REGION               1..9
                     note = Description of Artificial Sequence: Synthetic
                      Internal standard peptide sequence
MOD_RES              3
                     note = Phosphorylation
MOD_RES              8
                     note = Phosphorylation
MOD_RES              9
                     note = R(13C6; 15N4)
source               1..9
                     mol_type = protein
                     organism = synthetic construct
SEQUENCE: 244
DIYETDYYR                                                                        9

SEQ ID NO: 245       moltype = AA  length = 9
FEATURE              Location/Qualifiers
REGION               1..9
                     note = Description of Artificial Sequence: Synthetic
                      Internal standard peptide sequence
```

```
MOD_RES            3
                   note = Phosphorylation
MOD_RES            7..8
                   note = Phosphorylation
MOD_RES            9
                   note = R(13C6; 15N4)
source             1..9
                   mol_type = protein
                   organism = synthetic construct
SEQUENCE: 245
DIYETDYYR                                                                     9

SEQ ID NO: 246     moltype = AA  length = 13
FEATURE            Location/Qualifiers
REGION             1..13
                   note = Description of Artificial Sequence: Synthetic
                   Internal standard peptide sequence
MOD_RES            13
                   note = R(13C6; 15N4)
source             1..13
                   mol_type = protein
                   organism = synthetic construct
SEQUENCE: 246
AENGPGPGVL VLR                                                                13

SEQ ID NO: 247     moltype = AA  length = 18
FEATURE            Location/Qualifiers
REGION             1..18
                   note = Description of Artificial Sequence: Synthetic
                   Internal standard peptide sequence
MOD_RES            8
                   note = Carbamidomethylation
MOD_RES            12
                   note = Carbamidomethylation
MOD_RES            18
                   note = R(13C6; 15N4)
source             1..18
                   mol_type = protein
                   organism = synthetic construct
SEQUENCE: 247
HYYYAGVCVP ACPPNTYR                                                           18

SEQ ID NO: 248     moltype = AA  length = 18
FEATURE            Location/Qualifiers
REGION             1..18
                   note = Description of Artificial Sequence: Synthetic
                   Internal standard peptide sequence
MOD_RES            18
                   note = R(13C6; 15N4)
source             1..18
                   mol_type = protein
                   organism = synthetic construct
SEQUENCE: 248
HYYYAGVCVP ACPPNTYR                                                           18

SEQ ID NO: 249     moltype = AA  length = 12
FEATURE            Location/Qualifiers
REGION             1..12
                   note = Description of Artificial Sequence: Synthetic
                   Internal standard peptide sequence
MOD_RES            3
                   note = Carbamidomethylation
MOD_RES            12
                   note = R(13C6; 15N4)
source             1..12
                   mol_type = protein
                   organism = synthetic construct
SEQUENCE: 249
LGCSASNFVF AR                                                                 12

SEQ ID NO: 250     moltype = AA  length = 12
FEATURE            Location/Qualifiers
REGION             1..12
                   note = Description of Artificial Sequence: Synthetic
                   Internal standard peptide sequence
MOD_RES            12
                   note = R(13C6; 15N4)
source             1..12
                   mol_type = protein
```

-continued

```
                          organism = synthetic construct
SEQUENCE: 250
LGCSASNFVF AR                                                          12

SEQ ID NO: 251            moltype = AA   length = 19
FEATURE                   Location/Qualifiers
REGION                    1..19
                          note = Description of Artificial Sequence: Synthetic
                           Internal standard peptide sequence
MOD_RES                   19
                          note = K(13C6; 15N2)
source                    1..19
                          mol_type = protein
                          organism = synthetic construct
SEQUENCE: 251
SLRPEMENNP VLAPPSLSK                                                   19

SEQ ID NO: 252            moltype = AA   length = 10
FEATURE                   Location/Qualifiers
REGION                    1..10
                          note = Description of Artificial Sequence: Synthetic
                           Internal standard peptide sequence
MOD_RES                   10
                          note = R(13C6; 15N4)
source                    1..10
                          mol_type = protein
                          organism = synthetic construct
SEQUENCE: 252
TTINNEYNYR                                                             10

SEQ ID NO: 253            moltype = AA   length = 18
FEATURE                   Location/Qualifiers
REGION                    1..18
                          note = Description of Artificial Sequence: Synthetic
                           Internal standard peptide sequence
MOD_RES                   18
                          note = R(13C6; 15N4)
source                    1..18
                          mol_type = protein
                          organism = synthetic construct
SEQUENCE: 253
VAGLESLGDL FPNLTVIR                                                    18

SEQ ID NO: 254            moltype = AA   length = 16
FEATURE                   Location/Qualifiers
REGION                    1..16
                          note = Description of Artificial Sequence: Synthetic
                           Internal standard peptide sequence
MOD_RES                   16
                          note = K(13C6; 15N2)
source                    1..16
                          mol_type = protein
                          organism = synthetic construct
SEQUENCE: 254
YADGTIDIEE VTENPK                                                      16

SEQ ID NO: 255            moltype = AA   length = 14
FEATURE                   Location/Qualifiers
REGION                    1..14
                          note = Description of Artificial Sequence: Synthetic
                           Internal standard peptide sequence
MOD_RES                   11
                          note = Carbamidomethylation
MOD_RES                   14
                          note = R(13C6; 15N4)
source                    1..14
                          mol_type = protein
                          organism = synthetic construct
SEQUENCE: 255
YGSQVEDQRE CVSR                                                        14

SEQ ID NO: 256            moltype = AA   length = 14
FEATURE                   Location/Qualifiers
REGION                    1..14
                          note = Description of Artificial Sequence: Synthetic
                           Internal standard peptide sequence
MOD_RES                   14
                          note = R(13C6; 15N4)
source                    1..14
```

```
                            mol_type = protein
                            organism = synthetic construct
SEQUENCE: 256
YGSQVEDQRE CVSR                                                        14

SEQ ID NO: 257              moltype = AA   length = 12
FEATURE                     Location/Qualifiers
REGION                      1..12
                            note = Description of Artificial Sequence: Synthetic
                              Internal standard peptide sequence
MOD_RES                     12
                            note = K(13C6; 15N2)
source                      1..12
                            mol_type = protein
                            organism = synthetic construct
SEQUENCE: 257
IDIHSCNHEA EK                                                          12

SEQ ID NO: 258              moltype = AA   length = 10
FEATURE                     Location/Qualifiers
REGION                      1..10
                            note = Description of Artificial Sequence: Synthetic
                              Internal standard peptide sequence
MOD_RES                     10
                            note = R(13C6; 15N4)
source                      1..10
                            mol_type = protein
                            organism = synthetic construct
SEQUENCE: 258
GVVKDEPETR                                                             10

SEQ ID NO: 259              moltype = AA   length = 26
FEATURE                     Location/Qualifiers
REGION                      1..26
                            note = Description of Artificial Sequence: Synthetic
                              Internal standard peptide sequence
MOD_RES                     26
                            note = R(13C6; 15N4)
source                      1..26
                            mol_type = protein
                            organism = synthetic construct
SEQUENCE: 259
ASSDGEGTMS RPASVDGSPV SPSTNR                                           26

SEQ ID NO: 260              moltype = AA   length = 14
FEATURE                     Location/Qualifiers
REGION                      1..14
                            note = Description of Artificial Sequence: Synthetic
                              Internal standard peptide sequence
MOD_RES                     1
                            note = Carbamidomethylation
MOD_RES                     14
                            note = R(13C6; 15N4)
source                      1..14
                            mol_type = protein
                            organism = synthetic construct
SEQUENCE: 260
CGHSENFFFI EVGR                                                        14

SEQ ID NO: 261              moltype = AA   length = 14
FEATURE                     Location/Qualifiers
REGION                      1..14
                            note = Description of Artificial Sequence: Synthetic
                              Internal standard peptide sequence
MOD_RES                     14
                            note = R(13C6; 15N4)
source                      1..14
                            mol_type = protein
                            organism = synthetic construct
SEQUENCE: 261
CGHSENFFFI EVGR                                                        14

SEQ ID NO: 262              moltype = AA   length = 27
FEATURE                     Location/Qualifiers
REGION                      1..27
                            note = Description of Artificial Sequence: Synthetic
                              Internal standard peptide sequence
MOD_RES                     1
                            note = Carbamidomethylation
```

```
MOD_RES              27
                     note = R(13C6; 15N4)
source               1..27
                     mol_type = protein
                     organism = synthetic construct
SEQUENCE: 262
CTPGTGLGTS PALAGDEAAS AADLDNR                                              27

SEQ ID NO: 263       moltype = AA  length = 27
FEATURE              Location/Qualifiers
REGION               1..27
                     note = Description of Artificial Sequence: Synthetic
                      Internal standard peptide sequence
MOD_RES              27
                     note = R(13C6; 15N4)
source               1..27
                     mol_type = protein
                     organism = synthetic construct
SEQUENCE: 263
CTPGTGLGTS PALAGDEAAS AADLDNR                                              27

SEQ ID NO: 264       moltype = AA  length = 15
FEATURE              Location/Qualifiers
REGION               1..15
                     note = Description of Artificial Sequence: Synthetic
                      Internal standard peptide sequence
MOD_RES              15
                     note = R(13C6; 15N4)
source               1..15
                     mol_type = protein
                     organism = synthetic construct
SEQUENCE: 264
HHLNNPPPSQ VGLTR                                                           15

SEQ ID NO: 265       moltype = AA  length = 14
FEATURE              Location/Qualifiers
REGION               1..14
                     note = Description of Artificial Sequence: Synthetic
                      Internal standard peptide sequence
MOD_RES              14
                     note = R(13C6; 15N4)
source               1..14
                     mol_type = protein
                     organism = synthetic construct
SEQUENCE: 265
HSSETFSSTP SATR                                                            14

SEQ ID NO: 266       moltype = AA  length = 12
FEATURE              Location/Qualifiers
REGION               1..12
                     note = Description of Artificial Sequence: Synthetic
                      Internal standard peptide sequence
MOD_RES              12
                     note = K(13C6; 15N2)
source               1..12
                     mol_type = protein
                     organism = synthetic construct
SEQUENCE: 266
KGSGDYMPMS PK                                                              12

SEQ ID NO: 267       moltype = AA  length = 21
FEATURE              Location/Qualifiers
REGION               1..21
                     note = Description of Artificial Sequence: Synthetic
                      Internal standard peptide sequence
MOD_RES              2
                     note = Carbamidomethylation
MOD_RES              21
                     note = K(13C6; 15N2)
source               1..21
                     mol_type = protein
                     organism = synthetic construct
SEQUENCE: 267
LCGAAGGLEN GLNYIDLDLV K                                                    21

SEQ ID NO: 268       moltype = AA  length = 21
FEATURE              Location/Qualifiers
REGION               1..21
                     note = Description of Artificial Sequence: Synthetic
```

```
                         Internal standard peptide sequence
MOD_RES                  21
                         note = K(13C6; 15N2)
source                   1..21
                         mol_type = protein
                         organism = synthetic construct
SEQUENCE: 268
LCGAAGGLEN GLNYIDLDLV K                                          21

SEQ ID NO: 269           moltype = AA  length = 13
FEATURE                  Location/Qualifiers
REGION                   1..13
                         note = Description of Artificial Sequence: Synthetic
                         Internal standard peptide sequence
MOD_RES                  13
                         note = R(13C6; 15N4)
source                   1..13
                         mol_type = protein
                         organism = synthetic construct
SEQUENCE: 269
SVSAPQQIIN PIR                                                   13

SEQ ID NO: 270           moltype = AA  length = 21
FEATURE                  Location/Qualifiers
REGION                   1..21
                         note = Description of Artificial Sequence: Synthetic
                         Internal standard peptide sequence
MOD_RES                  21
                         note = R(13C6; 15N4)
source                   1..21
                         mol_type = protein
                         organism = synthetic construct
SEQUENCE: 270
TESITATSPA SMVGGKPGSF R                                          21

SEQ ID NO: 271           moltype = AA  length = 12
FEATURE                  Location/Qualifiers
REGION                   1..12
                         note = Description of Artificial Sequence: Synthetic
                         Internal standard peptide sequence
MOD_RES                  12
                         note = R(13C6; 15N4)
source                   1..12
                         mol_type = protein
                         organism = synthetic construct
SEQUENCE: 271
TGIAAEEVSL PR                                                    12

SEQ ID NO: 272           moltype = AA  length = 14
FEATURE                  Location/Qualifiers
REGION                   1..14
                         note = Description of Artificial Sequence: Synthetic
                         Internal standard peptide sequence
MOD_RES                  14
                         note = R(13C6; 15N4)
source                   1..14
                         mol_type = protein
                         organism = synthetic construct
SEQUENCE: 272
SYPEEGLEMH PLER                                                  14

SEQ ID NO: 273           moltype = AA  length = 14
FEATURE                  Location/Qualifiers
REGION                   1..14
                         note = Description of Artificial Sequence: Synthetic
                         Internal standard peptide sequence
MOD_RES                  14
                         note = K(13C6; 15N2)
source                   1..14
                         mol_type = protein
                         organism = synthetic construct
SEQUENCE: 273
THSAGTSPTI THQK                                                  14

SEQ ID NO: 274           moltype = AA  length = 26
FEATURE                  Location/Qualifiers
REGION                   1..26
                         note = Description of Artificial Sequence: Synthetic
                         Internal standard peptide sequence
```

```
MOD_RES         3
                note = Phosphorylation
MOD_RES         26
                note = R(13C6; 15N4)
source          1..26
                mol_type = protein
                organism = synthetic construct
SEQUENCE: 274
ASSDGEGTMS RPASVDGSPV SPSTNR                                              26

SEQ ID NO: 275      moltype = AA  length = 14
FEATURE             Location/Qualifiers
REGION              1..14
                    note = Description of Artificial Sequence: Synthetic
                     Internal standard peptide sequence
MOD_RES         3
                note = Phosphorylation
MOD_RES         14
                note = R(13C6; 15N4)
source          1..14
                mol_type = protein
                organism = synthetic construct
SEQUENCE: 275
HSSETFSSTP SATR                                                           14

SEQ ID NO: 276      moltype = AA  length = 12
FEATURE             Location/Qualifiers
REGION              1..12
                    note = Description of Artificial Sequence: Synthetic
                     Internal standard peptide sequence
MOD_RES         10
                note = Phosphorylation
MOD_RES         12
                note = K(13C6; 15N2)
source          1..12
                mol_type = protein
                organism = synthetic construct
SEQUENCE: 276
KGSGDYMPMS PK                                                             12

SEQ ID NO: 277      moltype = AA  length = 12
FEATURE             Location/Qualifiers
REGION              1..12
                    note = Description of Artificial Sequence: Synthetic
                     Internal standard peptide sequence
MOD_RES         7
                note = Methionine sulfoxide
MOD_RES         9
                note = Methionine sulfoxide
MOD_RES         10
                note = Phosphorylation
MOD_RES         12
                note = K(13C6; 15N2)
source          1..12
                mol_type = protein
                organism = synthetic construct
SEQUENCE: 277
KGSGDYMPMS PK                                                             12

SEQ ID NO: 278      moltype = AA  length = 21
FEATURE             Location/Qualifiers
REGION              1..21
                    note = Description of Artificial Sequence: Synthetic
                     Internal standard peptide sequence
MOD_RES         2
                note = Carbamidomethylation
MOD_RES         14
                note = Phosphorylation
MOD_RES         21
                note = K(13C6; 15N2)
source          1..21
                mol_type = protein
                organism = synthetic construct
SEQUENCE: 278
LCGAAGGLEN GLNYIDLDLV K                                                   21

SEQ ID NO: 279      moltype = AA  length = 21
FEATURE             Location/Qualifiers
REGION              1..21
```

```
                        note = Description of Artificial Sequence: Synthetic
                            Internal standard peptide sequence
MOD_RES                 14
                        note = Phosphorylation
MOD_RES                 21
                        note = K(13C6; 15N2)
source                  1..21
                        mol_type = protein
                        organism = synthetic construct
SEQUENCE: 279
LCGAAGGLEN GLNYIDLDLV K                                                   21

SEQ ID NO: 280          moltype = AA  length = 21
FEATURE                 Location/Qualifiers
REGION                  1..21
                        note = Description of Artificial Sequence: Synthetic
                            Internal standard peptide sequence
MOD_RES                 8
                        note = Phosphorylation
MOD_RES                 21
                        note = R(13C6; 15N4)
source                  1..21
                        mol_type = protein
                        organism = synthetic construct
SEQUENCE: 280
TESITATSPA SMVGGKPGSF R                                                   21

SEQ ID NO: 281          moltype = AA  length = 21
FEATURE                 Location/Qualifiers
REGION                  1..21
                        note = Description of Artificial Sequence: Synthetic
                            Internal standard peptide sequence
MOD_RES                 8
                        note = Phosphorylation
MOD_RES                 12
                        note = Methionine sulfoxide
MOD_RES                 21
                        note = R(13C6; 15N4)
source                  1..21
                        mol_type = protein
                        organism = synthetic construct
SEQUENCE: 281
TESITATSPA SMVGGKPGSF R                                                   21

SEQ ID NO: 282          moltype = AA  length = 18
FEATURE                 Location/Qualifiers
REGION                  1..18
                        note = Description of Artificial Sequence: Synthetic
                            Internal standard peptide sequence
MOD_RES                 18
                        note = R(13C6; 15N4)
source                  1..18
                        mol_type = protein
                        organism = synthetic construct
SEQUENCE: 282
APAQTPAEPT PGYEVGQR                                                       18

SEQ ID NO: 283          moltype = AA  length = 15
FEATURE                 Location/Qualifiers
REGION                  1..15
                        note = Description of Artificial Sequence: Synthetic
                            Internal standard peptide sequence
MOD_RES                 15
                        note = K(13C6; 15N2)
source                  1..15
                        mol_type = protein
                        organism = synthetic construct
SEQUENCE: 283
DSFRARSTSL NERPK                                                          15

SEQ ID NO: 284          moltype = AA  length = 16
FEATURE                 Location/Qualifiers
REGION                  1..16
                        note = Description of Artificial Sequence: Synthetic
                            Internal standard peptide sequence
MOD_RES                 16
                        note = R(13C6; 15N4)
source                  1..16
                        mol_type = protein
```

```
                        organism = synthetic construct
SEQUENCE: 284
EAPAKLESQA GQQVSR                                                         16

SEQ ID NO: 285          moltype = AA   length = 11
FEATURE                 Location/Qualifiers
REGION                  1..11
                        note = Description of Artificial Sequence: Synthetic
                        Internal standard peptide sequence
MOD_RES                 11
                        note = R(13C6; 15N4)
source                  1..11
                        mol_type = protein
                        organism = synthetic construct
SEQUENCE: 285
GYTISDSAPS R                                                              11

SEQ ID NO: 286          moltype = AA   length = 12
FEATURE                 Location/Qualifiers
REGION                  1..12
                        note = Description of Artificial Sequence: Synthetic
                        Internal standard peptide sequence
MOD_RES                 12
                        note = V(13C5; 15N)
source                  1..12
                        mol_type = protein
                        organism = synthetic construct
SEQUENCE: 286
LISSVEDFTE FV                                                             12

SEQ ID NO: 287          moltype = AA   length = 13
FEATURE                 Location/Qualifiers
REGION                  1..13
                        note = Description of Artificial Sequence: Synthetic
                        Internal standard peptide sequence
MOD_RES                 13
                        note = R(13C6; 15N4)
source                  1..13
                        mol_type = protein
                        organism = synthetic construct
SEQUENCE: 287
LVTVTTSVGT GTR                                                            13

SEQ ID NO: 288          moltype = AA   length = 21
FEATURE                 Location/Qualifiers
REGION                  1..21
                        note = Description of Artificial Sequence: Synthetic
                        Internal standard peptide sequence
MOD_RES                 21
                        note = R(13C6; 15N4)
source                  1..21
                        mol_type = protein
                        organism = synthetic construct
SEQUENCE: 288
SQSGTLDGES AAWSASGEDS R                                                   21

SEQ ID NO: 289          moltype = AA   length = 15
FEATURE                 Location/Qualifiers
REGION                  1..15
                        note = Description of Artificial Sequence: Synthetic
                        Internal standard peptide sequence
MOD_RES                 15
                        note = K(13C6; 15N2)
source                  1..15
                        mol_type = protein
                        organism = synthetic construct
SEQUENCE: 289
SVQLLDQIPS YDTHK                                                          15

SEQ ID NO: 290          moltype = AA   length = 21
FEATURE                 Location/Qualifiers
REGION                  1..21
                        note = Description of Artificial Sequence: Synthetic
                        Internal standard peptide sequence
MOD_RES                 21
                        note = R(13C6; 15N4)
source                  1..21
                        mol_type = protein
                        organism = synthetic construct
```

```
SEQUENCE: 290
VGALDVPASQ FLGSATSPGP R                                              21

SEQ ID NO: 291          moltype = AA  length = 23
FEATURE                 Location/Qualifiers
REGION                  1..23
                        note = Description of Artificial Sequence: Synthetic
                        Internal standard peptide sequence
MOD_RES                 23
                        note = K(13C6; 15N2)
source                  1..23
                        mol_type = protein
                        organism = synthetic construct
SEQUENCE: 291
VVSSEGGRPS VDLSFQPSQP LSK                                            23

SEQ ID NO: 292          moltype = AA  length = 10
FEATURE                 Location/Qualifiers
REGION                  1..10
                        note = Description of Artificial Sequence: Synthetic
                        Internal standard peptide sequence
MOD_RES                 10
                        note = R(13C6; 15N4)
source                  1..10
                        mol_type = protein
                        organism = synthetic construct
SEQUENCE: 292
YTEFLTGLGR                                                           10

SEQ ID NO: 293          moltype = AA  length = 11
FEATURE                 Location/Qualifiers
REGION                  1..11
                        note = Description of Artificial Sequence: Synthetic
                        Internal standard peptide sequence
MOD_RES                 11
                        note = K(13C6; 15N2)
source                  1..11
                        mol_type = protein
                        organism = synthetic construct
SEQUENCE: 293
YVFSNFTAVP K                                                         11

SEQ ID NO: 294          moltype = AA  length = 10
FEATURE                 Location/Qualifiers
REGION                  1..10
                        note = Description of Artificial Sequence: Synthetic
                        Internal standard peptide sequence
MOD_RES                 10
                        note = K(13C6; 15N2)
source                  1..10
                        mol_type = protein
                        organism = synthetic construct
SEQUENCE: 294
SNPTDIYPSK                                                           10

SEQ ID NO: 295          moltype = AA  length = 12
FEATURE                 Location/Qualifiers
REGION                  1..12
                        note = Description of Artificial Sequence: Synthetic
                        Internal standard peptide sequence
MOD_RES                 12
                        note = R(13C6; 15N4)
source                  1..12
                        mol_type = protein
                        organism = synthetic construct
SEQUENCE: 295
FNSCYLDEYI AR                                                        12

SEQ ID NO: 296          moltype = AA  length = 13
FEATURE                 Location/Qualifiers
REGION                  1..13
                        note = Description of Artificial Sequence: Synthetic
                        Internal standard peptide sequence
MOD_RES                 13
                        note = R(13C6; 15N4)
source                  1..13
                        mol_type = protein
                        organism = synthetic construct
SEQUENCE: 296
```

```
GQPEGPLPSS SPR                                                             13

SEQ ID NO: 297         moltype = AA  length = 25
FEATURE                Location/Qualifiers
REGION                 1..25
                       note = Description of Artificial Sequence: Synthetic
                       Internal standard peptide sequence
MOD_RES                25
                       note = R(13C6; 15N4)
source                 1..25
                       mol_type = protein
                       organism = synthetic construct
SEQUENCE: 297
SLLGLDSGEL QSGPESSSSP GVHVR                                                25

SEQ ID NO: 298         moltype = AA  length = 15
FEATURE                Location/Qualifiers
REGION                 1..15
                       note = Description of Artificial Sequence: Synthetic
                       Internal standard peptide sequence
MOD_RES                9
                       note = Phosphorylation
MOD_RES                15
                       note = K(13C6; 15N2)
source                 1..15
                       mol_type = protein
                       organism = synthetic construct
SEQUENCE: 298
DSFRARSTSL NERPK                                                           15

SEQ ID NO: 299         moltype = AA  length = 11
FEATURE                Location/Qualifiers
REGION                 1..11
                       note = Description of Artificial Sequence: Synthetic
                       Internal standard peptide sequence
MOD_RES                3
                       note = Phosphorylation
MOD_RES                11
                       note = R(13C6; 15N4)
source                 1..11
                       mol_type = protein
                       organism = synthetic construct
SEQUENCE: 299
GYTISDSAPS R                                                               11

SEQ ID NO: 300         moltype = AA  length = 12
FEATURE                Location/Qualifiers
REGION                 1..12
                       note = Description of Artificial Sequence: Synthetic
                       Internal standard peptide sequence
MOD_RES                3
                       note = Phosphorylation
MOD_RES                12
                       note = V(13C5; 15N)
source                 1..12
                       mol_type = protein
                       organism = synthetic construct
SEQUENCE: 300
LISSVEDFTE FV                                                              12

SEQ ID NO: 301         moltype = AA  length = 12
FEATURE                Location/Qualifiers
REGION                 1..12
                       note = Description of Artificial Sequence: Synthetic
                       Internal standard peptide sequence
MOD_RES                4
                       note = Phosphorylation
MOD_RES                12
                       note = V(13C5; 15N)
source                 1..12
                       mol_type = protein
                       organism = synthetic construct
SEQUENCE: 301
LISSVEDFTE FV                                                              12

SEQ ID NO: 302         moltype = AA  length = 12
FEATURE                Location/Qualifiers
REGION                 1..12
                       note = Description of Artificial Sequence: Synthetic
```

```
                         -continued
                      Internal standard peptide sequence
MOD_RES               3..4
                      note = Phosphorylation
MOD_RES               12
                      note = V(13C5; 15N)
source                1..12
                      mol_type = protein
                      organism = synthetic construct
SEQUENCE: 302
LISSVEDFTE FV                                                       12

SEQ ID NO: 303        moltype = AA  length = 9
FEATURE               Location/Qualifiers
REGION                1..9
                      note = Description of Artificial Sequence: Synthetic
                      Internal standard peptide sequence
MOD_RES               3
                      note = Phosphorylation
MOD_RES               9
                      note = K(13C6; 15N2)
source                1..9
                      mol_type = protein
                      organism = synthetic construct
SEQUENCE: 303
STSLNERPK                                                            9

SEQ ID NO: 304        moltype = AA  length = 9
FEATURE               Location/Qualifiers
REGION                1..9
                      note = Description of Artificial Sequence: Synthetic
                      Internal standard peptide sequence
MOD_RES               9
                      note = K(13C6; 15N2)
source                1..9
                      mol_type = protein
                      organism = synthetic construct
SEQUENCE: 304
STSLNERPK                                                            9

SEQ ID NO: 305        moltype = AA  length = 19
FEATURE               Location/Qualifiers
REGION                1..19
                      note = Description of Artificial Sequence: Synthetic
                      Internal standard peptide sequence
MOD_RES               16
                      note = Carbamidomethylation
MOD_RES               19
                      note = K(13C6; 15N2)
source                1..19
                      mol_type = protein
                      organism = synthetic construct
SEQUENCE: 305
AVLALHQDLF SLAQQCIDK                                                19

SEQ ID NO: 306        moltype = AA  length = 19
FEATURE               Location/Qualifiers
REGION                1..19
                      note = Description of Artificial Sequence: Synthetic
                      Internal standard peptide sequence
MOD_RES               19
                      note = K(13C6; 15N2)
source                1..19
                      mol_type = protein
                      organism = synthetic construct
SEQUENCE: 306
AVLALHQDLF SLAQQCIDK                                                19

SEQ ID NO: 307        moltype = AA  length = 18
FEATURE               Location/Qualifiers
REGION                1..18
                      note = Description of Artificial Sequence: Synthetic
                      Internal standard peptide sequence
MOD_RES               18
                      note = R(13C6; 15N4)
source                1..18
                      mol_type = protein
                      organism = synthetic construct
SEQUENCE: 307
DLELAVPGTY DPNQPIIR                                                 18
```

```
SEQ ID NO: 308            moltype = AA   length = 9
FEATURE                   Location/Qualifiers
REGION                    1..9
                          note = Description of Artificial Sequence: Synthetic
                           Internal standard peptide sequence
MOD_RES                   9
                          note = R(13C6; 15N4)
source                    1..9
                          mol_type = protein
                          organism = synthetic construct
SEQUENCE: 308
GNNLQDTLR                                                                  9

SEQ ID NO: 309            moltype = AA   length = 16
FEATURE                   Location/Qualifiers
REGION                    1..16
                          note = Description of Artificial Sequence: Synthetic
                           Internal standard peptide sequence
MOD_RES                   16
                          note = K(13C6; 15N2)
source                    1..16
                          mol_type = protein
                          organism = synthetic construct
SEQUENCE: 309
GPTPAILESL ISINNK                                                         16

SEQ ID NO: 310            moltype = AA   length = 17
FEATURE                   Location/Qualifiers
REGION                    1..17
                          note = Description of Artificial Sequence: Synthetic
                           Internal standard peptide sequence
MOD_RES                   17
                          note = R(13C6; 15N4)
source                    1..17
                          mol_type = protein
                          organism = synthetic construct
SEQUENCE: 310
GYTLADEEED PLIYQHR                                                        17

SEQ ID NO: 311            moltype = AA   length = 13
FEATURE                   Location/Qualifiers
REGION                    1..13
                          note = Description of Artificial Sequence: Synthetic
                           Internal standard peptide sequence
MOD_RES                   13
                          note = R(13C6; 15N4)
source                    1..13
                          mol_type = protein
                          organism = synthetic construct
SEQUENCE: 311
IHGALLILNE LVR                                                            13

SEQ ID NO: 312            moltype = AA   length = 14
FEATURE                   Location/Qualifiers
REGION                    1..14
                          note = Description of Artificial Sequence: Synthetic
                           Internal standard peptide sequence
MOD_RES                   14
                          note = K(13C6; 15N2)
source                    1..14
                          mol_type = protein
                          organism = synthetic construct
SEQUENCE: 312
IQSIAPSLQV ITSK                                                           14

SEQ ID NO: 313            moltype = AA   length = 12
FEATURE                   Location/Qualifiers
REGION                    1..12
                          note = Description of Artificial Sequence: Synthetic
                           Internal standard peptide sequence
MOD_RES                   12
                          note = R(13C6; 15N4)
source                    1..12
                          mol_type = protein
                          organism = synthetic construct
SEQUENCE: 313
LFDAPEAPLP SR                                                             12
```

-continued

| | | |
|---|---|---|
| SEQ ID NO: 314<br>FEATURE<br>REGION<br><br>MOD_RES<br><br>source | moltype = AA   length = 18<br>Location/Qualifiers<br>1..18<br>note = Description of Artificial Sequence: Synthetic<br>Internal standard peptide sequence<br>18<br>note = K(13C6; 15N2)<br>1..18<br>mol_type = protein<br>organism = synthetic construct | |
| SEQUENCE: 314<br>LGEWQLNLQG INESTIPK | | 18 |
| SEQ ID NO: 315<br>FEATURE<br>REGION<br><br>MOD_RES<br><br>source | moltype = AA   length = 11<br>Location/Qualifiers<br>1..11<br>note = Description of Artificial Sequence: Synthetic<br>Internal standard peptide sequence<br>11<br>note = R(13C6; 15N4)<br>1..11<br>mol_type = protein<br>organism = synthetic construct | |
| SEQUENCE: 315<br>LIHQLLTDIG R | | 11 |
| SEQ ID NO: 316<br>FEATURE<br>REGION<br><br>MOD_RES<br><br>source | moltype = AA   length = 10<br>Location/Qualifiers<br>1..10<br>note = Description of Artificial Sequence: Synthetic<br>Internal standard peptide sequence<br>10<br>note = R(13C6; 15N4)<br>1..10<br>mol_type = protein<br>organism = synthetic construct | |
| SEQUENCE: 316<br>SPSSEVWFDR | | 10 |
| SEQ ID NO: 317<br>FEATURE<br>REGION<br><br>MOD_RES<br><br>source | moltype = AA   length = 24<br>Location/Qualifiers<br>1..24<br>note = Description of Artificial Sequence: Synthetic<br>Internal standard peptide sequence<br>24<br>note = K(13C6; 15N2)<br>1..24<br>mol_type = protein<br>organism = synthetic construct | |
| SEQUENCE: 317<br>TDSYSAGQSV EILDGVELGE PAHK | | 24 |
| SEQ ID NO: 318<br>FEATURE<br>REGION<br><br>MOD_RES<br><br>source | moltype = AA   length = 12<br>Location/Qualifiers<br>1..12<br>note = Description of Artificial Sequence: Synthetic<br>Internal standard peptide sequence<br>12<br>note = R(13C6; 15N4)<br>1..12<br>mol_type = protein<br>organism = synthetic construct | |
| SEQUENCE: 318<br>TLVLLLGVDP SR | | 12 |
| SEQ ID NO: 319<br>FEATURE<br>REGION<br><br>MOD_RES<br><br>source | moltype = AA   length = 18<br>Location/Qualifiers<br>1..18<br>note = Description of Artificial Sequence: Synthetic<br>Internal standard peptide sequence<br>18<br>note = K(13C6; 15N2)<br>1..18<br>mol_type = protein<br>organism = synthetic construct | |
| SEQUENCE: 319<br>VEVFEHAVNN TAGDDLAK | | 18 |
| SEQ ID NO: 320 | moltype = AA   length = 12 | |

```
FEATURE              Location/Qualifiers
REGION               1..12
                     note = Description of Artificial Sequence: Synthetic
                     Internal standard peptide sequence
MOD_RES              12
                     note = K(13C6; 15N2)
source               1..12
                     mol_type = protein
                     organism = synthetic construct
SEQUENCE: 320
VLGLLGALDP YK                                                             12

SEQ ID NO: 321       moltype = AA  length = 11
FEATURE              Location/Qualifiers
REGION               1..11
                     note = Description of Artificial Sequence: Synthetic
                     Internal standard peptide sequence
MOD_RES              11
                     note = K(13C6; 15N2)
source               1..11
                     mol_type = protein
                     organism = synthetic construct
SEQUENCE: 321
WTLVNDETQA K                                                              11

SEQ ID NO: 322       moltype = AA  length = 10
FEATURE              Location/Qualifiers
REGION               1..10
                     note = Description of Artificial Sequence: Synthetic
                     Internal standard peptide sequence
MOD_RES              10
                     note = R(13C6; 15N4)
source               1..10
                     mol_type = protein
                     organism = synthetic construct
SEQUENCE: 322
ETSFNQAYGR                                                                10

SEQ ID NO: 323       moltype = AA  length = 9
FEATURE              Location/Qualifiers
REGION               1..9
                     note = Description of Artificial Sequence: Synthetic
                     Internal standard peptide sequence
MOD_RES              9
                     note = R(13C6; 15N4)
source               1..9
                     mol_type = protein
                     organism = synthetic construct
SEQUENCE: 323
TLDQSPELR                                                                  9

SEQ ID NO: 324       moltype = AA  length = 24
FEATURE              Location/Qualifiers
REGION               1..24
                     note = Description of Artificial Sequence: Synthetic
                     Internal standard peptide sequence
MOD_RES              3
                     note = Phosphorylation
MOD_RES              24
                     note = K(13C6; 15N2)
source               1..24
                     mol_type = protein
                     organism = synthetic construct
SEQUENCE: 324
TDSYSAGQSV EILDGVELGE PAHK                                                24

SEQ ID NO: 325       moltype = AA  length = 24
FEATURE              Location/Qualifiers
REGION               1..24
                     note = Description of Artificial Sequence: Synthetic
                     Internal standard peptide sequence
MOD_RES              1
                     note = Phosphorylation
MOD_RES              24
                     note = K(13C6; 15N2)
source               1..24
                     mol_type = protein
                     organism = synthetic construct
SEQUENCE: 325
```

```
TDSYSAGQSV EILDGVELGE PAHK                                                          24

SEQ ID NO: 326          moltype = AA   length = 24
FEATURE                 Location/Qualifiers
REGION                  1..24
                        note = Description of Artificial Sequence: Synthetic
                         Internal standard peptide sequence
MOD_RES                 1
                        note = Phosphorylation
MOD_RES                 3
                        note = Phosphorylation
MOD_RES                 24
                        note = K(13C6; 15N2)
source                  1..24
                        mol_type = protein
                        organism = synthetic construct
SEQUENCE: 326
TDSYSAGQSV EILDGVELGE PAHK                                                          24

SEQ ID NO: 327          moltype = AA   length = 17
FEATURE                 Location/Qualifiers
REGION                  1..17
                        note = Description of Artificial Sequence: Synthetic
                         Internal standard peptide sequence
MOD_RES                 17
                        note = K(13C6; 15N2)
source                  1..17
                        mol_type = protein
                        organism = synthetic construct
SEQUENCE: 327
DIKPQNLLVD PDTAVLK                                                                  17

SEQ ID NO: 328          moltype = AA   length = 16
FEATURE                 Location/Qualifiers
REGION                  1..16
                        note = Description of Artificial Sequence: Synthetic
                         Internal standard peptide sequence
MOD_RES                 7
                        note = Carbamidomethylation
MOD_RES                 16
                        note = R(13C6; 15N4)
source                  1..16
                        mol_type = protein
                        organism = synthetic construct
SEQUENCE: 328
LSPLEACAHS FFDELR                                                                   16

SEQ ID NO: 329          moltype = AA   length = 16
FEATURE                 Location/Qualifiers
REGION                  1..16
                        note = Description of Artificial Sequence: Synthetic
                         Internal standard peptide sequence
MOD_RES                 16
                        note = R(13C6; 15N4)
source                  1..16
                        mol_type = protein
                        organism = synthetic construct
SEQUENCE: 329
LSPLEACAHS FFDELR                                                                   16

SEQ ID NO: 330          moltype = AA   length = 13
FEATURE                 Location/Qualifiers
REGION                  1..13
                        note = Description of Artificial Sequence: Synthetic
                         Internal standard peptide sequence
MOD_RES                 11
                        note = Carbamidomethylation
MOD_RES                 13
                        note = R(13C6; 15N4)
source                  1..13
                        mol_type = protein
                        organism = synthetic construct
SEQUENCE: 330
SLAYIHSQGV CHR                                                                      13

SEQ ID NO: 331          moltype = AA   length = 13
FEATURE                 Location/Qualifiers
REGION                  1..13
                        note = Description of Artificial Sequence: Synthetic
```

```
MOD_RES                    13
                           note = R(13C6; 15N4)
source                     1..13
                           mol_type = protein
                           organism = synthetic construct
SEQUENCE: 331
SLAYIHSQGV CHR                                                                          13

SEQ ID NO: 332             moltype = AA  length = 10
FEATURE                    Location/Qualifiers
REGION                     1..10
                           note = Description of Artificial Sequence: Synthetic
                           Internal standard peptide sequence
MOD_RES                    10
                           note = K(13C6; 15N2)
source                     1..10
                           mol_type = protein
                           organism = synthetic construct
SEQUENCE: 332
SQEVAYTDIK                                                                              10

SEQ ID NO: 333             moltype = AA  length = 20
FEATURE                    Location/Qualifiers
REGION                     1..20
                           note = Description of Artificial Sequence: Synthetic
                           Internal standard peptide sequence
MOD_RES                    9
                           note = Carbamidomethylation
MOD_RES                    20
                           note = R(13C6; 15N4)
source                     1..20
                           mol_type = protein
                           organism = synthetic construct
SEQUENCE: 333
TPPEAIALCS SLLEYTPSSR                                                                   20

SEQ ID NO: 334             moltype = AA  length = 20
FEATURE                    Location/Qualifiers
REGION                     1..20
                           note = Description of Artificial Sequence: Synthetic
                           Internal standard peptide sequence
MOD_RES                    20
                           note = R(13C6; 15N4)
source                     1..20
                           mol_type = protein
                           organism = synthetic construct
SEQUENCE: 334
TPPEAIALCS SLLEYTPSSR                                                                   20

SEQ ID NO: 335             moltype = AA  length = 32
FEATURE                    Location/Qualifiers
REGION                     1..32
                           note = Description of Artificial Sequence: Synthetic
                           Internal standard peptide sequence
MOD_RES                    32
                           note = K(13C6; 15N2)
source                     1..32
                           mol_type = protein
                           organism = synthetic construct
SEQUENCE: 335
TSSFAEPGGG GGGGGGPGG SASGPGGTGG GK                                                      32

SEQ ID NO: 336             moltype = AA  length = 14
FEATURE                    Location/Qualifiers
REGION                     1..14
                           note = Description of Artificial Sequence: Synthetic
                           Internal standard peptide sequence
MOD_RES                    14
                           note = R(13C6; 15N4)
source                     1..14
                           mol_type = protein
                           organism = synthetic construct
SEQUENCE: 336
VTTVVATLGQ GPER                                                                         14

SEQ ID NO: 337             moltype = AA  length = 18
FEATURE                    Location/Qualifiers
REGION                     1..18
```

```
                    note = Description of Artificial Sequence: Synthetic
                       Internal standard peptide sequence
MOD_RES             18
                    note = R(13C6; 15N4)
source              1..18
                    mol_type = protein
                    organism = synthetic construct
SEQUENCE: 337
DSGKVTTVVA TLGQGPER                                                       18

SEQ ID NO: 338      moltype = AA   length = 9
FEATURE             Location/Qualifiers
REGION              1..9
                    note = Description of Artificial Sequence: Synthetic
                       Internal standard peptide sequence
MOD_RES             9
                    note = K(13C6; 15N2)
source              1..9
                    mol_type = protein
                    organism = synthetic construct
SEQUENCE: 338
YFFYSSGEK                                                                  9

SEQ ID NO: 339      moltype = AA   length = 32
FEATURE             Location/Qualifiers
REGION              1..32
                    note = Description of Artificial Sequence: Synthetic
                       Internal standard peptide sequence
MOD_RES             3
                    note = Phosphorylation
MOD_RES             32
                    note = K(13C6; 15N2)
source              1..32
                    mol_type = protein
                    organism = synthetic construct
SEQUENCE: 339
TSSFAEPGGG GGGGGGGPGG SASGPGGTGG GK                                       32

SEQ ID NO: 340      moltype = AA   length = 18
FEATURE             Location/Qualifiers
REGION              1..18
                    note = Description of Artificial Sequence: Synthetic
                       Internal standard peptide sequence
MOD_RES             18
                    note = R(13C6; 15N4)
source              1..18
                    mol_type = protein
                    organism = synthetic construct
SEQUENCE: 340
DEVYLNLVLD YVPETVYR                                                       18

SEQ ID NO: 341      moltype = AA   length = 17
FEATURE             Location/Qualifiers
REGION              1..17
                    note = Description of Artificial Sequence: Synthetic
                       Internal standard peptide sequence
MOD_RES             17
                    note = K(13C6; 15N2)
source              1..17
                    mol_type = protein
                    organism = synthetic construct
SEQUENCE: 341
DIKPQNLLLD PDTAVLK                                                        17

SEQ ID NO: 342      moltype = AA   length = 29
FEATURE             Location/Qualifiers
REGION              1..29
                    note = Description of Artificial Sequence: Synthetic
                       Internal standard peptide sequence
MOD_RES             29
                    note = R(13C6; 15N4)
source              1..29
                    mol_type = protein
                    organism = synthetic construct
SEQUENCE: 342
DTPALFNFTT QELSSNPPLA TILIPPHAR                                           29

SEQ ID NO: 343      moltype = AA   length = 11
FEATURE             Location/Qualifiers
```

```
REGION                      1..11
                            note = Description of Artificial Sequence: Synthetic
                             Internal standard peptide sequence
MOD_RES                     2
                            note = Carbamidomethylation
MOD_RES                     11
                            note = K(13C6; 15N2)
source                      1..11
                            mol_type = protein
                            organism = synthetic construct
SEQUENCE: 343
LCDSGELVAI K                                                                11

SEQ ID NO: 344              moltype = AA  length = 11
FEATURE                     Location/Qualifiers
REGION                      1..11
                            note = Description of Artificial Sequence: Synthetic
                             Internal standard peptide sequence
MOD_RES                     11
                            note = K(13C6; 15N2)
source                      1..11
                            mol_type = protein
                            organism = synthetic construct
SEQUENCE: 344
LCDSGELVAI K                                                                11

SEQ ID NO: 345              moltype = AA  length = 9
FEATURE                     Location/Qualifiers
REGION                      1..9
                            note = Description of Artificial Sequence: Synthetic
                             Internal standard peptide sequence
MOD_RES                     9
                            note = R(13C6; 15N4)
source                      1..9
                            mol_type = protein
                            organism = synthetic construct
SEQUENCE: 345
LLEYTPTAR                                                                    9

SEQ ID NO: 346              moltype = AA  length = 13
FEATURE                     Location/Qualifiers
REGION                      1..13
                            note = Description of Artificial Sequence: Synthetic
                             Internal standard peptide sequence
MOD_RES                     11
                            note = Carbamidomethylation
MOD_RES                     13
                            note = R(13C6; 15N4)
source                      1..13
                            mol_type = protein
                            organism = synthetic construct
SEQUENCE: 346
SLAYIHSFGI CHR                                                              13

SEQ ID NO: 347              moltype = AA  length = 13
FEATURE                     Location/Qualifiers
REGION                      1..13
                            note = Description of Artificial Sequence: Synthetic
                             Internal standard peptide sequence
MOD_RES                     13
                            note = R(13C6; 15N4)
source                      1..13
                            mol_type = protein
                            organism = synthetic construct
SEQUENCE: 347
SLAYIHSFGI CHR                                                              13

SEQ ID NO: 348              moltype = AA  length = 21
FEATURE                     Location/Qualifiers
REGION                      1..21
                            note = Description of Artificial Sequence: Synthetic
                             Internal standard peptide sequence
MOD_RES                     8
                            note = Carbamidomethylation
MOD_RES                     21
                            note = K(13C6; 15N2)
source                      1..21
                            mol_type = protein
                            organism = synthetic construct
```

```
SEQUENCE: 348
TTSFAESCKP VQQPSAFGSM K                                              21

SEQ ID NO: 349           moltype = AA  length = 21
FEATURE                  Location/Qualifiers
REGION                   1..21
                         note = Description of Artificial Sequence: Synthetic
                          Internal standard peptide sequence
MOD_RES                  21
                         note = K(13C6; 15N2)
source                   1..21
                         mol_type = protein
                         organism = synthetic construct
SEQUENCE: 349
TTSFAESCKP VQQPSAFGSM K                                              21

SEQ ID NO: 350           moltype = AA  length = 21
FEATURE                  Location/Qualifiers
REGION                   1..21
                         note = Description of Artificial Sequence: Synthetic
                          Internal standard peptide sequence
MOD_RES                  8
                         note = Carbamidomethylation
MOD_RES                  20
                         note = Methionine sulfoxide
MOD_RES                  21
                         note = K(13C6; 15N2)
source                   1..21
                         mol_type = protein
                         organism = synthetic construct
SEQUENCE: 350
TTSFAESCKP VQQPSAFGSM K                                              21

SEQ ID NO: 351           moltype = AA  length = 21
FEATURE                  Location/Qualifiers
REGION                   1..21
                         note = Description of Artificial Sequence: Synthetic
                          Internal standard peptide sequence
MOD_RES                  20
                         note = Methionine sulfoxide
MOD_RES                  21
                         note = K(13C6; 15N2)
source                   1..21
                         mol_type = protein
                         organism = synthetic construct
SEQUENCE: 351
TTSFAESCKP VQQPSAFGSM K                                              21

SEQ ID NO: 352           moltype = AA  length = 24
FEATURE                  Location/Qualifiers
REGION                   1..24
                         note = Description of Artificial Sequence: Synthetic
                          Internal standard peptide sequence
source                   1..24
                         mol_type = protein
                         organism = synthetic construct
SEQUENCE: 352
VTTVVATPGQ GPDRPQEVSY TDTK                                           24

SEQ ID NO: 353           moltype = AA  length = 9
FEATURE                  Location/Qualifiers
REGION                   1..9
                         note = Description of Artificial Sequence: Synthetic
                          Internal standard peptide sequence
MOD_RES                  9
                         note = R(13C6; 15N4)
source                   1..9
                         mol_type = protein
                         organism = synthetic construct
SEQUENCE: 353
KLDHCNIVR                                                             9

SEQ ID NO: 354           moltype = AA  length = 13
FEATURE                  Location/Qualifiers
REGION                   1..13
                         note = Description of Artificial Sequence: Synthetic
                          Internal standard peptide sequence
MOD_RES                  13
                         note = R(13C6; 15N4)
```

```
source              1..13
                    mol_type = protein
                    organism = synthetic construct
SEQUENCE: 354
DSSGTGHFTS GVR                                                         13

SEQ ID NO: 355      moltype = AA  length = 21
FEATURE             Location/Qualifiers
REGION              1..21
                    note = Description of Artificial Sequence: Synthetic
                     Internal standard peptide sequence
MOD_RES             3
                    note = Phosphorylation
MOD_RES             8
                    note = Carbamidomethylation
MOD_RES             20
                    note = Methionine sulfoxide
MOD_RES             21
                    note = K(13C6; 15N2)
source              1..21
                    mol_type = protein
                    organism = synthetic construct
SEQUENCE: 355
TTSFAESCKP VQQPSAFGSM K                                                21

SEQ ID NO: 356      moltype = AA  length = 21
FEATURE             Location/Qualifiers
REGION              1..21
                    note = Description of Artificial Sequence: Synthetic
                     Internal standard peptide sequence
MOD_RES             3
                    note = Phosphorylation
MOD_RES             20
                    note = Methionine sulfoxide
MOD_RES             21
                    note = K(13C6; 15N2)
source              1..21
                    mol_type = protein
                    organism = synthetic construct
SEQUENCE: 356
TTSFAESCKP VQQPSAFGSM K                                                21

SEQ ID NO: 357      moltype = AA  length = 21
FEATURE             Location/Qualifiers
REGION              1..21
                    note = Description of Artificial Sequence: Synthetic
                     Internal standard peptide sequence
MOD_RES             3
                    note = Phosphorylation
MOD_RES             8
                    note = Carbamidomethylation
MOD_RES             21
                    note = K(13C6; 15N2)
source              1..21
                    mol_type = protein
                    organism = synthetic construct
SEQUENCE: 357
TTSFAESCKP VQQPSAFGSM K                                                21

SEQ ID NO: 358      moltype = AA  length = 21
FEATURE             Location/Qualifiers
REGION              1..21
                    note = Description of Artificial Sequence: Synthetic
                     Internal standard peptide sequence
MOD_RES             3
                    note = Phosphorylation
MOD_RES             21
                    note = K(13C6; 15N2)
source              1..21
                    mol_type = protein
                    organism = synthetic construct
SEQUENCE: 358
TTSFAESCKP VQQPSAFGSM K                                                21

SEQ ID NO: 359      moltype = AA  length = 11
FEATURE             Location/Qualifiers
REGION              1..11
                    note = Description of Artificial Sequence: Synthetic
                     Internal standard peptide sequence
```

```
MOD_RES              9
                     note = Carbamidomethylation
MOD_RES              11
                     note = R(13C6; 15N4)
source               1..11
                     mol_type = protein
                     organism = synthetic construct
SEQUENCE: 359
GEPNVSYICS R                                                        11

SEQ ID NO: 360       moltype = AA  length = 11
FEATURE              Location/Qualifiers
REGION               1..11
                     note = Description of Artificial Sequence: Synthetic
                      Internal standard peptide sequence
MOD_RES              11
                     note = R(13C6; 15N4)
source               1..11
                     mol_type = protein
                     organism = synthetic construct
SEQUENCE: 360
GEPNVSYICS R                                                        11

SEQ ID NO: 361       moltype = AA  length = 11
FEATURE              Location/Qualifiers
REGION               1..11
                     note = Description of Artificial Sequence: Synthetic
                      Internal standard peptide sequence
MOD_RES              7
                     note = Phosphorylation
MOD_RES              9
                     note = Carbamidomethylation
MOD_RES              11
                     note = R(13C6; 15N4)
source               1..11
                     mol_type = protein
                     organism = synthetic construct
SEQUENCE: 361
GEPNVSYICS R                                                        11

SEQ ID NO: 362       moltype = AA  length = 11
FEATURE              Location/Qualifiers
REGION               1..11
                     note = Description of Artificial Sequence: Synthetic
                      Internal standard peptide sequence
MOD_RES              7
                     note = Phosphorylation
MOD_RES              11
                     note = R(13C6; 15N4)
source               1..11
                     mol_type = protein
                     organism = synthetic construct
SEQUENCE: 362
GEPNVSYICS R                                                        11

SEQ ID NO: 363       moltype = AA  length = 11
FEATURE              Location/Qualifiers
REGION               1..11
                     note = Description of Artificial Sequence: Synthetic
                      Internal standard peptide sequence
MOD_RES              6
                     note = Phosphorylation
MOD_RES              9
                     note = Carbamidomethylation
MOD_RES              11
                     note = R(13C6; 15N4)
source               1..11
                     mol_type = protein
                     organism = synthetic construct
SEQUENCE: 363
GEPNVSYICS R                                                        11

SEQ ID NO: 364       moltype = AA  length = 11
FEATURE              Location/Qualifiers
REGION               1..11
                     note = Description of Artificial Sequence: Synthetic
                      Internal standard peptide sequence
MOD_RES              6
                     note = Phosphorylation
```

```
MOD_RES                 11
                        note = R(13C6; 15N4)
source                  1..11
                        mol_type = protein
                        organism = synthetic construct
SEQUENCE: 364
GEPNVSYICS R                                                                    11

SEQ ID NO: 365          moltype = AA  length = 11
FEATURE                 Location/Qualifiers
REGION                  1..11
                        note = Description of Artificial Sequence: Synthetic
                         Internal standard peptide sequence
MOD_RES                 6..7
                        note = Phosphorylation
MOD_RES                 9
                        note = Carbamidomethylation
MOD_RES                 11
                        note = R(13C6; 15N4)
source                  1..11
                        mol_type = protein
                        organism = synthetic construct
SEQUENCE: 365
GEPNVSYICS R                                                                    11

SEQ ID NO: 366          moltype = AA  length = 11
FEATURE                 Location/Qualifiers
REGION                  1..11
                        note = Description of Artificial Sequence: Synthetic
                         Internal standard peptide sequence
MOD_RES                 6..7
                        note = Phosphorylation
MOD_RES                 11
                        note = R(13C6; 15N4)
source                  1..11
                        mol_type = protein
                        organism = synthetic construct
SEQUENCE: 366
GEPNVSYICS R                                                                    11

SEQ ID NO: 367          moltype = AA  length = 11
FEATURE                 Location/Qualifiers
REGION                  1..11
                        note = Description of Artificial Sequence: Synthetic
                         Internal standard peptide sequence
MOD_RES                 11
                        note = R(13C6; 15N4)
source                  1..11
                        mol_type = protein
                        organism = synthetic construct
SEQUENCE: 367
TPPEAIALCS R                                                                    11

SEQ ID NO: 368          moltype = AA  length = 11
FEATURE                 Location/Qualifiers
REGION                  1..11
                        note = Description of Artificial Sequence: Synthetic
                         Internal standard peptide sequence
MOD_RES                 9
                        note = Carbamidomethylation
MOD_RES                 11
                        note = R(13C6; 15N4)
source                  1..11
                        mol_type = protein
                        organism = synthetic construct
SEQUENCE: 368
TPPEAIALCS R                                                                    11

SEQ ID NO: 369          moltype = AA  length = 10
FEATURE                 Location/Qualifiers
REGION                  1..10
                        note = Description of Artificial Sequence: Synthetic
                         Internal standard peptide sequence
MOD_RES                 10
                        note = R(13C6; 15N4)
source                  1..10
                        mol_type = protein
                        organism = synthetic construct
SEQUENCE: 369
```

```
DGFYPAPDFR                                                                       10

SEQ ID NO: 370          moltype = AA   length = 16
FEATURE                 Location/Qualifiers
REGION                  1..16
                        note = Description of Artificial Sequence: Synthetic
                        Internal standard peptide sequence
MOD_RES                 16
                        note = K(13C6; 15N2)
source                  1..16
                        mol_type = protein
                        organism = synthetic construct
SEQUENCE: 370
DLKPENIMLN HQGHVK                                                                16

SEQ ID NO: 371          moltype = AA   length = 10
FEATURE                 Location/Qualifiers
REGION                  1..10
                        note = Description of Artificial Sequence: Synthetic
                        Internal standard peptide sequence
MOD_RES                 10
                        note = R(13C6; 15N4)
source                  1..10
                        mol_type = protein
                        organism = synthetic construct
SEQUENCE: 371
FEISETSVNR                                                                       10

SEQ ID NO: 372          moltype = AA   length = 9
FEATURE                 Location/Qualifiers
REGION                  1..9
                        note = Description of Artificial Sequence: Synthetic
                        Internal standard peptide sequence
MOD_RES                 9
                        note = R(13C6; 15N4)
source                  1..9
                        mol_type = protein
                        organism = synthetic construct
SEQUENCE: 372
FSPGDFWGR                                                                        9

SEQ ID NO: 373          moltype = AA   length = 10
FEATURE                 Location/Qualifiers
REGION                  1..10
                        note = Description of Artificial Sequence: Synthetic
                        Internal standard peptide sequence
MOD_RES                 10
                        note = R(13C6; 15N4)
source                  1..10
                        mol_type = protein
                        organism = synthetic construct
SEQUENCE: 373
HINWEELLAR                                                                       10

SEQ ID NO: 374          moltype = AA   length = 16
FEATURE                 Location/Qualifiers
REGION                  1..16
                        note = Description of Artificial Sequence: Synthetic
                        Internal standard peptide sequence
MOD_RES                 16
                        note = K(13C6; 15N2)
source                  1..16
                        mol_type = protein
                        organism = synthetic construct
SEQUENCE: 374
HPFIVDLIYA FQTGGK                                                                16

SEQ ID NO: 375          moltype = AA   length = 10
FEATURE                 Location/Qualifiers
REGION                  1..10
                        note = Description of Artificial Sequence: Synthetic
                        Internal standard peptide sequence
MOD_RES                 5
                        note = Carbamidomethylation
MOD_RES                 10
                        note = R(13C6; 15N4)
source                  1..10
                        mol_type = protein
                        organism = synthetic construct
```

```
SEQUENCE: 375
IRPECFELLR                                                                 10

SEQ ID NO: 376         moltype = AA  length = 10
FEATURE                Location/Qualifiers
REGION                 1..10
                       note = Description of Artificial Sequence: Synthetic
                        Internal standard peptide sequence
MOD_RES                10
                       note = R(13C6; 15N4)
source                 1..10
                       mol_type = protein
                       organism = synthetic construct
SEQUENCE: 376
IRPECFELLR                                                                 10

SEQ ID NO: 377         moltype = AA  length = 18
FEATURE                Location/Qualifiers
REGION                 1..18
                       note = Description of Artificial Sequence: Synthetic
                        Internal standard peptide sequence
MOD_RES                18
                       note = R(13C6; 15N4)
source                 1..18
                       mol_type = protein
                       organism = synthetic construct
SEQUENCE: 377
LGAGPGDAGE VQAHPFFR                                                        18

SEQ ID NO: 378         moltype = AA  length = 12
FEATURE                Location/Qualifiers
REGION                 1..12
                       note = Description of Artificial Sequence: Synthetic
                        Internal standard peptide sequence
MOD_RES                12
                       note = R(13C6; 15N4)
source                 1..12
                       mol_type = protein
                       organism = synthetic construct
SEQUENCE: 378
LNLPPYLTQE AR                                                              12

SEQ ID NO: 379         moltype = AA  length = 8
FEATURE                Location/Qualifiers
REGION                 1..8
                       note = Description of Artificial Sequence: Synthetic
                        Internal standard peptide sequence
MOD_RES                7
                       note = Carbamidomethylation
MOD_RES                8
                       note = K(13C6; 15N2)
source                 1..8
                       mol_type = protein
                       organism = synthetic construct
SEQUENCE: 379
LTDFGLCK                                                                   8

SEQ ID NO: 380         moltype = AA  length = 8
FEATURE                Location/Qualifiers
REGION                 1..8
                       note = Description of Artificial Sequence: Synthetic
                        Internal standard peptide sequence
MOD_RES                8
                       note = K(13C6; 15N2)
source                 1..8
                       mol_type = protein
                       organism = synthetic construct
SEQUENCE: 380
LTDFGLCK                                                                   8

SEQ ID NO: 381         moltype = AA  length = 35
FEATURE                Location/Qualifiers
REGION                 1..35
                       note = Description of Artificial Sequence: Synthetic
                        Internal standard peptide sequence
MOD_RES                35
                       note = K(13C6; 15N2)
source                 1..35
                       mol_type = protein
```

```
                              organism = synthetic construct
SEQUENCE: 381
QTPVDSPDDS TLSESANQVF LGFTYVAPSV LESVK                              35

SEQ ID NO: 382            moltype = AA  length = 7
FEATURE                   Location/Qualifiers
REGION                    1..7
                          note = Description of Artificial Sequence: Synthetic
                            Internal standard peptide sequence
MOD_RES                   7
                          note = K(13C6; 15N2)
source                    1..7
                          mol_type = protein
                          organism = synthetic construct
SEQUENCE: 382
TPVSPVK                                                              7

SEQ ID NO: 383            moltype = AA  length = 16
FEATURE                   Location/Qualifiers
REGION                    1..16
                          note = Description of Artificial Sequence: Synthetic
                            Internal standard peptide sequence
MOD_RES                   16
                          note = R(13C6; 15N4)
source                    1..16
                          mol_type = protein
                          organism = synthetic construct
SEQUENCE: 383
TPVSPVKFSP GDFWGR                                                    16

SEQ ID NO: 384            moltype = AA  length = 35
FEATURE                   Location/Qualifiers
REGION                    1..35
                          note = Description of Artificial Sequence: Synthetic
                            Internal standard peptide sequence
MOD_RES                   24
                          note = Phosphorylation
MOD_RES                   35
                          note = K(13C6; 15N2)
source                    1..35
                          mol_type = protein
                          organism = synthetic construct
SEQUENCE: 384
QTPVDSPDDS TLSESANQVF LGFTYVAPSV LESVK                              35

SEQ ID NO: 385            moltype = AA  length = 35
FEATURE                   Location/Qualifiers
REGION                    1..35
                          note = Description of Artificial Sequence: Synthetic
                            Internal standard peptide sequence
MOD_RES                   6
                          note = Phosphorylation
MOD_RES                   35
                          note = K(13C6; 15N2)
source                    1..35
                          mol_type = protein
                          organism = synthetic construct
SEQUENCE: 385
QTPVDSPDDS TLSESANQVF LGFTYVAPSV LESVK                              35

SEQ ID NO: 386            moltype = AA  length = 35
FEATURE                   Location/Qualifiers
REGION                    1..35
                          note = Description of Artificial Sequence: Synthetic
                            Internal standard peptide sequence
MOD_RES                   6
                          note = Phosphorylation
MOD_RES                   24
                          note = Phosphorylation
MOD_RES                   35
                          note = K(13C6; 15N2)
source                    1..35
                          mol_type = protein
                          organism = synthetic construct
SEQUENCE: 386
QTPVDSPDDS TLSESANQVF LGFTYVAPSV LESVK                              35

SEQ ID NO: 387            moltype = AA  length = 7
FEATURE                   Location/Qualifiers
```

```
REGION                    1..7
                          note = Description of Artificial Sequence: Synthetic
                          Internal standard peptide sequence
MOD_RES                   1
                          note = Phosphorylation
MOD_RES                   7
                          note = K(13C6; 15N2)
source                    1..7
                          mol_type = protein
                          organism = synthetic construct
SEQUENCE: 387
TPVSPVK                                                                        7

SEQ ID NO: 388            moltype = AA  length = 7
FEATURE                   Location/Qualifiers
REGION                    1..7
                          note = Description of Artificial Sequence: Synthetic
                          Internal standard peptide sequence
MOD_RES                   4
                          note = Phosphorylation
MOD_RES                   7
                          note = K(13C6; 15N2)
source                    1..7
                          mol_type = protein
                          organism = synthetic construct
SEQUENCE: 388
TPVSPVK                                                                        7

SEQ ID NO: 389            moltype = AA  length = 7
FEATURE                   Location/Qualifiers
REGION                    1..7
                          note = Description of Artificial Sequence: Synthetic
                          Internal standard peptide sequence
MOD_RES                   1
                          note = Phosphorylation
MOD_RES                   4
                          note = Phosphorylation
MOD_RES                   7
                          note = K(13C6; 15N2)
source                    1..7
                          mol_type = protein
                          organism = synthetic construct
SEQUENCE: 389
TPVSPVK                                                                        7

SEQ ID NO: 390            moltype = AA  length = 16
FEATURE                   Location/Qualifiers
REGION                    1..16
                          note = Description of Artificial Sequence: Synthetic
                          Internal standard peptide sequence
MOD_RES                   4
                          note = Phosphorylation
MOD_RES                   16
                          note = R(13C6; 15N4)
source                    1..16
                          mol_type = protein
                          organism = synthetic construct
SEQUENCE: 390
TPVSPVKFSP GDFWGR                                                              16

SEQ ID NO: 391            moltype = AA  length = 16
FEATURE                   Location/Qualifiers
REGION                    1..16
                          note = Description of Artificial Sequence: Synthetic
                          Internal standard peptide sequence
MOD_RES                   1
                          note = Phosphorylation
MOD_RES                   4
                          note = Phosphorylation
MOD_RES                   16
                          note = R(13C6; 15N4)
source                    1..16
                          mol_type = protein
                          organism = synthetic construct
SEQUENCE: 391
TPVSPVKFSP GDFWGR                                                              16

SEQ ID NO: 392            moltype = AA  length = 16
FEATURE                   Location/Qualifiers
```

```
REGION                  1..16
                        note = Description of Artificial Sequence: Synthetic
                         Internal standard peptide sequence
MOD_RES                 1
                        note = Phosphorylation
MOD_RES                 16
                        note = R(13C6; 15N4)
source                  1..16
                        mol_type = protein
                        organism = synthetic construct
SEQUENCE: 392
TPVSPVKFSP GDFWGR                                                       16

SEQ ID NO: 393          moltype = AA   length = 12
FEATURE                 Location/Qualifiers
REGION                  1..12
                        note = Description of Artificial Sequence: Synthetic
                         Internal standard peptide sequence
MOD_RES                 12
                        note = R(13C6; 15N4)
source                  1..12
                        mol_type = protein
                        organism = synthetic construct
SEQUENCE: 393
DIPGLTDTTV PR                                                           12

SEQ ID NO: 394          moltype = AA   length = 8
FEATURE                 Location/Qualifiers
REGION                  1..8
                        note = Description of Artificial Sequence: Synthetic
                         Internal standard peptide sequence
MOD_RES                 4
                        note = Carbamidomethylation
MOD_RES                 8
                        note = R(13C6; 15N4)
source                  1..8
                        mol_type = protein
                        organism = synthetic construct
SEQUENCE: 394
GHSCYRPR                                                                8

SEQ ID NO: 395          moltype = AA   length = 8
FEATURE                 Location/Qualifiers
REGION                  1..8
                        note = Description of Artificial Sequence: Synthetic
                         Internal standard peptide sequence
MOD_RES                 8
                        note = R(13C6; 15N4)
source                  1..8
                        mol_type = protein
                        organism = synthetic construct
SEQUENCE: 395
GHSCYRPR                                                                8

SEQ ID NO: 396          moltype = AA   length = 12
FEATURE                 Location/Qualifiers
REGION                  1..12
                        note = Description of Artificial Sequence: Synthetic
                         Internal standard peptide sequence
MOD_RES                 10
                        note = Carbamidomethylation
MOD_RES                 12
                        note = K(13C6; 15N2)
source                  1..12
                        mol_type = protein
                        organism = synthetic construct
SEQUENCE: 396
LNISFPATGC QK                                                           12

SEQ ID NO: 397          moltype = AA   length = 12
FEATURE                 Location/Qualifiers
REGION                  1..12
                        note = Description of Artificial Sequence: Synthetic
                         Internal standard peptide sequence
MOD_RES                 12
                        note = K(13C6; 15N2)
source                  1..12
                        mol_type = protein
                        organism = synthetic construct
```

```
SEQUENCE: 397
LNISFPATGC QK                                                                   12

SEQ ID NO: 398          moltype = AA  length = 15
FEATURE                 Location/Qualifiers
REGION                  1..15
                        note = Description of Artificial Sequence: Synthetic
                         Internal standard peptide sequence
MOD_RES                 15
                        note = K(13C6; 15N2)
source                  1..15
                        mol_type = protein
                        organism = synthetic construct
SEQUENCE: 398
MATEVAADAL GEEWK                                                                15

SEQ ID NO: 399          moltype = AA  length = 13
FEATURE                 Location/Qualifiers
REGION                  1..13
                        note = Description of Artificial Sequence: Synthetic
                         Internal standard peptide sequence
MOD_RES                 13
                        note = K(13C6; 15N2)
source                  1..13
                        mol_type = protein
                        organism = synthetic construct
SEQUENCE: 399
RRRLSSLRAS TSK                                                                  13

SEQ ID NO: 400          moltype = AA  length = 13
FEATURE                 Location/Qualifiers
REGION                  1..13
                        note = Description of Artificial Sequence: Synthetic
                         Internal standard peptide sequence
MOD_RES                 5
                        note = Phosphorylation
MOD_RES                 13
                        note = K(13C6; 15N2)
source                  1..13
                        mol_type = protein
                        organism = synthetic construct
SEQUENCE: 400
RRRLSSLRAS TSK                                                                  13

SEQ ID NO: 401          moltype = AA  length = 13
FEATURE                 Location/Qualifiers
REGION                  1..13
                        note = Description of Artificial Sequence: Synthetic
                         Internal standard peptide sequence
MOD_RES                 6
                        note = Phosphorylation
MOD_RES                 13
                        note = K(13C6; 15N2)
source                  1..13
                        mol_type = protein
                        organism = synthetic construct
SEQUENCE: 401
RRRLSSLRAS TSK                                                                  13

SEQ ID NO: 402          moltype = AA  length = 13
FEATURE                 Location/Qualifiers
REGION                  1..13
                        note = Description of Artificial Sequence: Synthetic
                         Internal standard peptide sequence
MOD_RES                 5..6
                        note = Phosphorylation
MOD_RES                 13
                        note = K(13C6; 15N2)
source                  1..13
                        mol_type = protein
                        organism = synthetic construct
SEQUENCE: 402
RRRLSSLRAS TSK                                                                  13

SEQ ID NO: 403          moltype = AA  length = 30
FEATURE                 Location/Qualifiers
REGION                  1..30
                        note = Description of Artificial Sequence: Synthetic
                         Internal standard peptide sequence
```

```
MOD_RES          30
                 note = R(13C6; 15N4)
source           1..30
                 mol_type = protein
                 organism = synthetic construct
SEQUENCE: 403
AATAARPPAP PPAPQPPSPT PSPPRPTLAR                                          30

SEQ ID NO: 404   moltype = AA  length = 10
FEATURE          Location/Qualifiers
REGION           1..10
                 note = Description of Artificial Sequence: Synthetic
                  Internal standard peptide sequence
MOD_RES          1
                 note = Carbamidomethylation
MOD_RES          10
                 note = R(13C6; 15N4)
source           1..10
                 mol_type = protein
                 organism = synthetic construct
SEQUENCE: 404
CLHDIALAHR                                                                10

SEQ ID NO: 405   moltype = AA  length = 10
FEATURE          Location/Qualifiers
REGION           1..10
                 note = Description of Artificial Sequence: Synthetic
                  Internal standard peptide sequence
MOD_RES          10
                 note = R(13C6; 15N4)
source           1..10
                 mol_type = protein
                 organism = synthetic construct
SEQUENCE: 405
CLHDIALAHR                                                                10

SEQ ID NO: 406   moltype = AA  length = 15
FEATURE          Location/Qualifiers
REGION           1..15
                 note = Description of Artificial Sequence: Synthetic
                  Internal standard peptide sequence
MOD_RES          15
                 note = R(13C6; 15N4)
source           1..15
                 mol_type = protein
                 organism = synthetic construct
SEQUENCE: 406
EAEDTQVFGD LPRPR                                                          15

SEQ ID NO: 407   moltype = AA  length = 12
FEATURE          Location/Qualifiers
REGION           1..12
                 note = Description of Artificial Sequence: Synthetic
                  Internal standard peptide sequence
MOD_RES          12
                 note = K(13C6; 15N2)
source           1..12
                 mol_type = protein
                 organism = synthetic construct
SEQUENCE: 407
SLPVSVPVWG FK                                                             12

SEQ ID NO: 408   moltype = AA  length = 16
FEATURE          Location/Qualifiers
REGION           1..16
                 note = Description of Artificial Sequence: Synthetic
                  Internal standard peptide sequence
MOD_RES          16
                 note = R(13C6; 15N4)
source           1..16
                 mol_type = protein
                 organism = synthetic construct
SEQUENCE: 408
SSDEENGPPS SPDLDR                                                         16

SEQ ID NO: 409   moltype = AA  length = 20
FEATURE          Location/Qualifiers
REGION           1..20
                 note = Description of Artificial Sequence: Synthetic
```

```
                        -continued

Internal standard peptide sequence
MOD_RES                 20
                        note = R(13C6; 15N4)
source                  1..20
                        mol_type = protein
                        organism = synthetic construct
SEQUENCE: 409
TEARSSDEEN GPPSSPDLDR                                              20

SEQ ID NO: 410          moltype = AA  length = 28
FEATURE                 Location/Qualifiers
REGION                  1..28
                        note = Description of Artificial Sequence: Synthetic
                        Internal standard peptide sequence
MOD_RES                 21
                        note = Carbamidomethylation
MOD_RES                 28
                        note = R(13C6; 15N4)
source                  1..28
                        mol_type = protein
                        organism = synthetic construct
SEQUENCE: 410
TGTELVLLTA APPPPPRPGP CAYAAHGR                                     28

SEQ ID NO: 411          moltype = AA  length = 28
FEATURE                 Location/Qualifiers
REGION                  1..28
                        note = Description of Artificial Sequence: Synthetic
                        Internal standard peptide sequence
MOD_RES                 28
                        note = R(13C6; 15N4)
source                  1..28
                        mol_type = protein
                        organism = synthetic construct
SEQUENCE: 411
TGTELVLLTA APPPPPRPGP CAYAAHGR                                     28

SEQ ID NO: 412          moltype = AA  length = 8
FEATURE                 Location/Qualifiers
REGION                  1..8
                        note = Description of Artificial Sequence: Synthetic
                        Internal standard peptide sequence
MOD_RES                 8
                        note = K(13C6; 15N2)
source                  1..8
                        mol_type = protein
                        organism = synthetic construct
SEQUENCE: 412
LNTSDFQK                                                            8

SEQ ID NO: 413          moltype = AA  length = 23
FEATURE                 Location/Qualifiers
REGION                  1..23
                        note = Description of Artificial Sequence: Synthetic
                        Internal standard peptide sequence
MOD_RES                 23
                        note = K(13C6; 15N2)
source                  1..23
                        mol_type = protein
                        organism = synthetic construct
SEQUENCE: 413
EAEDTQVFGD LPRPRLNTSD FQK                                          23

SEQ ID NO: 414          moltype = AA  length = 8
FEATURE                 Location/Qualifiers
REGION                  1..8
                        note = Description of Artificial Sequence: Synthetic
                        Internal standard peptide sequence
MOD_RES                 8
                        note = R(13C6; 15N4)
source                  1..8
                        mol_type = protein
                        organism = synthetic construct
SEQUENCE: 414
GALAEAAR                                                            8

SEQ ID NO: 415          moltype = AA  length = 18
FEATURE                 Location/Qualifiers
REGION                  1..18
```

```
                        note = Description of Artificial Sequence: Synthetic
                          Internal standard peptide sequence
MOD_RES                 18
                        note = R(13C6; 15N4)
source                  1..18
                        mol_type = protein
                        organism = synthetic construct
SEQUENCE: 415
ASGRPEELWE AVVGAAER                                                      18

SEQ ID NO: 416          moltype = AA  length = 8
FEATURE                 Location/Qualifiers
REGION                  1..8
                        note = Description of Artificial Sequence: Synthetic
                          Internal standard peptide sequence
MOD_RES                 3
                        note = Phosphorylation
MOD_RES                 8
                        note = K(13C6; 15N2)
source                  1..8
                        mol_type = protein
                        organism = synthetic construct
SEQUENCE: 416
LNTSDFQK                                                                  8

SEQ ID NO: 417          moltype = AA  length = 23
FEATURE                 Location/Qualifiers
REGION                  1..23
                        note = Description of Artificial Sequence: Synthetic
                          Internal standard peptide sequence
MOD_RES                 18
                        note = Phosphorylation
MOD_RES                 23
                        note = K(13C6; 15N2)
source                  1..23
                        mol_type = protein
                        organism = synthetic construct
SEQUENCE: 417
EAEDTQVFGD LPRPRLNTSD FQK                                                23

SEQ ID NO: 418          moltype = AA  length = 24
FEATURE                 Location/Qualifiers
REGION                  1..24
                        note = Description of Artificial Sequence: Synthetic
                          Internal standard peptide sequence
MOD_RES                 24
                        note = K(13C6; 15N2)
source                  1..24
                        mol_type = protein
                        organism = synthetic construct
SEQUENCE: 418
YSDTTDSDPE NEPFDEDQHT QITK                                               24

SEQ ID NO: 419          moltype = AA  length = 25
FEATURE                 Location/Qualifiers
REGION                  1..25
                        note = Description of Artificial Sequence: Synthetic
                          Internal standard peptide sequence
MOD_RES                 24
                        note = K(13C6; 15N2)
source                  1..25
                        mol_type = protein
                        organism = synthetic construct
SEQUENCE: 419
YSDTTDSDPE NEPFDEDQHT QITKV                                              25

SEQ ID NO: 420          moltype = AA  length = 8
FEATURE                 Location/Qualifiers
REGION                  1..8
                        note = Description of Artificial Sequence: Synthetic
                          Internal standard peptide sequence
MOD_RES                 8
                        note = R(13C6; 15N4)
source                  1..8
                        mol_type = protein
                        organism = synthetic construct
SEQUENCE: 420
NNIDDVVR                                                                  8
```

```
SEQ ID NO: 421           moltype = AA   length = 12
FEATURE                  Location/Qualifiers
REGION                   1..12
                         note = Description of Artificial Sequence: Synthetic
                         Internal standard peptide sequence
MOD_RES                  12
                         note = R(13C6; 15N4)
source                   1..12
                         mol_type = protein
                         organism = synthetic construct
SEQUENCE: 421
AQEALDFYGE VR                                                              12

SEQ ID NO: 422           moltype = AA   length = 10
FEATURE                  Location/Qualifiers
REGION                   1..10
                         note = Description of Artificial Sequence: Synthetic
                         Internal standard peptide sequence
MOD_RES                  10
                         note = R(13C6; 15N4)
source                   1..10
                         mol_type = protein
                         organism = synthetic construct
SEQUENCE: 422
IYSSNSGPTR                                                                 10

SEQ ID NO: 423           moltype = AA   length = 24
FEATURE                  Location/Qualifiers
REGION                   1..24
                         note = Description of Artificial Sequence: Synthetic
                         Internal standard peptide sequence
MOD_RES                  2
                         note = Phosphorylation
MOD_RES                  24
                         note = K(13C6; 15N2)
source                   1..24
                         mol_type = protein
                         organism = synthetic construct
SEQUENCE: 423
YSDTTDSDPE NEPFDEDQHT QITK                                                 24

SEQ ID NO: 424           moltype = AA   length = 25
FEATURE                  Location/Qualifiers
REGION                   1..25
                         note = Description of Artificial Sequence: Synthetic
                         Internal standard peptide sequence
MOD_RES                  2
                         note = Phosphorylation
MOD_RES                  24
                         note = K(13C6; 15N2)
source                   1..25
                         mol_type = protein
                         organism = synthetic construct
SEQUENCE: 424
YSDTTDSDPE NEPFDEDQHT QITKV                                                25
```

DETECTION AND QUANTIFICATION OF AKT-mTOR PATHWAY PROTEINS

CROSS-REFERENCE TO RELATED APPLICATIONS

This application is a divisional of U.S. patent application Ser. No. 16/081,377, filed Aug. 30, 2018, which is a 371 of International Application No. PCT/US2017/022062, filed Mar. 13, 2017, which claims the benefit of priority of U.S. Provisional Patent Application No. 62/308,051, filed Mar. 14, 2016, which is incorporated by reference herein in its entirety for all purposes.

SEQUENCE LISTING

The instant application contains a sequence listing which has been submitted electronically in xml format and is hereby incorporated by reference in its entirety. Said xml copy, created on Dec. 12, 2022, is named 2022-12-12_01129-0092-01US_ST26.xml and is 709,180 bytes in size.

FIELD OF INVENTION

This disclosure relates to the field of detection and quantification of AKT-mTOR pathway proteins, including phosphorylated proteins, by immunoprecipitation and mass spectrometry.

BACKGROUND

The AKT-mTOR pathway plays a central role in tumor progression and anti-cancer drug resistance. The quantitative measurement of protein expression and post-translational modifications of the AKT-mTOR pathway is necessary for precisely characterizing cancer, monitoring cancer progression, and determining treatment responses. See Logue, J. S.; Morrison, D. K.; *Genes Dev*. Apr. 1 2012, 26 (7), 641-50.

A major limitation in the detection and quantitation of AKT-mTOR pathway proteins is the lack of rigorously validated methods and reagents. Currently, only semi-quantitative results from Western blotting, ELISA, and Luminex assays are available. Mass spectrometry (MS) is increasingly becoming the detection methodology of choice for assaying protein abundance and post-translational modifications. However, to date, MS has not been successful in quantifying AKT-mTOR pathway proteins, possibly due to their low abundance and significant post-translational modification profiles.

Immunoprecipitation (IP) is commonly used upstream of MS as an enrichment tool for low-abundant protein targets. See, Gingras et al., *Nat. Rev. Mol. Cell. Biol.*, August 2007, 8 (8), 645-54; and Carr, S. A. et al., *Mol. Cell. Proteomics* March 2014, 13 (3), 907-17. The identification of appropriate antibodies for use in IP upstream of MS is important, as not all antibodies that bind to protein will be effective immunoprecipitation tools, and further, not all antibodies that are effective immunoprecipiation tools will lead to successful identification via MS.

SUMMARY OF INVENTION

The present disclosure provides reagents and methods for detecting and quantifying AKT-mTOR pathway proteins via immunoprecipitation (IP), mass spectrometry (MS), and immunoprecipitation followed by mass spectrometry (IP-MS).

In some embodiments, methods for immunoprecipitating an AKT-mTOR pathway protein (target protein) are provided, comprising contacting a biological sample with any one of the antibodies recited in Table 1. In some embodiments, the antibodies useful in the IP methods comprise the antibodies recited in Table 8. In some embodiments, the antibodies useful in the IP methods comprise the antibodies recited in Table 9. The methods may comprise washing the contacted biological sample to enrich for antibody-protein conjugates. Further methods include detecting the antibody-protein conjugates (the immunoprecipitated target protein) to determine the AKT-mTOR pathway protein in the biological sample. In some embodiments, the antibody is labelled. In some embodiments, a detection reagent is provided to the enriched antibody-protein conjugate. In some embodiments the label is biotin and the detection reagent is streptavidin.

In some embodiments the IP is single-plex. In some embodiments the IP is multi-plex. The antibodies useful in multi-plex IP may comprise the antibodies of Table 8 and Table 9.

In some embodiments a method for detecting AKT-mTOR pathway proteins via MS is provided, comprising isolating proteins from a biological sample, digesting the isolated proteins, assaying the digested proteins via mass spectrometry to determine the presence of a peptide for AKT-mTOR pathway protein(s), and determining the identity of one or more AKT-mTOR pathway protein(s) in the sample. In some embodiments, the peptide for AKT-mTOR pathway protein(s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424.

In some embodiments a method for quantifying AKT-mTOR pathway proteins via MS is provided, comprising isolating proteins from a biological sample, digesting the isolated proteins, assaying the digested proteins via mass spectrometry to determine the presence of a peptide for AKT-mTOR pathway protein(s), and determining the quantity of one or more AKT-mTOR pathway protein(s) in the sample. In some embodiments, the peptide for AKT-mTOR pathway protein(s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments a method for detecting AKT-mTOR pathway proteins via IP-MS is provided, comprising treating a biological sample with at least one antibody capable of immunoprecipitating AKT-mTOR target pathway protein(s) from a biological sample, digesting the isolated proteins, assaying the digested proteins via mass spectrometry to determine the presence of a peptide for AKT-mTOR pathway protein(s), and determining the identity of one or more AKT-mTOR pathway protein(s) in the sample. In some embodiments, the peptide for AKT-mTOR pathway protein(s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments a method for quantifying AKT-mTOR pathway proteins via IP-MS is provided, comprising treating a biological sample with at least one antibody capable of immunoprecipitating AKT-mTOR target pathway protein(s) from a biological sample, digesting the isolated proteins, assaying the digested proteins via mass spectrometry to determine the presence of a peptide for AKT-mTOR pathway protein(s), and determining the quantity of one or more AKT-mTOR pathway protein(s) in the sample. In some embodiments, the peptide for AKT-mTOR pathway protein(s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments the AKT-mTOR pathway target protein is phosphorylated.

Methods for determining the ratio of phosphorylated to non-phosphorylated AKT-mTOR pathway proteins are provided, comprising any of the above IP, MS, or MS-IP methods, wherein a further step of determining the ratio of phosphorylated to non-phosphorylated protein is provided. In some embodiments, the method is an MS-IP method comprising treating a biological sample with one or more antibodies capable of immunoprecipitating one or more phosphorylated AKT-mTOR pathway proteins, and separately treating the same biological sample with one or more antibodies capable of immunoprecipitating at least one or more of the same or different non-phosphorylated AKT-mTOR pathway proteins; digesting the immunoprecipitated AKT-mTOR pathway proteins; adding a first and a second detectably labelled internal standard peptide of known amount to the digested proteins, wherein the first internal standard peptide has the same amino acid sequence as a phosphorylated AKT-mTOR pathway peptide used to identify the phosphorylated protein, and the second internal standard peptide has the same amino acid sequence as the non-phosphorylated AKT-mTOR pathway peptide used to identify the non-phosphorylated protein; assaying the digested protein and internal standards via mass spectrometry to determine the presence and amount of phosphorylated and non-phosphorylated AKT-mTOR pathway proteins, wherein the AKT-mTOR pathway peptide comprises a peptide of SEQ ID NO: 1-SEQ ID NO: 424, and is less than 40 amino acids in length; determining the quantity of AKT-mTOR phosphorylated and non-phosphorylated pathway proteins in the sample, and determining the ratio of phosphorylated to non-phosphorylated pathway proteins. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments, the biological sample is human. In some embodiments, the biological sample is non-human. In some embodiments, the biological sample is mammalian. In some embodiments, the biological sample is from rat, mouse, guinea pig, hamster, cow, pig, horse, goat, sheep, dog, cat, or non-human primate.

In embodiments utilizing an AKT-mTOR pathway peptide, the peptide may be modified with a detectable label. The detectable label may comprise an isotope, such as a heavy isotope, such as those known to those of skill in the art, including 13C, 15N, 2H and 18O. In some embodiments, the modified/labelled peptide comprises a peptide of SEQ ID NO: 213-424. In some embodiments the peptide is less than 40 amino acids in length. In some embodiments the modified/labelled peptide consists of a peptide of SEQ ID NO: 213-424. In some embodiments the modified/labelled peptide consists of a peptide of SEQ ID NO: 213-424, wherein the peptide is further modified.

In some embodiments, the antibody for IP is selected from the group consisting of the antibodies recited in Table 1. In some embodiments, the antibody for IP is an antibody having the six CDRs of any of the antibodies of Table 1. The antibody may be capable of immunoprecipitating more than one AKT-mTOR pathway protein. In some embodiments the antibody is labelled or capable of being labelled. The label may be any label known to those of skill in the art including enzymatic and fluorescent labels, such as biotin. In some embodiments more than one antibody is used in a multi-plex IP. In some embodiments, the multi-plex IP comprises the antibodies of Table 8. In some embodiments, the multi-plex IP comprises the antibodies of Table 9.

In some embodiments, two or more antibodies are utilized to analyze one biological sample. For example, a first antibody is capable of immunoprecipitating a phosphorylated AKT-mTOR pathway protein, and a second antibody is capable of immunoprecipitating a non-phosphorylated version of the AKT-mTOR pathway protein precipitated by the first antibody. In some embodiments, a single antibody is capable of immunoprecipitating a phosphorylated and non-phosphorylated AKT-mTOR pathway protein.

In some embodiments, the immunoprecipitation comprises treating a sample with a labelled antibody capable of binding to an AKT-mTOR pathway protein to provide a labelled antibody-protein conjugate. The method may further comprise contacting the labelled antibody-protein conjugate with a capture agent capable of binding to the labelled antibody to isolate the pathway protein from the sample. The label may be biotin and the capture agent may be streptavidin.

The quantity of an AKT-mTOR pathway protein may be determined by adding an internal standard peptide of known amount to the digested protein prior to mass spectrometry. In some embodiments, the internal standard peptide has the same amino acid sequence as the AKT-mTOR pathway peptide. In some embodiments, the internal standard is detectably labeled. The method may further comprises determining the quantity of an AKT-mTOR pathway peptide by comparison to the internal standard.

In some embodiments, the internal standard peptide comprises a sequence of SEQ ID NO: 1-SEQ ID NO: 424. In some embodiments the peptide is less than 40 amino acids in length. In some embodiments, the peptide consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments, quantifying the AKT-mTOR pathway protein comprises comparing an amount of an AKT-mTOR pathway peptide in the sample to an amount of the same AKT-mTOR pathway peptide in a control sample.

Quantifying an AKT-mTOR pathway protein may comprise comparing an amount of an AKT-mTOR pathway peptide to an internal standard peptide of known amount, wherein both the peptide in the biological sample and the internal standard peptide comprise SEQ ID NO: 1-SEQ ID NO: 424, wherein the standard peptide is detectably labeled, and wherein the peptide is less than 40 amino acids long. In some embodiments, the standard peptide consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments the mass spectrometry is selected from tandem mass spectrometry and discovery mass spectrometry. The targeted mass spectrometry may be selected from multiple reaction monitoring (MRM), selected reaction monitoring (SRM), and parallel reaction monitoring (PRM), or combinations thereof.

In some embodiments the biological sample is selected from isolated human cells, plasma, serum, whole blood, CSF, urine, sputum, tissue, and tumorous tissue.

In some embodiments, the method further comprises quantifying the relative amount of AKT-mTOR pathway protein. In some embodiments, the method further comprises quantifying the absolute amount of AKT-mTOR pathway protein.

In some embodiments, the digesting comprises a protease or chemical digest. In some embodiments the digestion may be single or sequential. The protease digestion may comprise trypsin, chymotrypsin, AspN, GluC, LysC, ArgC, proteinase K, pepsin, clostripain, elastase, GluC biocarb, LysC/P, LysN promisc, protein endopeptidase, staph protease or thermolysin.

The chemical cleavage may comprise CNBr, iodosobenzoate or formic acid.

In some embodiments the digestion is a protease digest with trypsin.

In some embodiments the methods further comprise desalting after digestion and prior to mass spectrometry.

The AKT-mTOR pathway protein may be selected from AKT1 (UniProtKB-P31749), AKT2 (UniProtKB-P31751), IR (also known as INSR) (UniProtKB P06213), IGF1R (UniProtKB-P08069), IRS1 (UniProtKB-P35568), TSC2 (UniProtKB-P49815), mTOR (UniProtKB-P42345), GSK3a (UniProtKB-P49840), GSK3b (UniProtKB-P49841), GSK3a/GSK3b, p70S6K (also known as RPS6KB1) (UniProtKB-P23443), RPS6 (UniProtKB-P62753), PRAS40 (also known as AKT1S1) (UniProtKB-Q96B36), and PTEN (UniProtKB-P60484).

In some embodiments, the AKT-mTOR pathway is a protein that interacts with any of AKT1 (UniProtKB-P31749), AKT2 (UniProtKB-P31751), IR (also known as INSR) (UniProtKB P06213), IGF1R (UniProtKB-P08069), IRS1 (UniProtKB-P35568), TSC2 (UniProtKB-P49815), mTOR (UniProtKB-P42345), GSK3a (UniProtKB-P49840), GSK3b (UniProtKB-P49841), GSK3a/GSK3b, p70S6K (also known as RPS6KB1) (UniProtKB—P23443), RPS6 (UniProtKB-P62753), PRAS40 (also known as AKT1S1) (UniProtKB-Q96B36), and PTEN (UniProtKB-P60484).

In some embodiments, the AKT-mTOR pathway protein is phosphorylated.

In some embodiments, the concentration of AKT-mTOR protein that may be detected ranges from about 0.08 fmol to about 2000 fmol.

In some embodiments, the lower limit of detection is about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25 fmol. The lower limit of detection may be within the range of about 0.05-0.25 fmol.

In some embodiments the lower limit of quantification is about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.30, 0.35, 0.40, 0.45, 0.50, 0.55, 0.60, 0.65, 0.70, or 0.75 fmol. The lower limit of quantification may be within the range of about 0.05-0.75 fmol.

Kits comprising one or more antibodies capable of immunoprecipitating an AKT-mTOR pathway protein are encompassed.

Kits comprising one or more antibodies capable of immunoprecipitating an AKT-mTOR pathway protein, and reagents useful for performing mass spectrometry to detect an AKT-mTOR pathway protein are also provided.

Also encompassed are kits comprising one or more antibodies capable of immunoprecipitating an AKT-mTOR pathway target protein, and reagents useful for performing mass spectrometry to quantify an AKT-mTOR pathway protein.

The antibody to be included in the kit may be selected from any one or more of the antibodies recited in Table 1. In some embodiments the antibody is labelled or capable of being labelled. The label may be any label known to those of skill in the art including enzymatic and fluorescent labels, such as biotin. In some embodiments, the kit comprises more than one antibody. In some embodiments, the kit comprises two or more of the antibodies selected from the antibodies recited in Table 8. In some embodiments, the kit comprises two or more of the antibodies selected from the antibodies recited in Table 9. In some embodiments, the kit comprises two or more of the antibodies selected from the antibodies recited in Table 8 and two or more of the antibodies selected from the antibodies recited in Table 9. In some embodiments, the kit comprises each of the antibodies recited in Table 8, Table 9, or Tables 8 and 9.

The kits may further comprise an AKT-mTOR pathway peptide. In some embodiments, the peptide comprises a sequence of SEQ ID NO: 1-SEQ ID NO: 424. In some embodiments, the peptide is less than 40 amino acids in length. In some embodiments, the peptide consists of a sequence of SEQ ID NO: 1-SEQ ID NO: 424. The peptides of SEQ ID NO: 1-SEQ ID NO: 212 may be labelled. In some embodiments, the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments, the kit may comprise at least one peptide selected from peptides of SEQ ID NO: 213-SEQ ID NO: 424, wherein the peptide is less than or equal to 40 amino acids. In one embodiment, the kit comprises at least one peptide consisting of the peptides of SEQ ID NO: 213-SEQ ID NO: 424.

The peptides provided in the kit may be detectably labeled or capable of being modified to be detectably labeled. In some embodiments, the kit may comprise at least one peptide selected from peptides of SEQ ID NO: 1-SEQ ID NO: 212, wherein the peptide is detectably labeled or capable of being modified to be detectably labeled.

In some embodiments, the kit further comprises a protease or chemical agent capable of digesting an immunoprecipitated protein sample. The protease agent may be trypsin, chymotrypsin, AspN, GluC, LysC, LysN, ArgC, proteinase K, pepsin, clostripain, elastase, GluC biocarb, LysC/P, LysN promisc, protein endopeptidase, Staph protease or thermolysin. The chemical agent may be CNBr, iodosobenzoate or formic acid.

The kits may be utilized to detect AKT-mTOR pathway proteins, including AKT1 (UniProtKB-P31749); AKT2 (UniProtKB-P31751), IR (also known as INSR) (UniProtKB P06213), IGF1R (UniProtKB-P08069), IRS1 (UniProtKB-P35568), TSC2 (UniProtKB-P49815), mTOR (UniProtKB-P42345), GSK3a (UniProtKB-P49840), GSK3b (UniProtKB-P49841), GSK3a/GSK3b, p70S6K (also known as RPS6KB1) (UniProtKB-P23443 (KS6B1 HUMAN)), RPS6 (UniProtKB-P62753), PRAS40 (also known as AKT1S1)(UniProtKB-Q96B36), and PTEN (UniProtKB-P60484).

The AKT-mTOR protein to be detected and quantified by the kits may be phosphorylated.

Also encompassed are antibodies recited in Table 1 for use in immunoprecipitating an AKT-mTOR pathway protein. The antibody may be used in methods comprising immunoprecipitating an AKT-mTOR pathway protein prior to analyzing the protein via mass spectrometry.

AKT-mTOR pathway peptides selected from the peptides of Table 3 are encompassed. The AKT-mTOR pathway peptides may be used in methods of detecting and quantifying AKT-mTOR pathway proteins in biological samples. The AKT-mTOR pathway peptides may be used in methods comprising immunoprecipitating the AKT-mTOR pathway protein from the biological sample, and analyzing the immunoprecipitated protein via mass spectrometry.

BRIEF DESCRIPTION OF DRAWINGS

FIG. 3 shows results from an experiment to enrich for low abundant AKT-mTOR pathway proteins from A549 cells.

FIG. 4 shows detection and quantitation limits of peptides for 12 AKT-mTOR pathway proteins.

FIG. 5 shows the results of a multiplex immunoprecipitation plus nanoLC-MS/MS assay for 10 phosphorylated and 11 total AKT-mTOR pathway proteins.

FIG. 8 shows a summary of AKT-mTOR pathway proteins identified and quantified in two different cell lines, with and without immunoprecipitation enrichment, using the mass spec methods.

FIG. 9 shows technology correlation for total AKT-mTOR pathway targets.

FIG. 10 shows technology correlation for phopho-AKT-mTOR pathway targets.

FIG. 11 shows IP to Western Blot validation of AKT-mTOR pathway targets.

DESCRIPTION OF THE EMBODIMENTS

Figure 1:
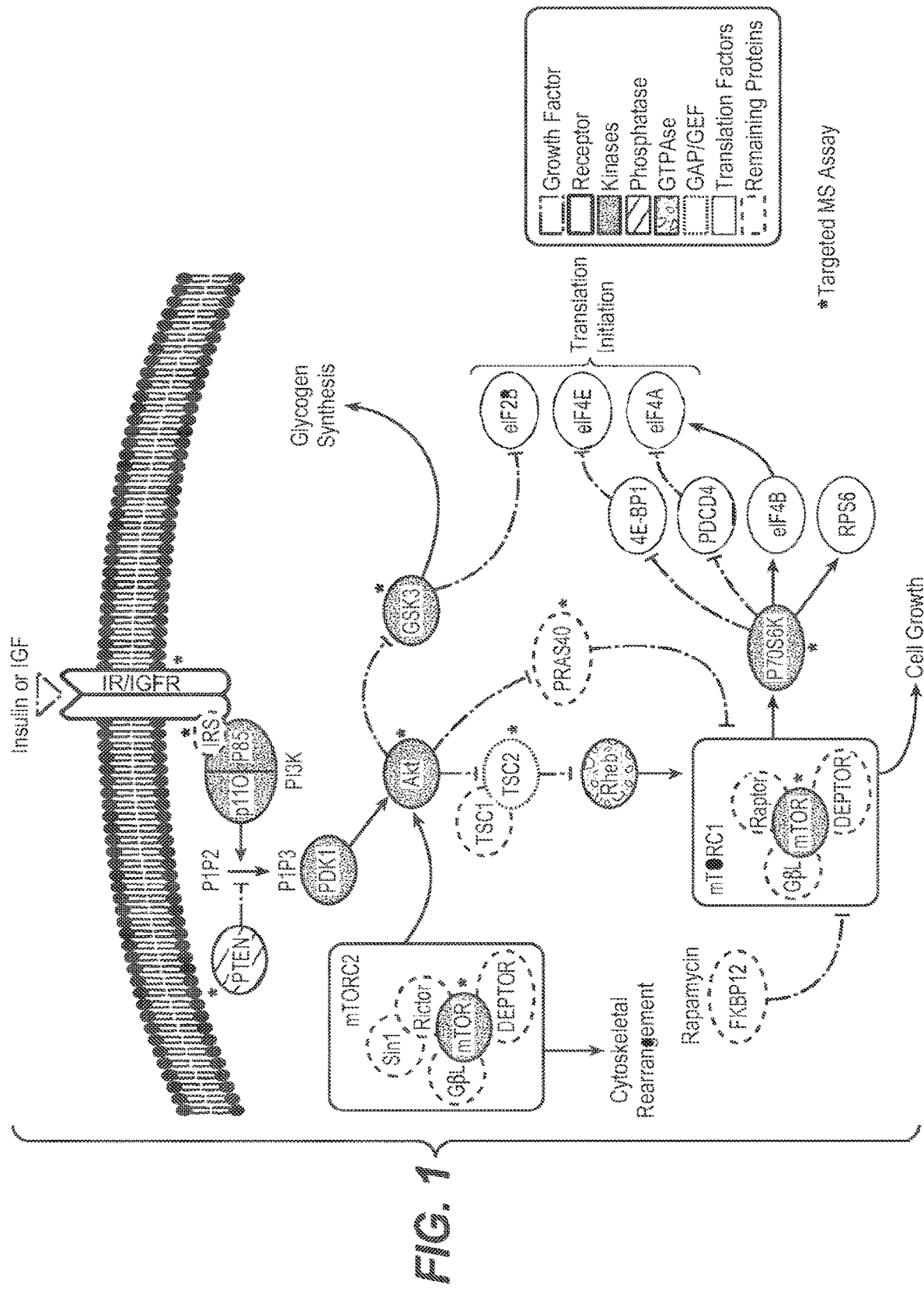
FIG. 1 shows a schematic of the AKT-mTOR pathway proteins.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

As used herein, an "AKT-mTOR pathway protein" includes, but is not limited to, AKT1 (UniProtKB-P31749), AKT2 (UniProtKB-P31751), IR (also known as INSR) (UniProtKB P06213), IGF1R (UniProtKB-P08069), IRS1 (UniProtKB-P35568), TSC2 (UniProtKB-P49815), mTOR (UniProtKB-P42345), GSK3a (UniProtKB-P49840), GSK3b (UniProtKB-P49841), GSK3a/GSK3b, p70S6K (also known as RPS6KB1) (UniProtKB-P23443), RPS6 (UniProtKB-P62753), PRAS40 (also known as AKT1S1) (UniProtKB-Q96B36), and PTEN (UniProtKB-P60484).

As used herein "protein", "peptide", and "polypeptide" are used interchangeably throughout to mean a chain of amino acids wherein each amino acid is connected to the next by a peptide bond. In some embodiments, when a chain of amino acids consists of about two to forty amino acids, the term "peptide" is used. However, the term "peptide" should not be considered limiting unless expressly indicated.

The term "antibody" is used in the broadest sense and encompasses various antibody structures, including but not limited to monoclonal antibodies, polyclonal antibodies, multispecific antibodies (such as bispecific antibodies), and antibody fragments so long as they exhibit the desired immunoprecipitating activity. As such, the term antibody includes, but is not limited to, fragments that are capable of binding to an antigen, such as Fv, single-chain Fv (scFv), Fab, Fab', di-scFv, sdAb (single domain antibody) and $(Fab')_2$ (including a chemically linked $F(ab')_2$). Papain digestion of antibodies produces two identical antigen-binding fragments, called "Fab" fragments, each with a single antigen-binding site, and a residual "Fc" fragment. Pepsin treatment yields a $F(ab')_2$ fragment that has two antigen-binding sites. The term antibody also includes, but is not limited to, chimeric antibodies, humanized antibodies, and antibodies of various species such as mouse, goat, horse, sheep, chicken, etc. Furthermore, for all antibody constructs provided herein, variants having the sequences from other organisms are also contemplated, such as CDR-grafted antibodies or chimeric antibodies. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct. The antibodies provided herein are referred to by reference to name and catalog reference. The skilled artisan, holding this name and catalog information, is capable of determining the sequence of the antibody, and therefore the disclosure encompasses any antibody having at least partial sequence of a reference antibody so long as the antibody maintains its ability to immunoprecipitate its antigen protein. In some embodiments, the antibodies comprise antibodies having the same CDRs as the antibodies provided in Table 1.

Mass spectrometry (MS) is a primary technique for analysis of proteins on the basis of their mass-to-charge ratio (m/z). MS techniques generally include ionization of compounds and optional fragmentation of the resulting ions, as well as detection and analysis of the m/z of the ions and/or fragment ions followed by calculation of corresponding ionic masses. A "mass spectrometer" generally includes an ionizer and an ion detector. "Mass spectrometry," "mass spec," "mass spectroscopy," and "MS" are used interchangeably throughout.

"Targeted mass spectrometry," also referred to herein as "targeted mass spec," "targeted MS," and "tMS" increases the speed, sensitivity, and quantitative precision of mass spec analysis. Non-targeted mass spectrometry, sometimes referred to as "data-dependent scanning," "discovery MS," and "dMS" and targeted mass spec are alike in that in each, analytes (proteins, small molecules, or peptides) are infused or eluted from a reversed phase column attached to a liquid chromatography instrument and converted to gas phase ions by electrospray ionization. Analytes are fragmented in the mass spec (a process known as tandem MS or MS/MS), and fragment and parent masses are used to establish the identity of the analyte. Discovery MS analyzes the entire content of the MS/MS fragmentation spectrum. In contrast, in targeted mass spectrometry, a reference spectrum is used to guide analysis to only a few selected fragment ions rather than the entire content.

"Multiple reaction monitoring," "MRM," "selected reaction monitoring," and "SRM" are used interchangeably throughout to refer to a type of targeted mass spectrometry that relies on a unique scanning mode accessible on triple-quadrupole (QQQ) instruments. See, e.g., Chambers et al., *Expert Rev. Proteomics*, 1-12 (2014).

"Parallel Reaction Monitoring," and "PRM" are used interchangeably herein to describe another type of targeted mass spec wherein the second mass analyzer used in SRM (quadrupole) is substituted by a high resolution orbitrap mass analyzer in PRM. Unlike SRM, which allows the measuring of one single transition at a given point in time, PRM allows parallel monitoring in one MS/MS spectrum. PRM also allows for the separation of ions with close m/z values (i.e., within a 10 ppm range), and may therefore allow for lower limits of detection and quantification (LOD or LLOD and LOQ or LLOQ).

The methods disclosed herein may be applied to any type of MS analysis. The disclosure is not limited by the specific equipment or analysis used. The use of any equipment with the intent of analyzing the m/z of a sample would be included in the definition of mass spectrometry. Non-limiting examples of MS analysis and/or equipment that may be used include electrospray ionization, ion mobility, time-of-flight, tandem, ion trap, MRM, SRM, MRM/SRM, PRM, and Orbitrap. The disclosure is neither limited by the type of ionizer or detector used in the MS analysis nor by the specific configuration of the MS. The disclosure is not limited to use with specific equipment or software. The disclosure is not limited to the equipment and software described in the Examples.

In some embodiments, methods of immunoprecipitating an AKT-mTOR pathway protein are provided, comprising contacting a biological sample with at least one antibody recited in Table 1. The immunoprecipitating method may be single-plex or multi-plex. A "single-plex" IP utilizes one antibody per assay, whereas a "multi-plex" IP utilizes more than one antibody per assay.

In some embodiments, an IP-MS method for detecting and quantifying phosphorylated and non-phosphorylated AKT-mTOR pathway proteins is provided. The methods may comprise contacting a biological sample with at least one antibody recited in Table 1, digesting the immunoprecipitated protein(s), and assaying the digested proteins via mass spectrometry. The IP and MS may be single-plex or multi-plex. A "single-plex" MS refers to monitoring a single peptide in a single MS run, whereas a "mulit-plex" MS refers to monitoring more than one target peptides in a single MS run.

Table 1 provides a listing of antibodies useful in the IP and IP-MS methods described herein. Table 2 provides a listing of antibodies that are known to bind to their antigen AKT-mTOR protein, but were found to be less useful in the IP and IP-MS methods described herein. FIG. 11 and Table 3 provide a summary of antibodies useful in IP of AKT-mTOR pathway proteins, as validated by Western Blot.

TABLE 1

List of IP to MS validated antibodies for AKT-mTOR Pathway Proteins

| Antibody Name | Company/Catalog Number |
| --- | --- |
| AKT1 Antibody | Millipore/07-416 |
| AKT (pan) Antibody | Cell Signaling Technology/2920 |
| AKT2 Antibody | Cell Signaling Technology/3063 |
| phospho AKT2 (pSer474) Antibody | Thermo Fisher Scientific/PA5-35676 |
| AKT1 Antibody | Cell Signaling Technology/2967 |
| phospho AKT (pSer473) Antibody | Thermo Fisher Scientific/700392 |
| phospho AKT (pSer473) Antibody | Cell Signaling Technology/4060 |
| Anti-phospho-IGF-1R (Tyr1161/Tyr1165/Tyr1166) Antibody | Millipore/ABE332 |
| Phospho-IGF1 Rec pTyr1158 + 1162 + 1163 Antibody | Thermo Fisher Scientific/PA1-26725 |
| Phospho-IGF1R pTyr1161 Antibody | Thermo Fisher Scientific/PA5-35769 |
| Phospho-IGF-I Receptor β (Tyr1131)/Insulin Receptor β (Tyr1146) Antibody | Cell Signaling Technology/3021 |
| IGF-I Receptor β Antibody | Cell Signaling Technology/9750 |
| IGF-I Receptor β Antibody | Cell Signaling Technology/3027 |
| Insulin Receptor β Antibody | Cell Signaling Technology/3020 |
| INSR/Insulin Receptor Antibody | Thermo Fisher Scientific/MA1-10865 |
| Anti-α-Insulin Receptor Antibody, β subunit Antibody | Millipore/07-724 |
| INSR/Insulin Receptor alpha Antibody | Thermo Fisher Scientific/MA5-13759 |
| Anti-Insulin Receptor (phospho Y972) Antibody | abcam/ab5678 |
| IRS-1 Antibody | Cell Signaling Technology/2382 |
| IRS-1 Antibody | Cell Signaling Technology/3407 |
| IRS-1 Antibody | Millipore/06-248 |
| IRS-1 Antibody | Millipore/05-784R |
| IRS-1 Antibody | Millipore/05-1085 |
| IRS1 (pSer312) polyclonal Antibody | Abnova/PAB12627 |
| Anti-phospho-IRS1 (Ser307 mouse/Ser312 human) Antibody | Millipore/05-1087 |
| Phospho-IRS-1 (pSer1101) Antibody | Cell Signaling Technology/2385 |
| mTOR Antibody | Cell Signaling Technology/2972 |
| mTOR Antibody | Millipore/07-1415 |
| mTOR Antibody | abcam/ab2732 |
| mTOR Antibody | abcam/ab25880 |
| mTOR Antibody | Thermo Fisher Scientific/PA1-518 |
| Phospho-mTOR (pSer2448) Antibody | Thermo Fisher Scientific/PA5-35652 |
| Phospho-mTOR (pSer2448) Antibody | Cell Signaling Technology/5536 |
| Phospho-mTOR (pSer2448) Antibody | Abgent/AP50437 |
| S6K Antibody | Thermo Fisher Scientific/PA5-12726 |
| S6K Antibody | Thermo Fisher Scientific/PA5-12723 |
| S6K1 Antibody | Thermo Fisher Scientific/PA1-31167 |
| Anti-S6K1 Antibody | abcam/ab9366 |
| S6K Antibody | Thermo Fisher Scientific/PA5-27853 |
| Phospho-p70 S6 Kinase (pThr389/pThr412) Antibody | Thermo Fisher Scientific/PA5-35701 |
| Phospho-p70 S6 Kinase (pThr389) Antibody | Thermo Fisher Scientific/701064 |
| Phospho-p70 S6 Kinase (pThr421/pSer424) Antibody | Cell Signaling Technology/9204 |
| Phospho-p70 S6 Kinase pThr389 Antibody | Thermo Fisher Scientific/MA5-15202 |
| Phospho-GSK-3α/β (pSer21/pSer9) Antibody | Cell Signaling Technology/9327 |
| GSK3a Antibody | Cell Signaling Technology/4337 |
| GSK3a Antibody | Cell Signaling Technology/4818 |
| Phospho-GSK-3α (Ser21) Antibody | Cell Signaling Technology/8452 |
| Phospho-GSK-3α (Ser21) Antibody | Cell Signaling Technology/9316 |
| Phospho-GSK-3α/β (pSer21/pSer9) Antibody | Cell Signaling Technology/8566 |
| GSK3β Antibody | Thermo Fisher Scientific/MA5-15109 |
| GSK3β Antibody | Thermo Fisher Scientific/PA5-29251 |
| GSK3β Antibody | Thermo Fisher Scientific/PA5-29265 |
| GSK3β Antibody | Cell Signaling Technology/12456 |
| Phospho-GSK-3β (pSer9) Antibody | Cell Signaling Technology/5558 |
| Phospho-Tuberin/TSC2 pSer939 Antibody | Thermo Fisher Scientific/710395 |
| Phospho-TSC2 pSer939 Antibody | Thermo Fisher Scientific/PA5-12845 |
| Phospho-TSC2 pSer939 Antibody | abcam/ab59269 |
| Phospho-TSC2 pSer939 Antibody | abcam/ab52962 |
| Anti-TSC2 Antibody | abcam/ab52936 |
| Anti-TSC2 Antibody | Cell Signaling Technology/4308 |
| Anti-TSC2 Antibody | Thermo Fisher Scientific/PA5-20132 |
| Anti-TSC2 Antibody | Cell Signaling Technology/3990 |
| Anti-TSC2 Antibody | Thermo Fisher Scientific/MA5-15004 |
| S6 Ribosomal Protein Antibody | Thermo Fisher Scientific/701374 |
| S6 Ribosomal Protein Antibody | Thermo Fisher Scientific/710405 |
| S6 Ribosomal Protein Antibody | Thermo Fisher Scientific/PA5-11818 |
| Phospho-S6 Ribosomal Protein pSer235 + 236 Antibody | Thermo Fisher Scientific/701363 |
| RPS6 Antibody | Thermo Fisher Scientific/PA5-26041 |
| Anti-PRAS40 Antibody | abcam/ab72321 |
| Anti-PRAS40 Antibody | Thermo Fisher Scientific/PA5-35143 |
| Anti-PRAS40 Antibody | R&D System/MAB6408 (R&D) |
| Anti-PRAS40 Antibody | Cell Signaling Technology/2691 |
| Phospho-PRAS40 (pThr246) Antibody | Cell Signaling Technology/2997 |
| Phospho-PRAS40 (pThr246) Antibody | Cell Signaling Technology/13175 |
| Phospho-PRAS40 (pThr246) Antibody | R&D System/MAB6890 |

TABLE 1-continued

List of IP to MS validated antibodies for AKT-mTOR Pathway Proteins

| Antibody Name | Company/Catalog Number |
| --- | --- |
| Phospho-PTEN (pSer380) Antibody | Cell Signaling Technology/9551 |
| PTEN Antibody | Cell Signaling Technology/9188 |
| AKT pan Antibody | Thermo Fisher Scientific/44-609G |
| mTOR Antibody | Thermo Fisher Scientific/PA1-188 |
| IRS1 Antibody | Thermo Fisher Scientific/710009 |
| IRS1 Antibody | Thermo Fisher Scientific/AHO1322 |
| IGFIR Antibody | Thermo Fisher Scientific/39-6700 |
| TSC2 Antibody | Thermo Fisher Scientific/AHO1422 |
| TSC2 Antibody | Thermo Fisher Scientific/730014 |
| PTEN Antibody | Thermo Fisher Scientific/51-2400 |

TABLE 2

List of IP to MS less successful antibodies for AKT-mTOR Pathway Proteins

| Antibody Name | Company/Catalog Number |
| --- | --- |
| Phospho-Akt (Ser473) Antibody | Cell Signaling Technology/4051 |
| AKT1 Antibody | Thermo Fisher Scientific/PA5-23780 |
| AKT2 Antibody | Thermo Fisher Scientific/MA1-034 |
| Phospho-AKT1 pSer473 Antibody | Thermo Fisher Scientific/MA1-20325 |
| Phospho-IGF-I Receptor β (Tyr1316) Antibody | Cell Signaling Technology/6113 |
| Phospho-IGF-I Receptor β (Tyr1131)/Insulin Receptor β (Tyr 1146) Antibody | Cell Signaling Technology/3021 |
| IGF-I Receptor β Antibody | Cell Signaling Technology/3018 |
| IGF-IR/IGF1 Receptor alpha Antibody | Thermo Fisher Scientific/MA5-13817 |
| IGF-IR/IGF1 Receptor alpha Antibody | Thermo Fisher Scientific/MA5-13799 |
| Anti-IGF1 Receptor (phospho Y1162 + Y1163) Antibody | Abcam/ab5680 |
| IGF-IR/IGF1 Receptor alpha Antibody | Thermo Fisher Scientific/MA5-13802 |
| IGF-IR/IGF1 Receptor Antibody | Thermo Fisher Scientific/MAl-10853 |
| Phospho-IGF-IR beta pTyr1135/1136 + IR beta pTyr1150/1151 Antibody | Thermo Fisher Scientific/MA5-15148 |
| Phospho-IGF-IR + IR pTyr1162 + 1163 Antibody | Thermo Fisher Scientific/700393 |
| Phospho-IGF-IR pTyr1135 + 1136 Antibody | Thermo Fisher Scientific/701067 |
| Phospho-IGF1 Rec. pTyr1162 + 1163 Antibody | Thermo Fisher Scientific/PA1-26724 |
| Anti-phospho-IR/IGFIR (Tyr1158) Antibody | Millipore/07-839 |
| Insulin Receptor (β-Subunit) | Thermo Fisher Scientific/MS-635-P1 |
| Anti-Insulin Receptor (pTyr1162/1163) Antibody | Millipore/407707 |
| Anti-phospho-IR/IGF1R (Tyr1158/Tyr1162/Tyr1163) Antibody | Millipore/07-841 |
| Phospho-IRS-1 pSer312 Antibody | Thermo Fisher Scientific/PA5-35670 |
| Phospho-IRS-1 (Ser307) Antibody | Cell Signaling Technology/2381 |
| Phospho-IRS-1 (Ser1101) Antibody | Cell Signaling Technology/2385 |
| Phospho-IRS-1 (Ser318) Antibody | Cell Signaling Technology/5610 |
| p70 S6 Kinase Antibody | Cell Signaling Technology/9202 |
| Phospho-p70 S6 Kinase (Thr389) Antibody | Thermo Fisher Scientific/MA5-15117 |
| Phospho-S6 Ribosomal Protein pSer235 + 236 Antibody | Thermo Fisher Scientific/710394 |
| Phospho-p70 S6 Kinase pThr389 Antibody | Thermo Fisher Scientific/710095 |
| p70 S6 Kinase Antibody | Thermo Fisher Scientific/701261 |
| Phospho-p70 S6 Kinase pThr389 Antibody | Thermo Fisher Scientific/PA1-526 |
| GSK-3 alpha Antibody | Novus Biologicals/NB110-87048 |
| GSK3 alpha Antibody | Thermo Fisher Scientific/PA5-15400 |
| GSK3 alpha Antibody | Thermo Fisher Scientific/PA1-25969 |
| GSK3 beta Antibody | Thermo Fisher Scientific/MA1-7621 |
| GSK3B Antibody | Thermo Fisher Scientific/PA1-27893 |
| GSK-3 beta Antibody | Novus Biologicals/NBP1-04292 |
| GSK3B Antibody | Thermo Fisher Scientific/MA5-15597 |
| Anti-Tuberin (phospho S1254) Antibody | Abcam/ab133454 |
| TSC2 (phospho S939) Antibody | Abnova/PAB16959 |
| Phospho-Tuberin/TSC2 (Thr1462) Antibody | Cell Signaling Technology/3611 |
| S6 Ribosomal Protein Antibody | Thermo Fisher Scientific/MA5-15123 |
| Phospho-RSK3 pThr356 + Ser360 Antibody | Thermo Fisher Scientific/PA5-17554 |
| Non-Phospho PTEN (Ser380 + Thr382 + Thr383) Antibody | Thermo Fisher Scientific/PA5-17153 |
| PTEN Antibody | ProSci/3515 |
| PTEN Antibody | ProSci/3517 |

The immunoprecipitated AKT-mTOR pathway proteins may be reduced and alkylated prior to fragmentation (e.g., digestion). Samples that have been reduced and alkylated may comprises modifications, such as to cysteine residues (e.g., CAM). Where an AKT-mTOR peptide of SEQ ID NO: 1-424 shows modification resulting from, for example, reduction/alkylation, the non-modified peptide is also encompassed. For example, in each instance where an AKT-mTOR pathway peptide of SEQ ID NO: 1-424 is referred to, also encompassed are unmodified peptides of SEQ ID NO: 1-424.

The samples may optionally be desalted prior to analysis by mass spectrometry. Both enzymatic and chemical digestion is encompassed. Enzymatic digestion includes, but is not limited to, digestion with a protease such as, for example, trypsin, chymotrypsin, AspN, GluC, LysC, LysN, ArgC, proteinase K, pepsin, Clostripain, Elastase, GluC biocarb, LysC/P, LysN Promisc, Protein Endopeptidase, Staph Protease or thermolysin. Chemical digestion includes use of, for example, CNBr, iodosobenzoate and formic acid.

In some embodiments, after fragmentation (e.g., digestion), peptide samples are analyzed by mass spectrometry (MS), and the resulting spectra are compared with theoretical spectra from known proteins to determine the peptides and proteins in a sample. For AKT-mTOR pathway proteins, discovery MS is cumbersome and time consuming and is not a viable clinical method. Therefore, the inventors have identified novel peptides that associate with AKT-mTOR pathway proteins for use in the IP-MS methods of the disclosure. Use of these peptides in targeted MS, and IP-targeted MS methods allows quantitation of even low abundant AKT-mTOR proteins. Moreover, use of these peptides in targeted MS, and in IP-targeted MS methods, allows quantitation of phosphorylated AKT-mTOR proteins.

Theoretically, peptides useful in MS to detect and quantify AKT-mTOR pathway proteins can be designed by use of computer software and the like. However, many of these potential peptide sequences are unsuitable or ineffective for use in MS-based assays, including SRM/MRM and PRM. Because it was not possible to predict the most suitable peptides for MS analysis, it was necessary to experimentally identify modified and unmodified peptides to develop as clinical reagents. To complicate the analysis, it was discovered that certain peptides useful when assaying typical samples were not predictive when assaying samples that had undergone immunoprecipitation.

Typically, targeted MS is performed by quantifying specific unique peptides of the protein. In some embodiments, known amounts of isotope-labeled (e.g., heavy isotope-labeled) versions of these targeted peptides can be used as internal standards for absolute quantitation. In some instances, proteins of interest are not detectable even after identifying unique peptide standards. The combination of specific antibodies with specific target peptides has allowed the inventors to improve the sensitivity of detection of AKT-mTOR pathway proteins by MS, and has allowed for lower levels of detection and lower levels of quantification than ever previously seen. See, e.g., FIG. 4.

In some embodiments, the AKT-mTOR pathway peptides provided in the kits, and useful in the described methods, are listed in Table 3. SEQ ID Nos: 1-212 are native peptide sequences useful in identifying the AKT-mTOR pathway proteins recited in the "Target ID" column. Certain peptide sequences are phosphorylated at certain residues as shown in parentheses "(PO3H2)" following the modified residue.

Certain peptides are modified at cysteine residues as shown by "(CAM)" following the modified residue. The "CAM" post-translational modification is well known to those of skill in the art to mean carbamidomethylation, resulting from alkylation of the protein/peptide. The peptides may be as shown in Table 3, or may be non-modified version of these peptides lacking carbamidomethylation.

TABLE 3

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| AKT1_1 | NDGTFIGYK | 1 | NDGTFIGY[K(13C6; 15N2)] | 213 |
| AKT1_2 | SLLSGLLK | 2 | SLLSGLL[K(13C6; 15N2)] | 214 |
| AKT1_3 | EAPLNNFSVAQCQLMK | 3 | EAPLNNFSVAQCQLM[K(13C6; 15N2)] | 215 |
| AKT1_4 | RPHFPQF[S(PO3H2)]YSASGTA | 4 | RPHFPQF[S(PO3H2)]YSASGT[A(13C3; 15N)] | 216 |
| AKT1_5 | RPHFPQFSYSASGTA | 5 | RPHFPQFSYSASGTA[A(13C3; 15N)] | 217 |
| AKT2_1 | SDGSFIGYK | 6 | SDGSFIGY[K(13C6; 15N2)] | 218 |
| AKT2_2 | SLLAGLLK | 7 | SLLAGLL[K(13C6; 15N2)] | 219 |
| AKT2_3 | THFPQF[SP03H2)]YSASIRE | 8 | THFPQF[SPO3H2)]YSASI[R(13C6; 15N4)]E | 220 |
| AKT2_4 | THFPQFSYSASIRE | 9 | THFPQFSYSASI[R(13C6; 15N4)]E | 221 |
| AKT3_1 | LVPPFKPQVTSETDTR | 10 | LVPPFKPQVTSETDT[R(13C6; 15N4)] | 222 |
| AKT3_2 | SLLSGLLIK | 11 | SLLSGLLI[K(13C6; 15N2)] | 223 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| IR_1 | [C(CAM)]SVAAYVSAR | 12 | [C(CAM)]SVAAYVSA[R(13C6; 15N4)] | 224 |
| IR_2 | CSVAAYVSAR | 13 | CSVAAYVSA[R(13C6; 15N4)] | 225 |
| IR_3 | GLKPWTQYAIFVK | 14 | GLKPWTQYAIFV[K(13C6; 15N2)] | 226 |
| IR_4 | IELQA[C(CAM)]NQDTPEER | 15 | IELQA[C(CAM)]NQDTPEE[R(13C6; 15N4)] | 227 |
| IR_5 | TIDSVTSAQELR | 16 | TIDSVTSAQEL[R(13C6; 15N4)] | 228 |
| IR_6 | TNCPATVINGQFVER | 17 | TNCPATVINGQFVE[R(13C6; 15N4)] | 229 |
| IR_7 | TN[C(CAM)]PATVINGQFVER | 18 | TN[C(CAM)]PATVINGQFVE[R(13C6; 15N4)] | 230 |
| IR_8 | TNGDQASCENELLK | 19 | TNGDQASCENELL[K(13C6; 15N2)] | 231 |
| IR_9 | TNGDQAS[C(CAM)]ENELLK | 20 | TNGDQAS[C(CAM)]ENELL[K(13C6; 15N2)] | 232 |
| IR_10 | VCHLLEGEK | 21 | VCHLLEGE[K(13C6; 15N2)] | 233 |
| IR_11 | V[C(CAM)]HLLEGEK | 22 | V[C(CAM)]HLLEGE[K(13C6; 15N2)] | 234 |
| IR_12 | TVNESASLR | 23 | TVNESASL[R(13C6; 15N4)] | 235 |
| IR_13 | DIIKGEAETR | 24 | DIIKGEAET[R(13C6; 15N4)] | 236 |
| IR/IGF1R_1 | DIYETDYYR | 25 | DIYETDYY[R(13C6; 15N4)] | 237 |
| IR/IGF1R_2 | DIYETDYYRK | 26 | DIYETDYYR[K(13C6; 15N2)] | 238 |
| IR/IGF1R_3 | DI[Y(PO3H2)]ETDYYR | 27 | DI[Y(PO3H2)]ETDYY[R(13C6; 15N4)] | 239 |
| IR/IGF1R_4 | DIYETD[Y(PO3H2)]YR | 28 | DIYETD[Y(PO3H2)]Y[R(13C6; 15N4)] | 240 |
| IR/IGF1R_5 | DIYETDY[Y(PO3H2)]R | 29 | DIYETDY[Y(PO3H2)][R(13C6; 15N4)] | 241 |
| IR/IGF1R_6 | DIYETD[Y(PO3H2)][Y(PO3H2)]R | 30 | DIYETD[Y(PO3H2)][Y(PO3H2)][R(13C6; 15N4)] | 242 |
| IR/IGF1R_7 | DI[Y(PO3H2)]ETD[Y(PO3H2)]YR | 31 | DI[Y(PO3H2)]ETD[Y(PO3H2)]Y[R(13C6; 15N4)] | 243 |
| IR/IGF1R_8 | DI[Y(PO3H2)]ETDY[Y(PO3H2)]R | 32 | DI[Y(PO3H2)]ETDY[Y(PO3H2)][R(13C6; 15N4)] | 244 |
| IR/IGF1R_9 | DI[Y(PO3H2)]ETD[Y(PO3H2)][Y(PO3H2)]R | 33 | DI[Y(PO3H2)]ETD[Y(PO3H2)][Y(PO3H2)][R(13C6; 15N4)] | 245 |
| IGF1R_1 | AENGPGPGVLVLR | 34 | AENGPGPGVLVL[R(13C6; 15N4)] | 246 |
| IGF1R_2 | HYYYAGV[C(CAM)]VPA[C(CAM)]PPNTYR | 35 | HYYYAGV[C(CAM)]VPA[C(CAM)]PPNTY[R(13C6; 15N4)] | 247 |
| IGF1R_3 | HYYYAGVCVPAC P PNTYR | 36 | HYYYAGVCVPACPPNTY[R(13C6; 15N4)] | 248 |
| IGF1R_4 | LG[C(CAM)]SASNFVFAR | 37 | LG[C(CAM)]SASNFVFA[R(13C6; 15N4)] | 249 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| IGF1R_5 | LGCSASNFVAR | 38 | LGCSASNFVA[R(13C6; 15N4)] | 250 |
| IGF1R_6 | SLRPEMENNPVLAPPSLSK | 39 | SLRPEMENNPVLAPPSLS[K(13C6; 15N2)] | 251 |
| IGF1R_7 | TTINNEYNYR | 40 | TTINNEYNY[R(13C6; 15N4)] | 252 |
| IGF1R_8 | VAGLESLGDLFPNLTVIR | 41 | VAGLESLGDLFPNLTVI[R(13C6; 15N4)] | 253 |
| IGF1R_9 | YADGTIDIEEVTENPK | 42 | YADGTIDIEEVTENP[K(13C6; 15N2)] | 254 |
| IGF1R_10 | YGSQVEDQRE[C(CAM)]VSR | 43 | YGSQVEDQRE[C(CAM)]VS[R(13C6; 15N4)] | 255 |
| IGF1R_11 | YGSQVEDQRECVSR | 44 | YGSQVEDQRECVS[R(13C6; 15N4)] | 256 |
| IGF1R_12 | IDIHSCNHEAEK | 45 | IDIHSCNHEAE[K(13C6; 15N2)] | 257 |
| IGF1R_13 | GVVKDEPETR | 46 | GVVKDEPET[R(13C6; 15N4)] | 258 |
| IRS1_1 | ASSDGEGTMSRPASVDGSPVSPSTNR | 47 | ASSDGEGTMSRPASVDGSPVSPSTN[R(13C6; 15N4)] | 259 |
| IRS1_2 | [C(CAM)]GHSENFFFIEVGR | 48 | [C(CAM)]GHSENFFFIEVG[R(13C6; 15N4)] | 260 |
| IRS1_3 | CGHSENFFFIEVGR | 49 | CGHSENFFFIEVG[R(13C6; 15N4)] | 261 |
| IRS1_4 | [C(CAM)]TPGTGLGTSPALAGDEAASAADLDNR | 50 | [C(CAM)]TPGTGLGTSPALAGDEAASAADLDN[R(13C6; 15N4)] | 262 |
| IRS1_5 | CTPGTGLGTS PALAGDEAAS AADLDNR | 51 | CTPGTGLGTS PALAGDEAASAADLDN[R(13C6; 15N4)] | 263 |
| IRS1_6 | HHLNNPPPSQVGLTR | 52 | HHLNNPPPSQVGLT[R(13C6; 15N4)] | 264 |
| IRS1_7 | HSSETFSSTPSATR | 53 | HSSETFSSTPSAT[R(13C6; 15N4)] | 265 |
| IRS1_8 | KGSGDYMPMSPK | 54 | KGSGDYMPMSP[K(13C6; 15N2)] | 266 |
| IRS1_9 | L[C(CAM)]GAAGGLENGLNYIDLDLVK | 55 | L[C(CAM)]GAAGGLENGLNYIDLDLV[K(13C6; 15N2)] | 267 |
| IRS1_10 | LCGAAGGLENGLNYIDLDLVK | 56 | LCGAAGGLENGLNYIDLDLV[K(13C6; 15N2)] | 268 |
| IRS1_11 | SVSAPQQIINPIR | 57 | SVSAPQQIINPI[R(13C6; 15N4)] | 269 |
| IRS1_12 | TESITATSPASMVGGKPGSFR | 58 | TESITATSPASMVGGKPGSF[R(13C6; 15N4)] | 270 |
| IRS1_13 | TGIAAEEVSLPR | 59 | TGIAAEEVSLP[R(13C6; 15N4)] | 271 |
| IRS1_14 | SYPEEGLEMHPLER | 60 | SYPEEGLEMHPLE[R(13C6; 15N4)] | 272 |
| IRS1_15 | THSAGTSPTITHQK | 61 | THSAGTSPTITHQ[K(13C6; 15N2)] | 273 |
| IRS1_16 | AS[S(PO3H2)]DGEGTMSRPASVDGSPVSPSTNR | 62 | AS[S(PO3H2)]DGEGTMSRPASVDGSPVSPSTN[R(13C6; 15N4)] | 274 |
| IRS1_17 | HS[S(PO3H2)]ETFSSTPSATR | 63 | HS[S(PO3H2)]ETFSSTPSAT[R(13C6; 15N4)] | 275 |
| IRS1_18 | KGSGDYMPM[S(PO3H2)]PK | 64 | KGSGDYMPM[S(PO3H2)]P[K(13C6; 15N2)] | 276 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| IRS1_19 | KGSGDY[M(O)]P[M(O)][S(PO3H2)]PK | 65 | KGSGDY[M(O)]P[M(O)][S(PO3H2)]P[K(13C6; 15N2)] | 277 |
| IRS1_20 | L[C(CAM)]GAAGGLENGLN[Y(PO3H2)]IDLDLVK | 66 | L[C(CAM)]GAAGGLENGLN[Y(PO3H2)]IDLDLV[K(13C6; 15N2)] | 278 |
| IRS1_21 | LCGAAGGLENGLN[Y(PO3H2)]IDLDLVK | 67 | LCGAAGGLENGL[Y(PO3H2)]IDLDLV[K(13C6; 15N2)] | 279 |
| IRS1_22 | TESITAT[S(PO3H2)]PASMVGGKPGSFR | 68 | TESITAT[S(PO3H2)]PASMVGGKPGSF[R(13C6; 15N4)] | 280 |
| IRS1_23 | TESITAT[S(PO3H2)]PAS[M(O)]VGGKPGSFR | 69 | TESITAT[S(PO3H2)]PAS[M(O)]VGGKPGSF[R(13C6; 15N4)] | 281 |
| TSC2_1 | APAQTPAEPTPGYEVGQR | 70 | APAQTPAEPTPGYEVGQ[R(13C6; 15N4)] | 282 |
| TSC2_2 | DSFRARSTSLNERPK | 71 | DSFRARSTSLNERP[K(13C6; 15N2)] | 283 |
| TSC2_3 | EAPAKLE SQAGQQVSR | 72 | EAPAKLESQAGQQVS[R(13C6; 15N4)] | 284 |
| TSC2_4 | GYTISDSAPSR | 73 | GYTISDSAPS[R(13C6; 15N4)] | 285 |
| TSC2_5 | LISSVEDFTEFV | 74 | LISSVEDFTEF[V(13C5; 15N)] | 286 |
| TSC2_6 | LVTVTTSVGTGTR | 75 | LVTVTTSVGTGT[R(13C6; 15N4)] | 287 |
| TSC2_7 | SQSGTLDGESAAWSASGEDSR | 76 | SQSGTLDGESAAWSASGEDS[R(13C6; 15N4)] | 288 |
| TSC2_8 | SVQLLDQIPSYDTHK | 77 | SVQLLDQIPSYDTH[K(13C6; 15N2)] | 289 |
| TSC2_9 | VGALDVPASQFLGSATSPGPR | 78 | VGALDVPASQFLGSATSPGP[R(13C6; 15N4)] | 290 |
| TSC2_10 | VVSSEGGRPSVDLSFQPSQPLSK | 79 | VVSSEGGRPSVDLSFQPSQPLS[K(13C6; 15N2)] | 291 |
| TSC2_11 | YTEFLTGLGR | 80 | YTEFLTGLG[R(13C6; 15N4)] | 292 |
| TSC2_12 | YVFSNFTAVPK | 81 | YVFSNFTAVP[K(13C6; 15N2)] | 293 |
| TSC2_13 | SNPTDIYPSK | 82 | SNPTDIYPS[K(13C6; 15N2)] | 294 |
| TSC2_14 | FNSCYLDEYIAR | 83 | FNSCYLDEYIA[R(13C6; 15N4)] | 295 |
| TSC2_15 | GQPEGPLPSSSPR | 84 | GQPEGPLPSSSP[R(13C6; 15N4)] | 296 |
| TSC2_16 | SLLGLDSGELQSGPESSSSPGVHVR | 85 | SLLGLDSGELQSGPESSSSPGVHV[R(13C6; 15N4)] | 297 |
| TSC2_17 | DSFRARST[S(PO3H2)]LNERPK | 86 | DSFRARST[S(PO3H2)]LNERP[K(13C6; 15N2)] | 298 |
| TSC2_18 | GY[T(PO3H2)]ISDSAPSR | 87 | GY[T(PO3H2)]ISDSAPS[R(13C6; 15N4)] | 299 |
| TSC2_19 | LI[S(PO3H2)]SVEDFTEFV | 88 | LI[S(PO3H2)]SVEDFTEF[V(13C5; 15N)] | 300 |
| TSC2_20 | LIS[S(PO3H2)]VEDFTEFV | 89 | LIS[S(PO3H2)]VEDFTEF[V(13C5; 15N)] | 301 |
| TSC2_21 | LI[S(PO3H2)][S(PO3H2)]VEDFTEFV | 90 | LI[S(PO3H2)][S(PO3H2)]VEDFTEF[V(13C5; 15N)] | 302 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| TSC2_22 | ST[S(PO3H2)]LNERPK | 91 | ST[S(PO3H2)]LNERP[K(13C6; 15N2)] | 303 |
| TSC2_23 | STSLNERPK | 92 | STSLNERP[K(13C6; 15N2)] | 304 |
| mTOR_1 | AVLALHQDLFSLAQQ[C(CAM)]IDK | 93 | AVLALHQDLFSLAQQ[C(CAM)]ID[K(13C6; 15N2)] | 305 |
| mTOR_2 | AVLALHQDLFSLAQQCIDK | 94 | AVLALHQDLFSLAQQCID[K(13C6; 15N2)] | 306 |
| mTOR_3 | DLELAVPGTYDPNQPHR | 95 | DLELAVPGTYDPNQPII[R(13C6; 15N4)] | 307 |
| mTOR_4 | GNNLQDTLR | 96 | GNNLQDTL[R(13C6; 15N4)] | 308 |
| mTOR_5 | GPTPAILESLISINNK | 97 | GPTPAILESLISINN[K(13C6; 15N2)] | 309 |
| mTOR_6 | GYTLADEEEDPLIYQHR | 98 | GYTLADEEEDPLIYQH[R(13C6; 15N4)] | 310 |
| mTOR_7 | IHGALLILNELVR | 99 | IHGALLILNELV[R(13C6; 15N4)] | 311 |
| mTOR_8 | IQSIAPSLQVITSK | 100 | IQSIAPSLQVITS[K(13C6; 15N2)] | 312 |
| mTOR_9 | LFDAPEAPLPSR | 101 | LFDAPEAPLPS[R(13C6; 15N4)] | 313 |
| mTOR_10 | LGEWQLNLQGINESTIPK | 102 | LGEWQLNLQGINESTIP[K(13C6; 15N2)] | 314 |
| mTOR_11 | LIHQLLTDIGR | 103 | LIHQLLTDIG[R(13C6; 15N4)] | 315 |
| mTOR_12 | SPSSEVWFDR | 104 | SPSSEVWFD[R(13C6; 15N4)] | 316 |
| mTOR_13 | TDSYSAGQSVEILDGVELGEPAHK | 105 | TDSYSAGQSVEILDGVELGEPAH[K(13C6; 15N2)] | 317 |
| mTOR_14 | TLVLLLGVDPSR | 106 | TLVLLLGVDPS[R(13C6; 15N4)] | 318 |
| mTOR_15 | VEVFEHAVNNTAGDDLAK | 107 | VEVFEHAVNNTAGDDLA[K(13C6; 15N2)] | 319 |
| mTOR_16 | VLGLLGALDPYK | 108 | VLGLLGALDPY[K(13C6; 15N2)] | 320 |
| mTOR_17 | WTLVNDETQAK | 109 | WTLVNDETQA[K(13C6; 15N2)] | 321 |
| mTOR_18 | ETSFNQAYGR | 110 | ETSFNQAYG[R(13C6; 15N4)] | 322 |
| mTOR_19 | TLDQSPELR | 111 | TLDQSPEL[R(13C6; 15N4)] | 323 |
| mTOR_20 | TD[S(PO3H2)]YSAGQSVEILDGVELGEPAHK | 112 | TD[S(PO3H2)]YSAGQSVEILDGVELGEPAH[K(13C6; 15N2)] | 324 |
| mTOR_21 | [T(PO3H2)]DSYSAGQSVEILDGVELGEPAHK | 113 | [T(PO3H2)]DSYSAGQSVEILDGVELGEPAH[K(13C6; 15N2)] | 325 |
| mTOR_22 | [T(PO3H2)]D[S(PO3H2)]YSAGQSVEILDGVELGEPAHK | 114 | [T(PO3H2)]D[S(PO3H2)]YSAGQSVEILDGVELGEPAH[K(13C6; 15N2)] | 326 |
| GSK3a_1 | DIKPQNLLVDPDTAVLK | 115 | DIKPQNLLVDPDTAVL[K(13C6; 15N2)] | 327 |
| GSK3a_2 | LSPLEA[C(CAM)]AHSFFDELR | 116 | LSPLEA[C(CAM)]AHSFFDEL[R(13C6; 15N4)] | 328 |
| GSK3a_3 | LSPLEACAHSFFDELR | 117 | LSPLEACAHSFFDEL[R(13C6; 15N4)] | 329 |
| GSK3a_4 | SLAYIHSQGV[C(CAM)]HR | 118 | SLAYIHSQGV[C(CAM)]H[R(13C6; 15N4)] | 330 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| GSK3a_5 | SLAYIHSQGVCHR | 119 | SLAYIHSQGVCH[R(13C6; 15N4)] | 331 |
| GSK3a_6 | SQEVAYTDIK | 120 | SQEVAYTDI[K(13C6; 15N2)] | 332 |
| GSK3a_7 | TPPEAIAL[C(CAM)]SSLLEYTPSSR | 121 | TPPEAIAL[C(CAM)]SSLLEYTPSS[R(13C6; 15N4)] | 333 |
| GSK3a_8 | TPPEAIALCSSLLEYTPSSR | 122 | TPPEAIALCSSLLEYTPSS[R(13C6; 15N4)] | 334 |
| GSK3a_9 | TSSFAEPGGGGGGGGGPGGSASGPGGTGGGK | 123 | TSSFAEPGGGGGGGGGPGGSASGPGGTGGG[K(13C6; 15N2)] | 335 |
| GSK3a_10 | VTTVVATLGQGPER | 124 | VTTVVATLGQGPE[R(13C6; 15N4)] | 336 |
| GSK3a_11 | DSGKVTTVVATLGQGPER | 125 | DSGKVTTVVATLGQGPE[R(13C6; 15N4)] | 337 |
| GSK3a_12 | YFFYSSGEK | 126 | YFFYSSGE[K(13C6; 15N2)] | 338 |
| GSK3a_13 | TS[S(PO3H2)]FAEPGGGGGGGGGGPGGSASGPGGTGGGK | 127 | TS[S(PO3H2)]FAEPGGGGGGGGGPGGSASGPGGTGGG[K(13C6; 15N2)] | 339 |
| GSK3b_1 | DEVYLNLVLDYVPETVYR | 128 | DEVYLNLVLDYVPETVY[R(13C6; 15N4)] | 340 |
| GSK3b_2 | DIKPQNLLLDPDTAVLK | 129 | DIKPQNLLLDPDTAVL[K(13C6; 15N2)] | 341 |
| GSK3b_3 | DTPALFNFTTQELSSNPPLATILIPPHAR | 130 | DTPALFNFTTQELSSNPPLATILIPPHA[R(13C6; 15N4)] | 342 |
| GSK3b_4 | L[C(CAM)]DSGELVAIK | 131 | L[C(CAM)]DSGELVAI[K(13C6; 15N2)] | 343 |
| GSK3b_5 | LCDSGELVAIK | 132 | LCDSGELVAI[K(13C6; 15N2)] | 344 |
| GSK3b_6 | LLEYTPTAR | 133 | LLEYTPTA[R(13C6; 15N4)] | 345 |
| GSK3b_7 | SLAYIHSFGI[C(CAM)]HR | 134 | SLAYIHSFGI[C(CAM)]H[R(13C6; 15N4)] | 346 |
| GSK3b_8 | SLAYIHSFGICHR | 135 | SLAYIHSFGICH[R(13C6; 15N4)] | 347 |
| GSK3b_9 | TTSFAES[C(CAM)]KPVQQPSAFGSMK | 136 | TTSFAES[C(CAM)]KPVQQPSAFGSM[K(13C6; 15N2)] | 348 |
| GSK3b_10 | TTSFAESCKPVQQPSAFGSMK | 137 | TTSFAESCKPVQQPSAFGSM[K(13C6; 15N2)] | 349 |
| GSK3b_11 | TTSFAES[C(CAM)]KPVQQPSAFGS[M(O)]K | 138 | TTSFAES[C(CAM)]KPVQQPSAFGS[M(O)][K(13C6; 15N2)] | 350 |
| GSK3b_12 | TTSFAESCKPVQQPSAFGS[M(O)]K | 139 | TTSFAESCKPVQQPSAFGS[M(O)][K(13C6; 15N2)] | 351 |
| GSK3b_13 | VTTVVATPGQGPDRPQEVSYTDTK | 140 | VTTVVATPGQGPDRPQEVSYTDTK | 352 |
| GSK3b_14 | KLDHCNIVR | 141 | KLDHCNIV[R(13C6; 15N4)] | 353 |
| GSK3b_15 | DSSGTGHFTSGVR | 142 | DSSGTGHFTSGV[R(13C6; 15N4)] | 354 |
| GSK3b_16 | TT[S(PO3H2)]FAES[C(CAM)]KPVQQPSAFGS[M(O)]K | 143 | TT[S(PO3H2)]FAES[C(CAM)]KPVQQPSAFGS[M(O)][K(13C6; 15N2)] | 355 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| GSK3b_17 | TT[S(PO3H2)]FAESCKPVQQPSAFGS[M(O)]K | 144 | TT[S(PO3H2)]FAESCKPVQQPSAFGS[M(O)]K[(13C6; 15N2)] | 356 |
| GSK3b_18 | TT[S(PO3H2)]FAES[C(CAM)]KPVQQPSAFGSMK | 145 | TT[S(PO3H2)]FAES[C(CAM)]KPVQQPSAFGSM[K(13C6; 15N2)] | 357 |
| GSK3b_19 | TT[S(PO3H2)]FAESCKPVQQPSAFGSMK | 146 | TT[S(PO3H2)]FAESCKPVQQPSAFGSM[K(13C6; 15N2)] | 358 |
| GSK3a/GSK3b_1 | GEPNVSYI[C(CAM)]SR | 147 | GEPNVSYI[C(CAM)]S[R(13C6; 15N4)] | 359 |
| GSK3a/GSK3b_2 | GEPNVSYICSR | 148 | GEPNVSYICS[R(13C6; 15N4)] | 360 |
| GSK3a/GSK3b_3 | GEPNVS[Y(PO3H2)]I[C(CAM)]SR | 149 | GEPNVS[Y(PO3H2)]I[C(CAM)]S[R(13C6; 15N4)] | 361 |
| GSK3a/GSK3b_4 | GEPNVS[Y(PO3H2)]ICSR | 150 | GEPNVS[Y(PO3H2)]ICS[R(13C6; 15N4)] | 362 |
| GSK3a/GSK3b_5 | GEPNV[S(PO3H2)]YI[C(CAM)]SR | 151 | GEPNV[S(PO3H2)]YI[C(CAM)]S[R(13C6; 15N4)] | 363 |
| GSK3a/GSK3b_6 | GEPNV[S(PO3H2)]YICSR | 152 | GEPNV[S(PO3H2)]YICS[R(13C6; 15N4)] | 364 |
| GSK3a/GSK3b_7 | GEPNV[S(PO3H2)][Y(PO3H2)]I[C(CAM)]SR | 153 | GEPNV[S(PO3H2)][Y(PO3H2)]I[C(CAM)]S[R(13C6; 15N4)] | 365 |
| GSK3a/GSK3b_8 | GEPNV[S(PO3H2)][Y(PO3H2)]ICSR | 154 | GEPNV[S(PO3H2)][Y(PO3H2)]ICS[R(13C6; 15N4)] | 366 |
| GSK3a/GSK3b_9 | TPPEAIALCSR | 155 | TPPEAIALCS[R(13C6; 15N4)] | 367 |
| GSK3a/GSK3b_10 | TPPEAIAL[C(CAM)]SR | 156 | TPPEAIAL[C(CAM)]S[R(13C6; 15N4)] | 368 |
| p70S6K_1 | DGFYPAPDFR | 157 | DGFYPAPDF[R(13C6; 15N4)] | 369 |
| p70S6K_2 | DLKPENIMLNHQGHVK | 158 | DLKPENIMLNHQGHV[K(13C6; 15N2)] | 370 |
| p70S6K_3 | FEISETSVNR | 159 | FEISETSVN[R(13C6; 15N4)] | 371 |
| p70S6K_4 | FSPGDFWGR | 160 | FSPGDFWG[R(13C6; 15N4)] | 372 |
| p70S6K_5 | HINWEELLAR | 161 | HINWEELLA[R(13C6; 15N4)] | 373 |
| p70S6K_6 | HPFIVDLIYAFQTGGK | 162 | HPFIVDLIYAFQTGG[K(13C6; 15N2)] | 374 |
| p70S6K_7 | IRPE[C(CAM)]FELLR | 163 | IRPE[C(CAM)]FELL[R(13C6; 15N4)] | 375 |
| p70S6K_8 | IRPECFELLR | 164 | IRPECFELL[R(13C6; 15N4)] | 376 |
| p70S6K_9 | LGAGPGDAGEVQAHPFFR | 165 | LGAGPGDAGEVQAHPFF[R(13C6; 15N4)] | 377 |
| p70S6K_10 | LNLPPYLTQEAR | 166 | LNLPPYLTQEA[R(13C6; 15N4)] | 378 |
| p70S6K_11 | LTDFGL[C(CAM)]K | 167 | LTDFGL[C(CAM)][K(13C6; 15N2)] | 379 |
| p70S6K_12 | LTDFGLCK | 168 | LTDFGLC[K(13C6; 15N2)] | 380 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| p70S6K_13 | QTPVD SPDDSTLSE SANQVF LGFTYVAPSVLESVK | 169 | QTPVDSPDDSTLSESANQVFLGFTYVAPSVLESV[K(13C6; 15N2)] | 381 |
| p70S6K_14 | TPVSPVK | 170 | TPVSPV[K(13C6; 15N2)] | 382 |
| p70S6K_15 | TPVS PVKF S PGD FWGR | 171 | TPVSPVKFSPGDFWG[R(13C6; 15N4)] | 383 |
| p70S6K_16 | QTPVD SPDDSTLSE SANQVF LGF[T(PO3H2)]YVAPSVLESVK | 172 | QTPVDSPDDSTLSESANQVFLGF[T(PO3H2)]YVAPSVLESV[K(13C6; 15N2)] | 384 |
| p70S6K_17 | QTPVD[S(PO3H2)]PDDSTLSESANQVFLGFTYVAPSVLESVK | 173 | QTPVD[S(PO3H2)]PDDSTLSESANQVFLGFTYVAPSVLESV[K(13C6; 15N2)] | 385 |
| p70S6K_18 | QTPVD[S(PO3H2)]PDDSTLSESANQVFLGF[T(PO3H2)]YVAPSVLESVK | 174 | QTPVD[S(PO3H2)]PDDSTLSESANQVFLGF[T(PO3H2)]YVAPSVLESV[K(13C6; 15N2)] | 386 |
| p70S6K_19 | [T(PO3H2)]PVSPVK | 175 | [T(PO3H2)]PVSPV[K(13C6; 15N2)] | 387 |
| p70S6K_20 | TPV[S(PO3H2)]PVK | 176 | TPV[S(PO3H2)]PV[K(13C6; 15N2)] | 388 |
| p70S6K_21 | [T(PO3H2)]PV[S(PO3H2)]PVK | 177 | [T(PO3H2)]PV[S(PO3H2)]PV[K(13C6; 15N2)] | 389 |
| p70S6K_22 | TPV[S(PO3H2)]PVKFSPGDFWGR | 178 | TPV[S(PO3H2)]PVKFSPGDFWG[R(13C6; 15N4)] | 390 |
| p70S6K_23 | [T(PO3H2)]PV[S(PO3H2)]PVKFSPGDFWGR | 179 | [T(PO3H2)]PV[S(PO3H2)]PVKFSPGDFWG[R(13C6; 15N4)] | 391 |
| p70S6K_24 | [T(PO3H2)]PVSPVKFSPGDFWGR | 180 | [T(PO3H2)]PVSPVKFSPGDFWG[R(13C6; 15N4)] | 392 |
| RPS6_1 | DIPGLTDTTVPR | 181 | DIPGLTDTTVP[R(13C6; 15N4)] | 393 |
| RPS6_2 | GHS[C(CAM)]YRPR | 182 | GHS[C(CAM)]YRP[R(13C6; 15N4)] | 394 |
| RPS6_3 | GHSCYRPR | 183 | GHSCYRP[R(13C6; 15N4)] | 395 |
| RPS6_4 | LNISFPATG[C(CAM)]QK | 184 | LNISFPATG[C(CAM)]Q[K(13C6; 15N2)] | 396 |
| RPS6_5 | LNISFPATGCQK | 185 | LNISFPATGCQ[K(13C6; 15N2)] | 397 |
| RPS6_6 | MATEVAADALGEEWK | 186 | MATEVAADALGEEW[K(13C6; 15N2)] | 398 |
| RPS6_7 | RRRLSSLRASTSK | 187 | RRRLSSLRASTS[K(13C6; 15N2)] | 399 |
| RPS6_8 | RRRL[S(PO3H2)]SLRASTSK | 188 | RRRL[S(PO3H2)]SLRASTS[K(13C6; 15N2)] | 400 |
| RPS6_9 | RRRLS[S(PO3H2)]LRASTSK | 189 | RRRLS[S(PO3H2)]LRASTS[K(13C6; 15N2)] | 401 |
| RPS6_10 | RRRL[S(PO3H2)][S(PO3H2)]LRASTSK | 190 | RRRL[S(PO3H2)][S(PO3H2)]LRASTS[K(13C6; 15N2)] | 402 |
| PRAS40_1 | AATAARPPAPPPAPQPPSPTPSPPRPTLAR | 191 | AATAARPPAPPPAPQPPSPTPSPPRPTLA[R(13C6; 15N4)] | 403 |
| PRAS40_2 | [C(CAM)]LHDIALAHR | 192 | [C(CAM)]LHDIALAH[R(13C6; 15N4)] | 404 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| PRAS40_3 | CLHDIALAHR | 193 | CLHDIALAH[R(13C6; 15N4)] | 405 |
| PRAS40_4 | EAEDTQVFGDLPRPR | 194 | EAEDTQVFGDLPRP[R(13C6; 15N4)] | 406 |
| PRAS40_5 | SLPVSVPVWGFK | 195 | SLPVSVPVWGF[K(13C6; 15N2)] | 407 |
| PRAS40_6 | SSDEENGPPSSPDLDR | 196 | SSDEENGPPSSPDLD[R(13C6; 15N4)] | 408 |
| PRAS40_7 | TEARSSDEENGPPSSPDLDR | 197 | TEARSSDEENGPPSSPDLD[R(13C6; 15N4)] | 409 |
| PRAS40_8 | TGTELVLLTAAPPPPPRPGP[C(CAM)]AYAAHGR | 198 | TGTELVLLTAAPPPPPRPGP[C(CAM)]AYAAHG[R(13C6; 15N4)] | 410 |
| PRAS40_9 | TGTELVLLTAAPPPPPRPGPCAYAAHGR | 199 | TGTELVLLTAAPPPPPRPGPCAYAAHG[R(13C6; 15N4)] | 411 |
| PRAS40_10 | LNTSDFQK | 200 | LNTSDFQ[K(13C6; 15N2)] | 412 |
| PRAS40_11 | EAEDTQVFGDLPRPRLNTSDFQK | 201 | EAEDTQVFGDLPRPRLNTSDFQ[K(13C6; 15N2)] | 413 |
| PRAS40_12 | GALAEAAR | 202 | GALAETIA[R(13C6; 15N4)] | 414 |
| PRAS40_13 | ASGRPEELWEAVVGAAER | 203 | ASGRPEELWEAVVGAAE[R(13C6; 15N4)] | 415 |
| PRAS40_14 | LN[T(PO3H2)]SDFQK | 204 | LN[T(PO3H2)]SDFQ[K(13C6; 15N2)] | 416 |
| PRAS40_15 | EAEDTQVFGDLPRPRLN[T(PO3H2)]SDFQK | 205 | EAEDTQVFGDLPRPRLN[T(PO3H2)]SDFQ[K(13C6; 15N2)] | 417 |
| PTEN_1 | YSDTTDSDPENEPFDEDQHTQITK | 206 | YSDTTDSDPENEPFDEDQHTQIT[K(13C6; 15N2)] | 418 |
| PTEN_2 | YSDTTDSDPENEPFDEDQHTQITKV | 207 | YSDTTDSDPENEPFDEDQHTQIT[K(13C6; 15N2)]V | 419 |
| PTEN_3 | NNIDDWR | 208 | NNIDDW[R(13C6; 15N4)] | 420 |
| PTEN_4 | AQEALDFYGEVR | 209 | AQEALDFYGEV[R(13C6; 15N4)] | 421 |
| PTEN_5 | IYSSNSGPTR | 210 | IYSSNSGPT[R(13C6; 15N4)] | 422 |
| PTEN_6 | Y[S(PO3H2)]DTTDSDPENEPFDEDQHTQITK | 211 | Y[S(PO3H2)]DTTDSDPENEPFDEDQHTQIT[K(13C6; 15N2)] | 423 |
| PTEN_7 | Y[S(PO3H2)]DTTDSDPENEPFDEDQHTQITKV | 212 | Y[S(PO3H2)]DTTDSDPENEPFDEDQHTQIT[K(13C6; 15N2)]V | 424 |

In some embodiments, the peptides reagents are recited in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204). In some embodiments, the peptides of Table 5 are useful in multi-plex MS methods.

In some embodiments, protein samples are denatured or solubilized before fragmentation.

In some embodiments, the fragmentation protocol uses chemical cleavage. In some embodiments, the chemical cleavage uses CNBr. In some embodiments, the fragmentation protocol is done using an enzyme. In some embodiments, the fragmentation protocol uses MS-grade commercially available proteases. Examples of proteases that may be used to digest samples include trypsin, endoproteinase GluC, endoproteinase ArgC, pepsin, chymotrypsin, LysN protease, LysC protease, GluC protease, AspN protease, proteinase K, and thermolysin. In some embodiments, a mixture of different proteases are used and the individual results are combined together after the digestion and analysis. In some embodiments, the digestion is incomplete in order to see larger, overlapping peptides. In some embodiments, the antibody digestion is performed with IdeS, IdeZ, pepsin, or papain to generate large antibody domains for "middle-down" protein characterization. In some embodiments, the fragmentation protocol uses trypsin that is modified. In some embodiments, a protein:protease ratio (w/w) of 10:1, 20:1, 25:1, 50:1, 66:1, or 100:1 may be used. In some embodiments, the trypsin used is at a concentration of about 100 ng/ml-1 mg/ml, or about 100 ng/ml-500 µg/ml, or about 100 ng/ml-100 µg/ml, or about 1 µg/ml-1 mg/ml, or about 1 µg/ml-500 µg/ml, or about 1 µg/ml-100 m/ml, or about 10 m/mg-1 mg/ml, or about 10 µg/mg-500 µg/ml, or about 10 µg/mg-100 µg/ml. In some embodiments, the digestion step is for 10 minutes to 48 hours, or 30 minutes to 48 hours, or 30 minutes to 24 hours, or 30 minutes to 16 hours, or 1 hour to 48 hours, or 1 hour to 24 hours, or 1 hour to 16 hours, or 1 to 8 hours, or 1 to 6 hours, or 1 to 4 hours. In some embodiments, the digestion step is incubated at a temperature between 20° C. and 45° C., or between 20° C. and 40° C., or between 22° C. and 40° C., or between 25° C. and 37° C. In some embodiments, the digestion step is incubated at 37° C. or 30° C. In some embodiments, a step is included to end the digestion step. The step to end the digestion protocol may be addition of a stop solution or a step of spinning or pelleting of a sample. In some embodiments, the digestion is followed by guanidation.

In some embodiments, the fragmentation protocol includes use of protein gels. In some embodiments, the fragmentation protocol comprises in-gel digestion. An exemplary commercially available kit for performing in-gel digestion is the In-Gel Tryptic Digestion Kit (Thermo Fisher Cat #89871).

In some embodiments, the fragmentation protocol is carried out in solution. An exemplary commercially available kit for performing in-solution digestion is the In-Solution Tryptic Digestion and Guanidiation Kit (Thermo Fisher Cat #89895).

In some embodiments, the fragmentation protocol uses beads. In some embodiments, the fragmentation protocol comprises on-bead digestion. In some embodiments, agarose beads or Protein G beads are used. In some embodiments, magnetic beads are used.

In some embodiments, protein samples are separated using liquid chromatography before MS analysis. In some embodiments, fragmented samples are separated using liquid chromatography before MS analysis.

The IP and IP-MS methods described herein are capable of detecting phosphorylated AKT-mTOR pathway proteins, including those described in Table 4.

TABLE 4

List of Total and Phosphorylated AKT-mTOR Pathway Target Proteins

| Target ID No. | Target Name (Total) | Phosphorylation Site |
|---|---|---|
| 1 | AKT1 | pSer473 |
| 2 | PTEN | pSer380 |
| 3 | IRS1 | pSer312 |
| 4 | IR | pTyr1162/1163 |
| 5 | IGF-1R | pTyr1135/1136 |
| 6 | GSK3a | pSer21 |
| 7 | GSK3b | pSer9 |
| 8 | RPS6 | pSer235/236 |
| 9 | PRAS40 | pThr246 |
| 10 | mTOR | pSer2448 |
| 11 | p70S6K (S6K1) | pThr389 |
| 12 | TSC2 | pSer939 |

In some embodiments, the AKT-mTOR pathway peptides used in the MS methods described herein have limits of detection considered useful in clinical and research methods. See, e.g, Table 5. In some embodiments, the AKT-mTOR pathway peptides used in the MS and IP-MS methods comprise or consist of the peptides described in Table 5. In some embodiments, the peptides of Table 5 are detectably labelled. The peptides of SEQ ID NO: 163 may lack the "CAM" modification shown on the fifth amino acid.

TABLE 5

Lower Limit of Quantitation of Peptides for AKT-mTOR Pathway Proteins

| Target ID | Native Peptide Sequence | SEQ ID NO: | Lower limit of Quantitation (fmol) |
|---|---|---|---|
| mTOR_6 | GYTLADEEEDPLIYQHR | 98 | 0.69 |
| mTOR_4 | GNNLQDTLR | 96 | 0.08 |
| p70S6K_1 | DGFYPAPDFR | 157 | 0.23 |
| p70S6K_7 | IRPE[C(CAM)]FELLR | 163 | 6.17 |
| IGF1R_7 | TTINNEYNYR | 40 | 0.08 |
| IGF1R_9 | YADGTIDIEEVTENPK | 42 | 0.69 |
| IGF1R_4 | LG[C(CAM)]SASNFVFAR | 37 | 2.06 |
| IR/IGF1R_1 | DIYETDYYR | 25 | 0.69 |
| TSC2_4 | GYTISDSAPSR | 73 | 0.69 |
| TSC2_11 | YTEFLTGLGR | 80 | 0.69 |
| IRS1_6 | HHLNNPPPSQVGLTR | 52 | 0.69 |
| IRS1_11 | SVSAPQQIINPIR | 57 | 0.08 |
| IRS1_13 | TGIAAEEVSLPR | 59 | 0.23 |
| PTEN_3 | NNIDDVVR | 208 | 0.08 |
| PTEN_4 | AQEALDFYGEVR | 209 | 0.08 |

TABLE 5-continued

Lower Limit of Quantitation of Peptides for AKT-mTOR Pathway Proteins

| Target ID | Native Peptide Sequence | SEQ ID NO: | Lower limit of Quantitation (fmol) |
|---|---|---|---|
| IR_5 | TIDSVTSAQELR | 16 | 0.23 |
| IR_12 | TVNESASLR | 23 | 0.08 |
| GSK3a_10 | VTTVVATLGQGPER | 124 | 0.23 |
| GSK3a_6 | SQEVAYTDIK | 120 | 0.69 |
| PRAS40_5 | SLPVSVPVWGFK | 195 | 6.17 |
| PRAS40_10 | LNTSDFQK | 200 | 0.69 |
| GSK3b_2 | DIKPQNLLLDPDTAVLK | 129 | 6.17 |
| GSK3b_6 | LLEYTPTAR | 133 | 0.23 |
| AKT1_1 | NDGTFIGYK | 1 | 0.23 |
| AKT2_1 | SDGSFIGYK | 6 | 0.69 |
| IR/IGF1R_3 | DI[Y(PO3H2)]ETDYYR | 27 | 0.69 |
| TSC2_22 | ST[S(PO3H2)]LNERPK | 91 | 0.23 |
| PRAS40_14 | LN[T(PO3H2)]SDFQK | 204 | 0.69 |

In some embodiments, methods for detecting phosphorylated AKT-mTOR pathway proteins are encompassed. In some embodiments, IP, MS, and IP-MS methods to detect phosphorylated AKT-mTOR pathway proteins are conducted separately from methods to detect total (non-phosphorylated) AKT-mTOR pathway proteins. In some embodiments, the IP and IP-MS methods to detect phosphorylated AKT-mTOR pathway proteins utilize the antibodies of Table 9. In some embodiments, the IP and IP-MS methods to detect non-phosphorylated AKT-mTOR pathway proteins utilize the antibodies of Table 8. In some embodiments, the IP-MS methods to detect phosphorylated AKT-mTOR pathway proteins utilize the antibodies of Table 9 and the peptides of Table 5. In some embodiments, the IP-MS methods to detect non-phosphorylated AKT-mTOR pathway proteins utilize the antibodies of Table 8 and the peptides of Table 5.

TABLE 8

List of non-phosho-antibodies for multi-plex IP, single-plex IP (+/−MS).

| Target | Vendor | IP Antibody |
|---|---|---|
| AKT | MILLIPORE | 07-416 |
| IGF1R | CELL SIGNALING TECHNOLOGY | 3027 |
| IR | MILLIPORE | 07-724 |
| IRS1 | CELL SIGNALING TECHNOLOGY | 2382 |
| mTOR | THERMO FISHER SCIENTIFIC | PA1-518 |
| P70S6K | ABGENT | AP3289g |
| GSK3a | CELL SIGNALING TECHNOLOGY | 4337 |
| GSK3b | THERMO FISHER SCIENTIFIC | MA5-15109 |
| TSC2 | THERMO FISHER SCIENTIFIC | MA5-15004 |
| PRAS40 | THERMO FISHER SCIENTIFIC | PA5-35143 |
| PTEN | CELL SIGNALING TECHNOLOGY | 9188 |

TABLE 9

List of antibodies for multi-plex IP, single-plex IP (+/−MS).

| Target | Vendor | IP Antibody |
|---|---|---|
| phosphoAKT | CELL SIGNALING TECHNOLOGY | 4060 |
| phosphoIGF1R | THERMO FISHER SCIENTIFIC | PA5-35769 |
| phosphoIR | N/A | N/A |
| phosphoIRS1 | MILLIPORE | 05-1087 |
| phosphomTOR | CELL SIGNALING TECHNOLOGY | 5536 |
| phosphoP70S6K | CELL SIGNALING TECHNOLOGY | 9204 |
| phosphoGSK3a | CELL SIGNALING TECHNOLOGY | 9327 |
| phosphoGSK3b | CELL SIGNALING TECHNOLOGY | 5558 |
| phosphoTSC2 | THERMO FISHER SCIENTIFIC | PA5-12845 |
| phosphoPRAS40 | CELL SIGNALING TECHNOLOGY | 2997 |
| phosphoPTEN | CELL SIGNALING TECHNOLOGY | 9551 |

EXAMPLES

The following examples are provided to illustrate certain disclosed embodiments and are not to be construed as limiting the scope of this disclosure in any way.

Example 1—Immunoprecipitation of AKT-mTOR Pathway Proteins and Discovery-MS

Figure 2:
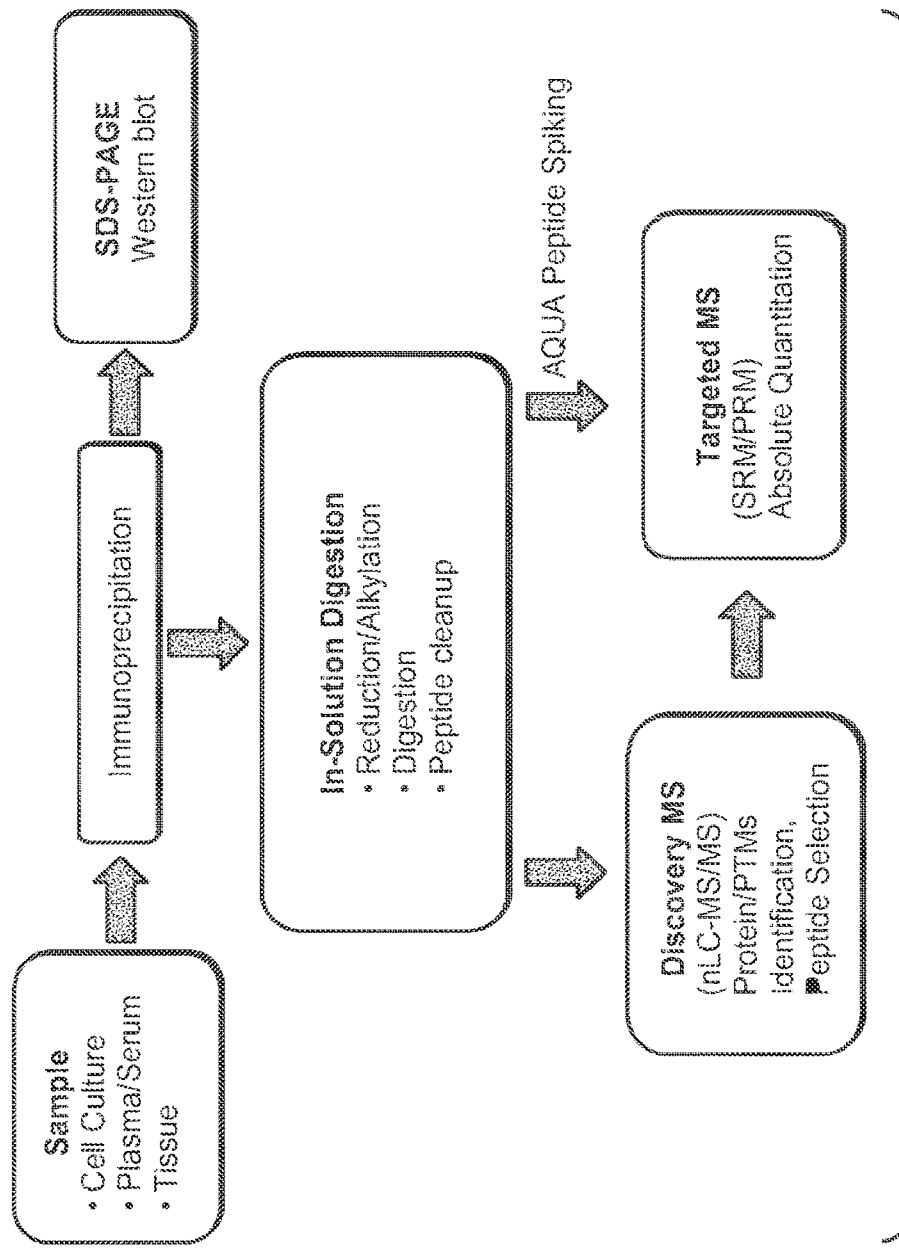
FIG. 2 shows one representative workflow for an immunoprecipitation-enriched mass spectrometry assay to identify AKT-mTOR pathway proteins.

AKT-mTOR pathway proteins play central roles in diseases including cancer. The identification of AKT-mTOR pathway proteins, while desired as a means for monitoring disease progression, and as a tool for scientific research, has been limited in part because of the low abundance of AKT-mTOR pathway proteins, and in part due to a lack of validated methods and reagents. Phosphorylated AKT-mTOR pathway proteins are particularly important to identify and quantify as a measure of protein activation status, and as markers for disease progression. As shown in FIG. 2, methods and reagents for detecting AKT-mTOR pathway proteins, including phosphorylated proteins, and their protein interactions, were designed and tested. Multiplex immunoprecipitation (IP) to MS (mIP-MS) was assessed for the ability to measure total and phosphorylated AKT-mTOR pathway targets. mIP-MS methods were also compared to existing singleplex immunoassay (Western Blot (WB) and ELISA) and multiplex Luminex assays.

Cell Culture

For all assays, HCT116 (ATCC product #CCL-247), MCF7, (ATCC product #HTB-22) and A549 (ATCC product #CCL-185) cells were grown in Hamm's F-12K media, McCoy's 5 A Media, and MEM Media, respectively, with 10% FBS/1×PenStrep to approximately 70-80% confluency. Cells were starved in 0.1% charcoal stripped FBS for 24 hours before stimulation with 100 ng/ml of IGF (CST product #8917SF) for 15 minutes.

Controls

Western Blot (WB), ELISA, and Luminex Assays were used as controls to compare to the IP-MS method described herein. The reagents and methods for Western Blots are summarized in Table 6.

TABLE 6

List of IP to Western Blot validated antibodies for AKT-mTOR Pathway Targets

| Target | WB Antibody | Vendor | Dilution | Gel | Notes |
| --- | --- | --- | --- | --- | --- |
| AKT | 4691 | CELL SIGNALING TECHNOLOGY | (1:1000) | Tris Glycine | |
| phosphoAKT | 4051 | CELL SIGNALING TECHNOLOGY | (1:1000) | Tris Glycine | |
| IGF1R | 3027 | CELL SIGNALING TECHNOLOGY | (1:1000) | Tris Acetate | |
| phosphoIGF1R | Biotinylated AP50303 | Abgent | (1:10,000) | Tris Acetate | SA HRP Secondary |
| IR | 3020 | CELL SIGNALING TECHNOLOGY | (1:1000) | Tris Acetate | |
| phosphoIR | 07-841 | Millipore | (1:1000) | Tris Acetate | |
| IRS1 | 2382 | CELL SIGNALING TECHNOLOGY | (1:1000) | Tris Acetate | |
| phosphoIRS1 | Biotinylated 05-1087 | Millipore | (1:1000) | Tris Acetate | SA HRP Secondary |
| mTOR | 2983 | CELL SIGNALING TECHNOLOGY | (1:1000) | Tris Acetate | |
| phosphomTOR | 5536 | CELL SIGNALING TECHNOLOGY | (1:1000) | Tris Acetate | |
| P70S6K | AP3289g | Abgent | (1:1000) | Tris Glycine | |
| phosphoP70S6K | 9204 | CELL SIGNALING TECHNOLOGY | (1:1000) | Tris Glycine | |
| GSK3a | 4337 | CELL SIGNALING TECHNOLOGY | (1:1000) | Tris Glycine | Clean Blot |
| phosphoGSK3a | 8506 | CELL SIGNALING TECHNOLOGY | (1:1000) | Tris Glycine | Clean Blot |
| GSK3b | 12456 | CELL SIGNALING TECHNOLOGY | (1:1000) | Tris Glycine | Clean Blot |
| phosphoGSK3b | 5558 | CELL SIGNALING TECHNOLOGY | (1:1000) | Tris Glycine | Clean Blot |
| TSC2 | 4308 | CELL SIGNALING TECHNOLOGY | (1:1000) | Tris Acetate | |
| phosphoTSC2 | ab52962 | Abcam | (1:10,000) | Tris Acetate | |
| PRAS40 | AP14275b | Abgent | (1:1000) | Tris Glycine | |
| phosphoPRAS40 | 2997 | CELL SIGNALING TECHNOLOGY | (1:1000) | Tris Glycine | |
| PTEN | 9188 | CELL SIGNALING TECHNOLOGY | (1:1000) | Tris Glycine | Clean Blot |
| phosphoPTEN | 9551 | CELL SIGNALING TECHNOLOGY | (1:1000) | Tris Glycine | Clean Blot |

Secondary Antibodies: Goat Anti-Rabbit Ab (Thermo Fisher Scientific, PN: 32460), Goat Anti-Mouse Ab (Thermo Fisher Scientific, PN: 32430), Pierce High Sensitivity Streptavidin-HRP (Thermo Fisher Scientific, PN: 21130)
SDS-PAGE Gels: NuPAGE 3-8% Tris-Acetate Gel (Thermo Fisher Scientific, PN: EA03752BOX), Novex 4-20% Tris-Glycine Midi Gel (Thermo Fisher Scientific, PN: WT4201BX10)
Clean Blot: Thermo Fisher Scientific, PN: 21232

Reagents for ELISA kits are shown in Table 7.

TABLE 7

ELISA kits for 11 total and 10 phosphorylated AKT-mTOR Pathway Targets

| Target | Vendor | Product# | Lot# |
| --- | --- | --- | --- |
| Total GSK3B | Cell Signaling Technology | 7265 | 0004 |
| Phospho GSK3β | Cell Signaling Technology | 7311 | 0004 |
| Phospho GSK3β | Life Technologies | KHO0461 | 16404995B |
| Total IRS1 | Cell Signaling Technology | 7328 | 0011 |
| Phospho IRS1 | N/A | N/A | N/A |
| Total PTEN | Cell Signaling Technology | 7882 | 0005 |
| Phospho PTEN | Cell Signaling Technology | 7285 | 0006 |
| Total PRAS40 | Cell Signaling Technology | 7331 | 0003 |
| Phospho PRAS40 | Cell Signaling Technology | 7327 | 0004 |
| Total Insulin Receptor | Cell Signaling Technology | 7069 | 0006; 0004 |
| Phospho Insulin Receptor | Cell Signaling Technology | 7258 | 0016; 0015 |
| Total IGF1R | R&D Systems | DYC305-2 | 1324480 |
| Total IGF1R | Abcam | ab100546 | GR212867-1 |
| PhosphoIGF1R | Cell Signaling Technology | 7302 | 0015 |
| Total GSK3α | R&D Systems | DYC2157-2 | 1299193 |
| Phospho GSK3α | R&D Systems | DYC4125-2 | 1300987 |
| Total TSC2 | Lifespan Biosciences | LS-F2369 | 50 |
| Phospho TSC2 | Lifespan Biosciences | LS-F1233 | 49 |
| Total AKT1 | Cell Signaling Technology | 7170 | 0048 |
| Phospho AKT1 | Cell Signaling Technology | 7160 | 0093 |
| Total mTOR | Cell Signaling Technology | 7974 | 0006 |
| Phospho mTOR | Cell Signaling Technology | 7976 | 0007 |
| Total p70S6K | Cell Signaling Technology | 7038 | 0004 |
| Phospho p70S6K | Cell Signaling Technology | 7063 | 0005 |

For Luminex Assays, AKT Pathway (total) Magnetic 7-Plex Panel (Thermo Fisher Scientific, PN: LHO0002M), AKT Pathway (phospho) Magnetic 7-Plex Panel (Thermo Fisher Scientific, PN: LHO0001M), Milliplex Map Akt/mTOR Phosphoprotein Magnetic Bead 11-Plex Kit (Millipore, PN: 48-611MAG) and Milliplex Map Total Akt/mTOR Magnetic Bead 11-Plex Kit (Millipore, PN: 48-612MAG) were used as recommended in instruction manuals. Luminex MagPix instrument was used to acquire and analyze Luminex assay data.

Immunoprecipitation and MS Sample Preparation

The Thermo Scientific™ Pierce MS-Compatible Magnetic IP Kit (Protein A/G) was used to screen and validate antibodies for 11 total and 10 phosphorylated AKT-mTOR pathway proteins from 500 µg cell lysate. Validated antibodies were biotinylated with the Thermo Scientific™ Pierce Antibody Biotinylation Kit for IP. The Thermo Scientific™ Pierce MS-Compatible Magnetic IP Kit (Streptavidin) was used to perform the single or multiplex IPs for target enrichment. IP samples were processed by an in-solution digestion method where IP eluates were reconstituted in 6M Urea, 50 mM TEAB, pH 8.5 followed by reduction, alkylation and trypsin digestion overnight at 37° C. The digested samples were acidified with TFA before MS analysis.

Liquid Chromatography and Mass Spectrometry

Prior to MS analysis, tryptic digest samples were desalted on-line using the Thermo Scientific™ Acclaim™ PepMap 100 C18 Trap Column. For discovery MS, the samples were analyzed by nanoLC-MS/MS using a Thermo Scientific™ Dionex™ UltiMate™ 3000 RSLCnano System and Thermo Scientific™ Q Exactive™ HF Hybrid Quadrupole-Orbitrap Mass Spectrometer. For targeted MS, the samples were analyzed using the UltiMate 3000 RSLCnano System and the Thermo Scientific™ TSQ™ Vantage™ Mass Spectrometer (SRM mode) or the Thermo Scientific™ Q Exactive™ HF Hybrid Quadrupole-Orbitrap Mass Spectrometer (PRM mode).

MS Data Analysis

Discovery MS data were analyzed with Thermo Scientific™ Proteome Discoverer™ 1.4 to assess percent sequence coverage, unique peptides, MS1 intensities, spectral counts and PTMs. The Proteome Discoverer software searches were executed using the Uniprot human protein database. Tryptic peptides with highest MS1 intensity and relevant phosphorylation sites were selected from the discovery data for targeted assay development. For targeted MS data analysis, Thermo Scientific™ Pinpoint software and Skyline software (University of Washington) were used to measure limit of quantitation (LOQ) from the calibration curve and target analyte concentration from unknown samples.

Results

As shown in FIG. 3, AKT-mTOR pathway proteins were immunoprecipitated from unstimulated and IGF-stimulated A549 lysate with Thermo Scientific™ Pierce MS-Compatible Magnetic IP Kits (Protein A/G or Streptavidin) for MS analysis. A variety of antibodies were screened to determine effectiveness in both ability to IP AKT-mTOR pathway proteins, and also for their usefulness when combined with MS. Table 1 (above) provides a list of antibodies validated for use in the IP-MS methods. Table 2 (above) provides a list of antibodies tested, but found to be less successful.

Higher numbers of unique peptides were identified in IP enriched samples as compared to neat (non-IP-enriched) lysate. See FIG. 3. Protein isoforms and interacting protein partners were identified for AKT, IGF1R and mTOR targets. Relevant phosphorylation sites were detected for AKT1, AKT2, mTOR, IGF1R and PRAS40. Candidate quantitative peptides were selected for targeted MS assay development.

Limits of detection (LOD) and lower limits of quantification (LLOQ) were analyzed for twelve AKT-mTOR pathway proteins, including AKT2, AKT1, mTOR, IGF1R, IR, PRAS40, p70S6K, TSC2, PTEN, GSK3alpha, GSK3beta, and IRS1. Results are presented in FIG. 4. The assay dynamic range, representing the concentration range between the lower to upper limits of quantification (LLOQ to ULOQ), is the range where protein concentration is measurable with acceptable levels of accuracy and precision. To ensure linearity of the measurement, for each internal standard peptide the linear signal-to-abundance range (LLOQ and ULOQ) was determined from dilution series experiments spanning concentrations of 500-0.08 fmol on column, spiked into a constant light peptide at 36 fmol and 200 ng of equimolar concentration of 6 proteins digest.

Example 2—Multiplex IP of AKT-mTOR Pathway Proteins and Multiplex MS

Eleven total and ten phosphorylated AKT-mTOR pathway protein targets were enriched simultaneously from unstimulated and IGF stimulated MCF7 lysates with biotinylated antibodies and Thermo Scientific™ Pierce MS-Compatible Magnetic IP Kit (Streptavidin). MCF7 cells were starved in 0.1% charcoal stripped FBS for 24 hours before stimulation with 100 ng/ml of IGF for 15 minutes. Validated IP-MS antibodies are biotinylated for 11 total and 10 phosphorylated AKT-mTOR pathway targets using the Thermo Scientific™ Pierce Antibody Biotinylation Kit for IP (PN: 90407) as recommended in instruction manual. 1 µg of each biotinylated antibody for 11 total targets were added simultaneously to 1000 µg of control and IGF stimulated MCF7 cell lysate in duplicate. 1 µg of each biotinylated antibody for 10 total targets were added simultaneously to 1000 µg of control and IGF stimulated MCF7 cell lysate in duplicate. IP was performed as recommended in the Thermo Scientific™ Pierce MS-Compatible Magnetic IP Kit (Streptavidin) (PN: 90408) with the following modification. 5 microgram of streptavidin magnetic beads per microgram of biotinylated antibody concentration was used for multiplex IP.

IP samples were processed by an in-solution digestion method where IP eluates were reconstituted in 6M Urea, 50 mM TEAB, pH 8.5 followed by reduction (5 mM TCEP for 30 minutes at 35° C.), alkylation (20 mM Iodoacetamide in dark at room temperature for 30 minutes) and trypsin digestion overnight at 37° C. The digested samples were acidified with 3.54, of 10% TFA before discovery MS analysis. For discovery MS, the samples were analyzed by nanoLC-MS/MS using a Thermo Scientific™ Dionex™ UltiMate™ 3000 RSLCnano System and Thermo Scientific™ Q Exactive™ HF Hybrid Quadrupole-Orbitrap Mass Spectrometer. Briefly, the digested samples were cleaned on-line using the C18 trap column (Thermo Fisher Scientific, PN: 164564) followed by reversed-phase separation using the analytical C18 column (75 µm i.d.×15 cm, nanoViper, 3 µm particle size, Thermo Fisher Scientific, PN: ES800) with a 2-30% gradient of Buffer B using Buffer A (0.1% formic acid) and Buffer B (0.1% formic acid/99.9% acetonitrile) at 0.300 µL/min.

FIG. 5 shows that the IP-nanoLC-MS/MS analysis was able to identify 11 proteins in the multiplex phosphor-assay, and 12 proteins for multiplex total assay. MS analysis of multiplex total assay identified interacting proteins (PIK3R1, PIK3R2, PIK3CB, PIK3CA, GSKIP and TSC1) of AKT-mTOR Pathway Targets. Tables 8 and 9 provide listings of the antibodies used in this multiplex IP.

Figure 6:
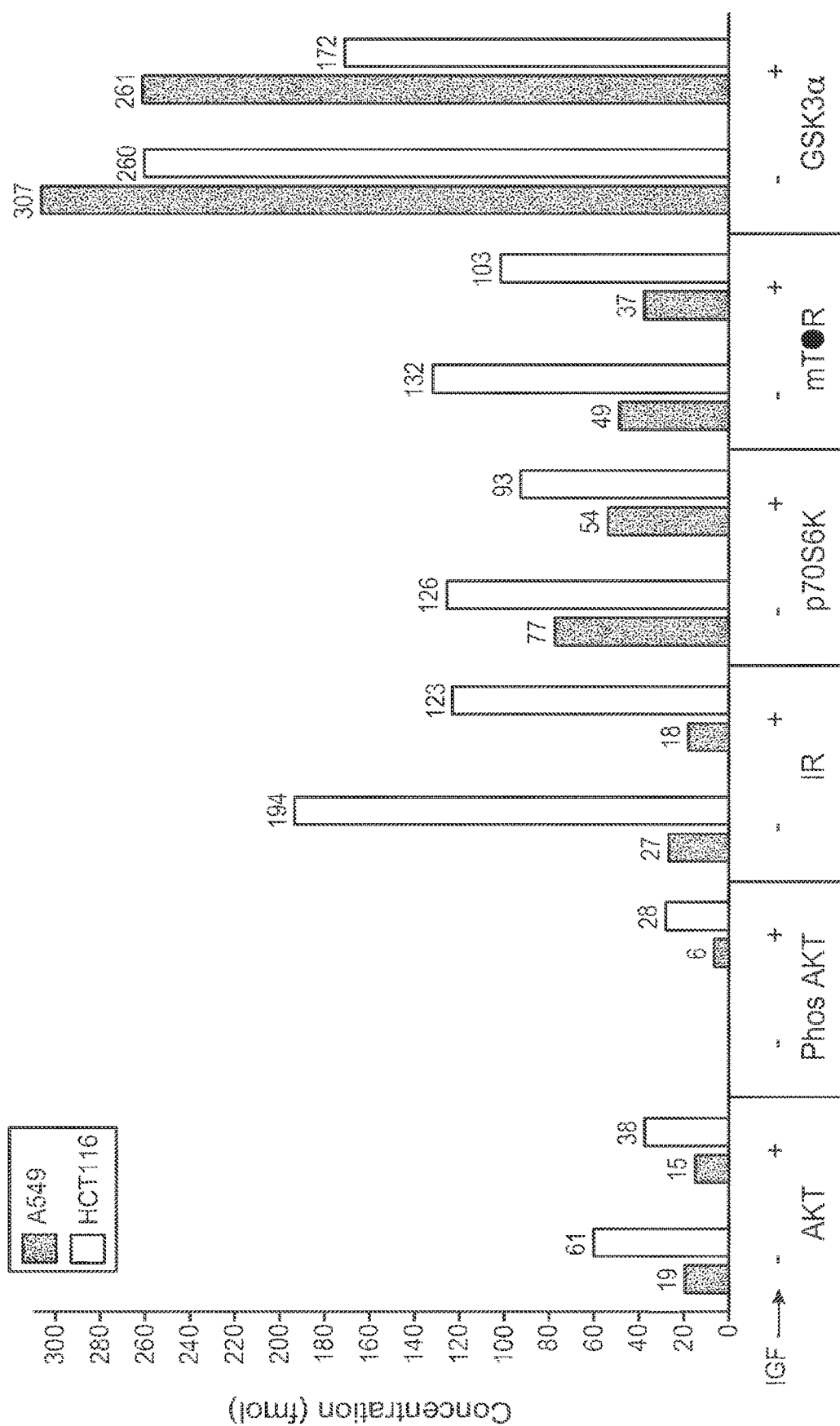
FIG. 6 shows representative results from a multiplex immunoprecipitation plus nanoLC-PRM/MS assay AKT-mTOR pathway proteins. Darker gray bars are A549 cells, and lighter gray bars are HCT116 cells.
Figure 7A:
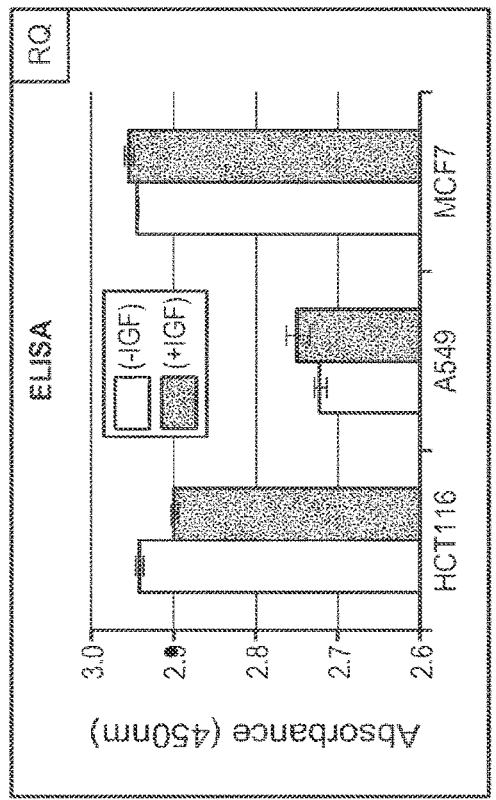
FIGS. 7A, 7B, 7C, 7D, 7E, 7F, and 7G, and 7H show a comparison of various methods to detect AKT-mTOR pathway proteins, including Luminex, ELISA, Western Blot, and the IP-Mass spec assay in IGF stimulated (dark gray) and non-stimulated (light gray) cells.
Figure 7B:
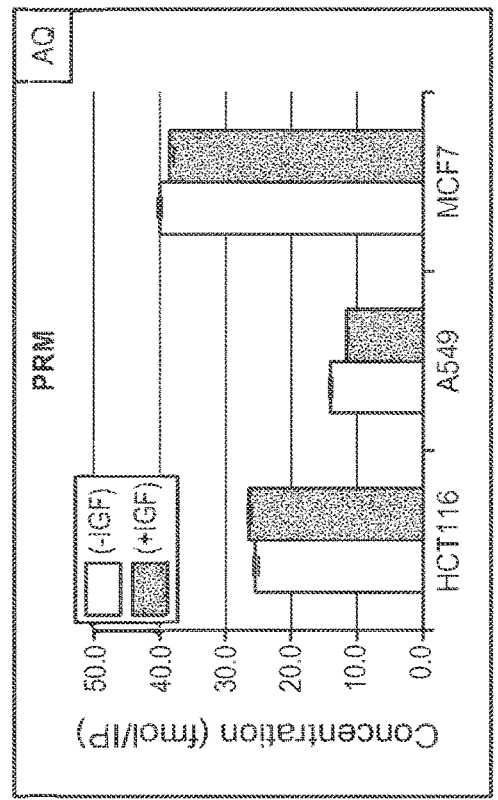
Figure 7C:
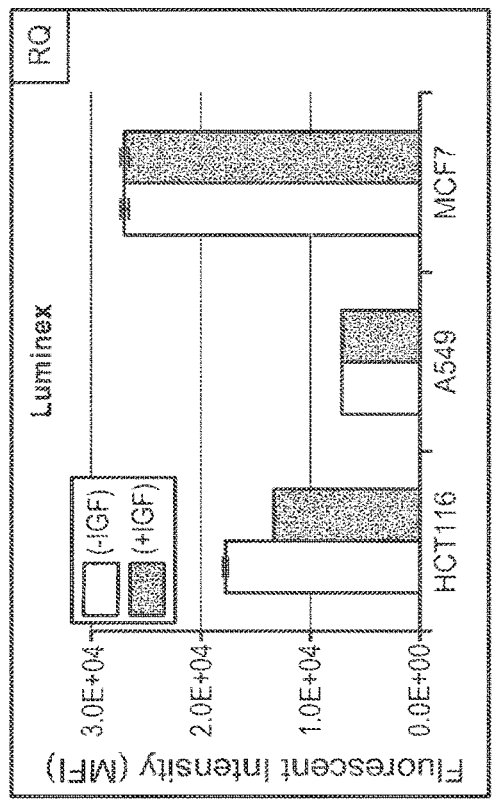
Figure 7D:
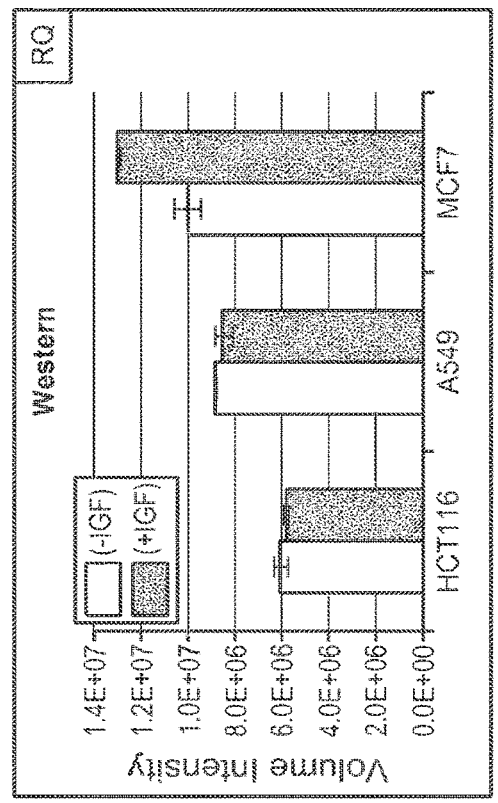
Figure 7E:
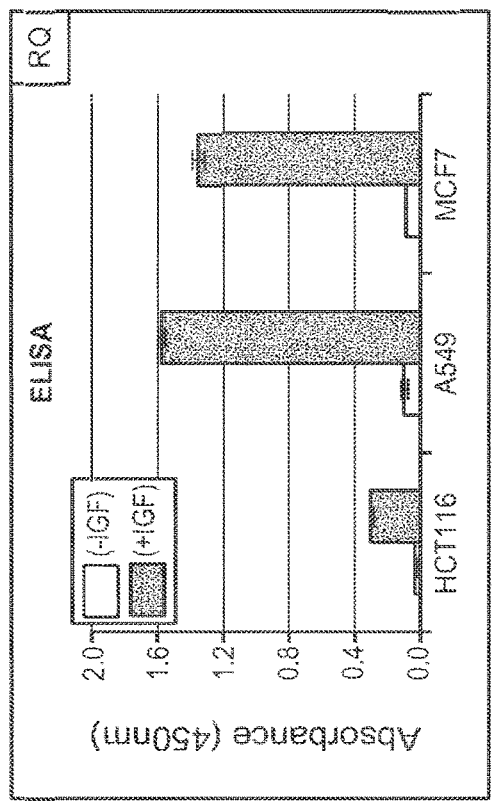
Figure 7F:
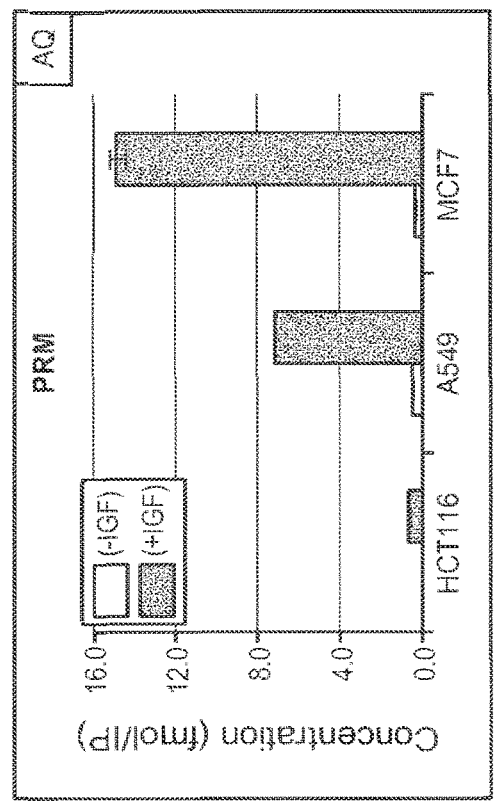
Figure 7G:
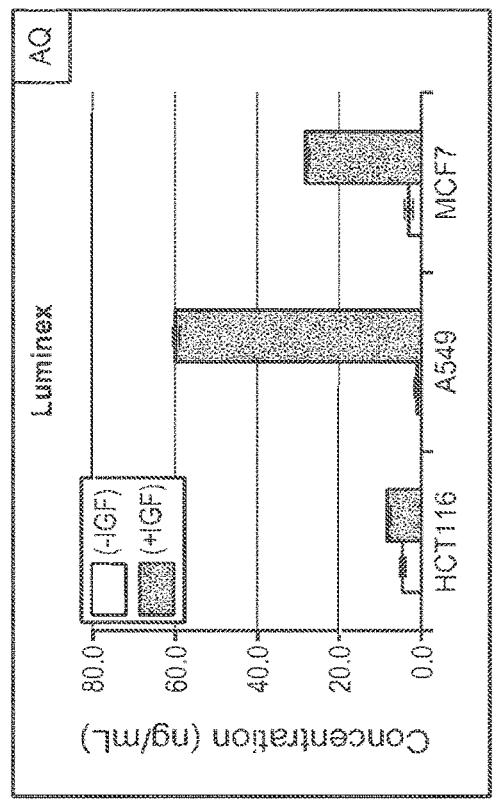
Figure 7H:
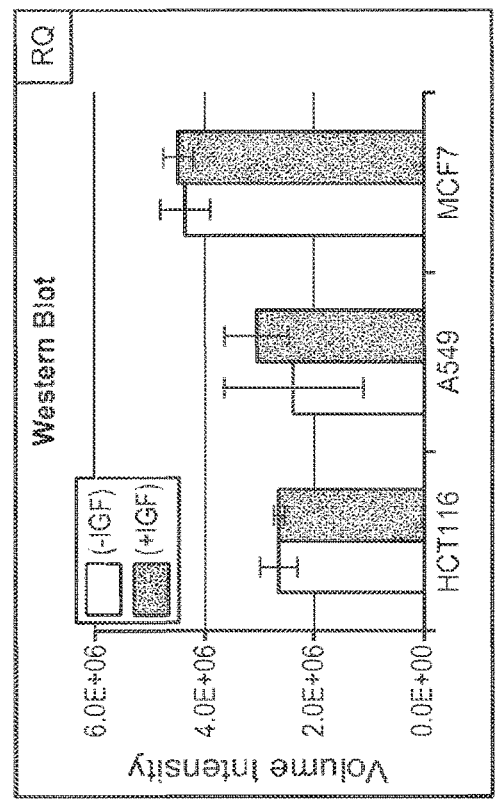

Next the ability of IP-MS to quantify sub-fmol concentrations of AKT-mTOR pathway proteins via the disclosed IP-MS methods was tested. As shown in FIG. 6, a multiplex IP enrichment of AKT (Total & Phospho), IR, p70S6K, mTOR, and GSK3α was performed from unstimulated and IGF stimulated A549 and HCT116 lysates with Thermo Scientific™ Pierce MS-Compatible Magnetic IP Kit (Streptavidin). A549 and HCT116 cells were starved in 0.1% charcoal stripped FBS for 24 hours before stimulation with 100 ng/ml of IGF for 15 minutes. Validated IP-MS antibodies are biotinylated for Total AKT, Phospho AKT, IR, p70S6K, mTOR, and GSK3α pathway targets using the Thermo Scientific™ Pierce Antibody Biotinylation Kit for IP (PN: 90407) as recommended in instruction manual. 1 µg of each biotinylated antibody was added simultaneously to 1000 µg of control and IGF stimulated A549 and HCT116 cell lysates in duplicate. IP was performed as recommended in the Thermo Scientific™ Pierce MS-Compatible Magnetic IP Kit (Streptavidin) (PN: 90408) with the following modification. 5 microgram of streptavidin magnetic beads per microgram of biotinylated antibody concentration was used for multiplex IP. IP samples were processed by an in-solution digestion method where IP eluates were reconstituted in 6M Urea, 50 mM TEAB, pH 8.5 followed by reduction (5 mM TCEP for 30 minutes at 35° C.), alkylation (20 mM Iodoacetamide in dark at room temperature for 30 minutes) and trypsin digestion overnight at 37° C. The digested samples were acidified with 3.5 µL of 10% TFA before discovery MS analysis. Internal standard peptides were spiked in digested IP samples to make final volume of 6.66 fmol/ul. For targeted MS, the samples were analyzed by nanoLC-PRM/MS using a Thermo Scientific™ Dionex™ UltiMate™ 3000 RSLCnano System and Thermo Scientific™ Q Exactive™ HF Hybrid Quadrupole-Orbitrap Mass Spectrometer. Briefly, the digested samples were cleaned on-line using the C18 trap column (Thermo Fisher Scientific, PN: 164564) followed by reversed-phase separation using the analytical C18 column (75 µm i.d.×15 cm, nanoViper, 3 µm particle size, Thermo Fisher Scientific, PN: ES800) with a 2-30% gradient of Buffer B using Buffer A (0.1% formic acid) and Buffer B (0.1% formic acid/99.9% acetonitrile) at 0.300 µL/min. Total targets were quantified in low to sub-fmol concentrations by nanoLC-PRM/MS. Up-regulation of phospho AKT was seen after IGF stimulation in both A549 and HCT116 cell lines. The slight decrease in concentrations for total AKT, IR, mTOR, GSK3a and p70S6K targets was observed after IGF stimulation in both A549 and HCT116 cells.

Example 3—Benchmarking

Next, comparison of mIP-tMS assays with current immunoassay techniques to quantitate AKT-mTOR pathway targets from unstimulated and IGF stimulated A549, HCT116 and MCF7 lysates were performed. Western Blot, ELISA, and Luminex assays were performed as described above and according to manufacturer's instructions. mIP-tMS was performed as in Example 2.

FIGS. 7A-7D show quantitation of total AKT. FIGS. 7E-7H show quantitation of phosphorylated IGF1R across all 4 techniques. Lower correlation was observed across techniques. The lower correlation could be due to different antibodies used or each assay and antibody specificity. Up-regulation in phosphorylated IGF1R observed after IGF stimulation in 3 of 4 techniques. Western blot for phosphor IGF1R showed no significant differences in control and IGF stimulated cell lysates.

A summary of AKT-mTOR pathway proteins that were identified and quantified using the IP-MS methods described herein is provided in FIG. 8. Most of the AKT-mTOR pathway targets were not identified in discovery MS and quantitated by targeted MS (PRM or SRM) without enrichment by immunoprecipitation.

Immunoprecipitation using particular selected antibodies resulted in a higher yield of AKT-mTOR pathway target proteins and less non-specific binding proteins than MS alone. IP-MS assay was also more successful than other commercially available non-MS assays. Furthermore, IP to MS analysis of total and phosphorylated AKT-mTOR pathway proteins enabled identification of multiple isoforms, relevant protein interactions and phosphorylation sites. Total and phosphorylated mIP-tMS assays allowed simultaneous quantitation of 12 total and 11 phosphorylated AKT-mTOR pathway proteins in the low to sub-fmol range from unstimulated and IGF stimulated A549, HCT116 and MCF7 cell lysates. The benchmarking of mIP-tMS assays showed moderate correlation for quantitation of total and phosphorylated target relative abundance compared to WB, ELISA and Luminex assays. The low concordance for a few targets is possibly due to differences in the specificity of antibodies used for each assay. Major advantages of the MS-based assay are high confidence in target identity coupled with simultaneous quantitation of multiple targets, interacting proteins and their phosphophorylated forms.

Example 4—Tissue Sample Validation

Tissue lysis protocol was optimized for IP-MS application. Briefly, 50-100 mg of human and murine tissue samples were washed with 5 mL 1× cold PBS three times. Tissue samples was minced in 5 mL 1× cold PS using scissor followed by homogenization in IP lysis buffer (Thermo Fisher Scientific PN: 87788) and electronic Polytron Hand-held Tissue Tearer. Homogenized tissue samples were passed through tissue strainer (Thermo Fisher Scientific PN: 87791) to prepare tissue lysates before IP. To validate the IP-MS method in murine and human tissue lysate, eleven total and ten phosphorylated AKT-mTOR pathway protein targets were enriched simultaneously from normal mouse lung tissue lysate, normal mouse kidney tissue lysate, and normal human lung tissue lysate as per Example 2. A549 cell lysate was used as a non-tissue control. As shown in Table 10, the IP-MS method described herein is capable of validating AKT-mTOR pathway proteins in murine and human tissue lysate in addition to cell lysate. Seven out of eleven AKT-mTOR pathway protein targets were identified in normal human lung tissue, and nine out of eleven AKT-mTOR pathway protein targets were identified for normal mouse kidney tissue using our IP-MS method.

TABLE 10

11-plex total IP-MS assay validating tissue lysate.
Intensities of top 3 peptides

| Total Targets | A549 Cell Line | Mouse Lung | Human Lung | Mouse Kidney |
|---|---|---|---|---|
| AKT1 | 2.0E+08 | 1.2E+08 | 2.6E+06 | |
| PRAS40 | 9.8E+08 | 1.0E+08 | 2.3E+07 | 2.5E+07 |
| GSK3b | 8.0E+08 | 8.3E+08 | 1.2E+08 | 3.4E+08 |
| IGF1R | 5.4E+08 | 7.4E+07 | 1.2E+07 | 1.4E+08 |

TABLE 10-continued 11-plex total IP-MS assay validating tissue lysate.
Intensities of top 3 peptides

| Total Targets | A549 Cell Line | Mouse Lung | Human Lung | Mouse Kidney |
|---|---|---|---|---|
| IRS1 | 7.2E+07 | 7.1E+06 | | |
| IR1 | 2.1E+08 | 6.2E+07 | 3.4E+07 | 1.5E+08 |
| mTOR | 9.4E+07 | 1.3E+07 | 2.2E+07 | 6.7E+07 |
| p70S6K | 6.4E+07 | 3.8E+08 | | 1.8E+08 |
| TSC2 | 9.1E+07 | 1.9E+07 | | 3.7E+07 |
| PTEN | 6.1E+07 | 5.3E+07 | 2.4E+07 | 1.3E+08 |
| GSk3a | 2.8E+08 | 1.4E+08 | | 9.2E+07 |

---

What is claimed:

1. A method for determining the ratio of phosphorylated to non-phosphorylated AKT-mTOR pathway proteins, comprising
   a. treating a biological sample with one or more antibodies capable of immunoprecipitating a phosphorylated AKT-mTOR target protein, and separately treating the same biological sample with one or more antibodies capable of immunoprecipitating a non-phosphorylated AKT-mTOR target protein;
   b. digesting the immunoprecipitated AKT-mTOR pathway proteins;
   c. adding a first and a second detectably labelled internal standard peptide of known amount to the digested proteins, wherein the first internal standard peptide has the same amino acid sequence as a phosphorylated AKT-mTOR pathway peptide used to identify the phosphorylated protein, and the second internal standard peptide has the same amino acid sequence as the non-phosphorylated AKT-mTOR pathway peptide used to identify the non-phosphorylated protein;
   d. assaying the digested proteins and internal standards via mass spectrometry to determine the presence and amount of phosphorylated and non-phosphorylated AKT-mTOR pathway peptides, wherein the AKT-mTOR pathway peptide is selected from the group consisting of SEQ ID NO: 5, 21, 44-46, 53, 59, 66, 74, 75, 80, 82, 84, 87, 103, 104, 108, 126, 131, 132, 143, 153, 156, 160, 166, 174, 196, 200, 205 and 212, and
   e. determining the quantity of AKT-mTOR phosphorylated and non-phosphorylated pathway proteins in the sample, and determining the ratio of phosphorylated to non-phosphorylated target proteins.

2. The method of claim 1, wherein the biological sample is from a human.

3. The method of claim 1, wherein the antibody to detect phosphorylated AKT-mTOR pathway protein comprises an antibody that binds to phosphorylated AKT, phosphorylated IGF1R, phosphorylated IRS, phosphorylated IRS1, phosphorylated mTOR, phosphorylated P70S6K, phosphorylated GSK3a, phosphorylated GSK3b, phosphorylated TSC2, phosphorylated PRAS40, or phosphorylated PTEN.

4. The method of claim 1, wherein the antibody to detect non-phosphorylated AKT-mTOR pathway protein comprises an antibody that binds to AKT, IGF1R, IRS, IRS1, mTOR, P70S6K, GSK3a, GSK3b, TSC2, PRAS40, or PTEN.

5. The method of claim 1, wherein the peptide is modified with a detectable label.

6. The method of claim 1, wherein the antibody is selected from the antibodies that bind to AKT1, AKT (pan), AKT2, phosphorylated AKT2 (pSer474), phosphorylated AKT (pSer473), phosphorylated IGF-1R (Tyr1161/Tyr1165/Tyr1166), phosphorylated IGF1 Receptor (IGF1R) pTyr1158+1162+1163, phosphorylated IGF1R pTyr1161, phosphorylated IGF-I Receptor β (Tyr1131), phosphorylated Insulin Receptor β (Tyr1146), IGF-I/Insulin Receptor β, INSR/Insulin Receptor, α-Insulin Receptor β subunit, INSR/Insulin Receptor alpha, phosphorylated Insulin Receptor (Y972), IRS1, phosphorylated IRS1 (pSer312), phosphorylated IRS1 (Ser307 mouse/Ser312 human), phosphorylated IRS-1 (pSer1101), mTOR, phosphorylated mTOR (pSer2448), S6K, S6K1, phosphorylated p70 S6 Kinase (pThr389/pThr412), phosphorylated p70 S6 Kinase (pThr389), phosphorylated p70 S6 Kinase (pThr421/pSer424), phosphorylated GSK-3α/β (pSer21/pSer9), GSK3α, phosphorylated GSK-3α (Ser21), GSK-3β, phosphorylated GSK-3β (pSer9), phosphorylated Tuberin/TSC2 (pSer939), TSC2, S6 ribosomal protein, phosphorylated S6 ribosomal protein (pSer235+236), PRAS40, phosphorylated PRAS40 (pThr246), phosphorylated PTEN (pSer380), or PTEN.

7. The method of claim 6, wherein the antibody is capable of immunoprecipitating more than one AKT-mTOR pathway protein.

8. The method of claim 1, wherein a first antibody is capable of immunoprecipitating a phosphorylated AKT-mTOR pathway protein, and a second antibody is capable of immunoprecipitating a non-phosphorylated version of the AKT-mTOR pathway protein precipitated by the first antibody.

9. The method of claim 1, wherein step a) comprises treating the sample with a labelled antibody capable of binding to the pathway protein to provide a labelled antibody-protein conjugate; and binding the labelled antibody-protein conjugate with a capture agent capable of binding to the labelled antibody to isolate the target protein from the sample.

10. The method of claim 1, wherein the quantity of an AKT-mTOR pathway protein is determined by adding an internal standard peptide of known amount to the digested protein prior to mass spectrometry, wherein the internal standard peptide has the same amino acid sequence as the AKT-mTOR pathway peptide, and is detectably labeled, and determining the quantity of an AKT-mTOR pathway peptide by comparison to the internal standard.

11. The method of claim 1, wherein the quantity of an AKT-mTOR pathway protein is determined by a method comprising comparing an amount of an AKT-mTOR pathway peptide in the sample to the amount of the same AKT-mTOR pathway peptide in a control sample.

12. The method of claim 1, wherein the quantity of an AKT-mTOR pathway protein is determined by a method comprising comparing an amount of the AKT-mTOR pathway peptide to an internal standard peptide of known amount, wherein both the peptide in the biological sample and the internal standard peptide are selected from the group consisting of SEQ ID NO: 5, 21, 44-46, 53, 59, 66, 74, 75, 80, 82, 84, 87, 103, 104, 108, 126, 131, 132, 143, 153, 156, 160, 166, 174, 196, 200, 205 and 212, wherein the standard peptide is detectably labeled.

13. The method of claim 1, wherein the internal standard peptide is selected from the group consisting of SEQ ID NO: 5, 21, 44-46, 53, 59, 66, 74, 75, 80, 82, 84, 87, 103, 104, 108, 126, 131, 132, 143, 153, 156, 160, 166, 174, 196, 200, 205 and 212.

14. The method of claim 1, wherein the digesting comprises a protease or chemical digest.

15. The method of claim 1, wherein the digestion is single or sequential.

16. The method of claim 1, further comprising desalting after digestion and prior to mass spectrometry.

17. The method of claim 1, wherein the AKT-mTOR pathway protein is selected from RAC-alpha serine/threonine-protein kinase (AKT1), RAC-beta serine/threonine-protein kinase (AKT2), insulin receptor (INSR), insulin-like growth factor 1 receptor (IGF1R), insulin receptor substrate 1 (IRS1), tuberin (TSC2), serine/threonine-protein kinase mTOR (mTOR), glycogen synthase kinase-3 alpha (GSK3a), glycogen synthase kinase-3 beta (GSK3b), GSK3a/GSK3b, ribosomal protein S6 kinase beta-1 (p70S6K; RPS6KB1), 40S ribosomal protein S6 (RPS6), proline-rich AKT1 substrate 1 (PRAS40; AKT1S1), and phosphatidylinositol 3,4,5-triphosphate 3-phosphatase and dual-specificity protein phosphatase (PTEN).

18. The method of claim 1, wherein a lower limit of quantification is from 0.05 to 0.75 fmol.

\* \* \* \* \*

UNITED STATES PATENT AND TRADEMARK OFFICE
CERTIFICATE OF CORRECTION

PATENT NO. : 12,228,576 B2  
APPLICATION NO. : 18/068047  
DATED : February 18, 2025  
INVENTOR(S) : Bhavinkumar Patel et al.

It is certified that error appears in the above-identified patent and that said Letters Patent is hereby corrected as shown below:

In the Claims

In Column 181, Claim 1, Lines 52-53, delete "comprising" and insert -- comprising: --, therefor.

In Column 182, Claim 1, Line 59, delete "212," and insert -- 212; --, therefor.

In Column 184, Claim 13, Line 24, delete "1," and insert -- 10, --, therefor.

Signed and Sealed this  
Tenth Day of June, 2025

Coke Morgan Stewart  
*Acting Director of the United States Patent and Trademark Office*